(12) United States Patent
Howard et al.

(10) Patent No.: US 10,010,624 B2
(45) Date of Patent: *Jul. 3, 2018

(54) PYRROLOBENZODIAZEPINE-ANTIBODY CONJUGATES

(71) Applicant: MEDIMMUNE LIMITED, Cambridge (GB)

(72) Inventors: Philip Wilson Howard, Cambridge (GB); Patricius Hendrikus Cornelis Van Berkel, Epalinges (CH)

(73) Assignee: Medimmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/028,583

(22) PCT Filed: Oct. 10, 2014

(86) PCT No.: PCT/GB2014/053051
§ 371 (c)(1),
(2) Date: Apr. 11, 2016

(87) PCT Pub. No.: WO2015/052532
PCT Pub. Date: Apr. 16, 2015

(65) Prior Publication Data
US 2016/0263239 A1   Sep. 15, 2016

(30) Foreign Application Priority Data

Oct. 11, 2013 (GB) .................... 1317981.7
Oct. 11, 2013 (GB) .................... 1317982.5
Apr. 15, 2014 (GB) .................... 1406721.9

(51) Int. Cl.
| | | |
|---|---|---|
| A61K 39/395 | (2006.01) | |
| A61K 47/48 | (2006.01) | |
| A61K 45/06 | (2006.01) | |
| C07K 16/40 | (2006.01) | |

(52) U.S. Cl.
CPC ........ *A61K 47/48384* (2013.01); *A61K 45/06* (2013.01); *A61K 47/48638* (2013.01); *C07K 16/40* (2013.01); *C07K 2317/24* (2013.01); *C07K 2317/56* (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 3,361,742 A | 1/1968 | Julius et al. | |
| 3,523,941 A | 8/1970 | Leimgruber et al. | |
| 3,524,849 A | 8/1970 | Batcho et al. | |
| 3,794,644 A | 2/1974 | Karlyone et al. | |
| 4,185,016 A | 1/1980 | Takanabe et al. | |
| 4,239,683 A | 12/1980 | Takanabe et al. | |
| 4,309,437 A | 1/1982 | Ueda et al. | |
| 4,353,827 A | 10/1982 | Hunkeler et al. | |
| 4,382,032 A | 5/1983 | Hunkeler et al. | |
| 4,386,028 A | 5/1983 | Hunkeler et al. | |
| 4,405,516 A | 9/1983 | Hunkeler et al. | |
| 4,405,517 A | 9/1983 | Hunkeler et al. | |
| 4,407,752 A | 10/1983 | Hunkeler et al. | |
| 4,427,587 A | 1/1984 | Kaneko et al. | |
| 4,427,588 A | 1/1984 | Kaneko et al. | |
| 4,701,325 A | 10/1987 | Ueda et al. | |
| 4,816,567 A | 3/1989 | Cabilly et al. | |
| 4,923,984 A | 5/1990 | Matsumura et al. | |
| 5,362,852 A | 11/1994 | Geoghegan | |
| 5,418,241 A | 5/1995 | Jegham et al. | |
| 5,440,021 A | 8/1995 | Chuntharapai et al. | |
| 5,583,024 A | 12/1996 | McElroy et al. | |
| 5,621,002 A | 4/1997 | Bosslet et al. | |
| 5,644,033 A | 7/1997 | Seon | |
| 5,674,713 A | 10/1997 | McElroy et al. | |
| 5,700,670 A | 12/1997 | Yamagishi et al. | |
| 5,773,223 A | 6/1998 | Shyamala et al. | |
| 5,792,616 A | 8/1998 | Persico et al. | |
| 5,854,399 A | 12/1998 | Salomon et al. | |
| 5,869,445 A | 2/1999 | Cheever et al. | |
| 5,976,551 A | 11/1999 | Mottez et al. | |
| 6,011,146 A | 1/2000 | Mottez et al. | |
| 6,153,408 A | 11/2000 | Abastado et al. | |
| 6,214,345 B1 | 4/2001 | Firestone et al. | |
| 6,218,519 B1 | 4/2001 | Kenten et al. | |
| 6,268,488 B1 | 7/2001 | Barbas, III et al. | |
| 6,362,331 B1 | 3/2002 | Kamal et al. | |
| 6,518,404 B1 | 2/2003 | Li et al. | |
| 6,534,482 B1 | 3/2003 | Fikes et al. | |

(Continued)

FOREIGN PATENT DOCUMENTS

| | | |
|---|---|---|
| EP | 0522868 | 1/1993 |
| EP | 0875569 | 11/1998 |

(Continued)

OTHER PUBLICATIONS

Adair, J.R. et al., "Antibody-drug conjugates—a perfect synergy," Exp. Opin. Biol. Ther. (2012) 16 pages.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.
Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

(Continued)

*Primary Examiner* — Sheela J. Huff
(74) *Attorney, Agent, or Firm* — Melissa E. Kolom; Casimir Jones, S.C.

(57) ABSTRACT

Conjugates of specific PBD dimers with an antibody that binds to PSMA, the antibody comprising a VH domain having the sequence according to any one of SEQ ID NOs. 1, 3, 5, 7, 8, 9, or 10, optionally further comprising a VL domain having the sequence 5 according to any one of SEQ ID NOs. 2, 4, 6, 11, 12, 13, 14, 15, 16, 17, or 18.

11 Claims, 1 Drawing Sheet

(56) References Cited

U.S. PATENT DOCUMENTS

| | | |
|---|---|---|
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Susaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Howard et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 10/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0062793 A1 | 3/2006 | Webb et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | Mcdonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2011/0091372 A1 | 4/2011 | Ghayur et al. |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0275522 A1 | 9/2014 | Howard et al. |
| 2014/0294868 A1 | 10/2014 | Howard et al. |
| 2015/0283258 A1 | 10/2015 | Van Berkel et al. |

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 53-82792 | 7/1978 |
| JP | 57131791 | 8/1982 |
| JP | 58-180487 | 10/1983 |

(56) References Cited

FOREIGN PATENT DOCUMENTS

| | | |
|---|---|---|
| JP | 58180487 | 10/1983 |
| JP | 05003790 | 1/1993 |
| JP | 2004113151 | 4/2004 |
| WO | WO 91/02536 | 3/1991 |
| WO | WO 92/07574 | 5/1992 |
| WO | WO 92/17497 | 10/1992 |
| WO | WO 92/19620 | 11/1992 |
| WO | WO 93/18045 | 9/1993 |
| WO | WO 94/10312 | 5/1994 |
| WO | WO 94/28931 | 12/1994 |
| WO | WO 95/04718 | 2/1995 |
| WO | WO 96/30514 | 10/1996 |
| WO | WO 97/07198 | 2/1997 |
| WO | WO 97/44452 | 11/1997 |
| WO | WO 98/13059 | 4/1998 |
| WO | WO 98/37193 | 8/1998 |
| WO | WO 98/40403 | 9/1998 |
| WO | WO 98/51805 | 11/1998 |
| WO | WO 98/51824 | 11/1998 |
| WO | WO 99/28468 | 6/1999 |
| WO | WO 99/46284 | 9/1999 |
| WO | WO 99/58658 | 11/1999 |
| WO | WO 00/03291 | 1/2000 |
| WO | WO 00/12130 | 3/2000 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 00/14228 | 3/2000 |
| WO | WO 00/20579 | 4/2000 |
| WO | WO 00/22129 | 4/2000 |
| WO | WO 00/32752 | 6/2000 |
| WO | WO 00/36107 | 6/2000 |
| WO | WO 00/40614 | 7/2000 |
| WO | WO 00/44899 | 8/2000 |
| WO | WO 00/53216 | 9/2000 |
| WO | WO 00/55351 | 9/2000 |
| WO | WO 00/75655 | 12/2000 |
| WO | WO 01/00244 | 1/2001 |
| WO | WO 01/16318 | 3/2001 |
| WO | WO 01/38490 | 5/2001 |
| WO | WO 01/40269 | 6/2001 |
| WO | WO 01/40309 | 6/2001 |
| WO | WO 01/41787 | 6/2001 |
| WO | WO 01/45746 | 6/2001 |
| WO | WO 01/46232 | 6/2001 |
| WO | WO 01/46261 | 6/2001 |
| WO | WO 01/48204 | 7/2001 |
| WO | WO 01/53463 | 7/2001 |
| WO | WO 01/57188 | 8/2001 |
| WO | WO 01/62794 | 8/2001 |
| WO | WO 01/66689 | 9/2001 |
| WO | WO 01/72830 | 10/2001 |
| WO | WO 01/72962 | 10/2001 |
| WO | WO 01/75177 | 10/2001 |
| WO | WO 01/77172 | 10/2001 |
| WO | WO 01/88133 | 11/2001 |
| WO | WO 01/90304 | 11/2001 |
| WO | WO 01/94641 | 12/2001 |
| WO | WO 01/98351 | 12/2001 |
| WO | WO 02/02587 | 1/2002 |
| WO | WO 02/02624 | 1/2002 |
| WO | WO 02/02634 | 1/2002 |
| WO | WO 02/06317 | 1/2002 |
| WO | WO 02/06339 | 1/2002 |
| WO | WO 02/10187 | 2/2002 |
| WO | WO 02/10382 | 2/2002 |
| WO | WO 02/12341 | 2/2002 |
| WO | WO 02/13847 | 2/2002 |
| WO | WO 02/14503 | 2/2002 |
| WO | WO 02/16413 | 2/2002 |
| WO | WO 02/16429 | 2/2002 |
| WO | WO 02/22153 | 3/2002 |
| WO | WO 02/22636 | 3/2002 |
| WO | WO 02/22660 | 3/2002 |
| WO | WO 02/22808 | 3/2002 |
| WO | WO 02/24909 | 3/2002 |
| WO | WO 02/26822 | 4/2002 |
| WO | WO 02/30268 | 4/2002 |
| WO | WO 02/38766 | 5/2002 |
| WO | WO 02/54940 | 7/2002 |
| WO | WO 02/59377 | 8/2002 |
| WO | WO 02/60317 | 8/2002 |
| WO | WO 02/61087 | 8/2002 |
| WO | WO 02/64798 | 8/2002 |
| WO | WO 02/71928 | 9/2002 |
| WO | WO 02/72596 | 9/2002 |
| WO | WO 02/78524 | 10/2002 |
| WO | WO 02/81646 | 10/2002 |
| WO | WO 02/83866 | 10/2002 |
| WO | WO 02/86443 | 10/2002 |
| WO | WO 02/88170 | 11/2002 |
| WO | WO 02/88172 | 11/2002 |
| WO | WO 02/89747 | 11/2002 |
| WO | WO 02/92836 | 11/2002 |
| WO | WO 02/94852 | 11/2002 |
| WO | WO 02/98358 | 12/2002 |
| WO | WO 02/98897 | 12/2002 |
| WO | WO 02/99074 | 12/2002 |
| WO | WO 02/99122 | 12/2002 |
| WO | WO 02/101075 | 12/2002 |
| WO | WO 02/102235 | 12/2002 |
| WO | WO 03/000842 | 1/2003 |
| WO | WO 03/002717 | 1/2003 |
| WO | WO 03/003906 | 1/2003 |
| WO | WO 03/003984 | 1/2003 |
| WO | WO 03/004529 | 1/2003 |
| WO | WO 03/004989 | 1/2003 |
| WO | WO 03/008537 | 1/2003 |
| WO | WO 03/009814 | 2/2003 |
| WO | WO 03/014294 | 2/2003 |
| WO | WO 03/016475 | 2/2003 |
| WO | WO 03/016494 | 2/2003 |
| WO | WO 03/018621 | 3/2003 |
| WO | WO 03/022995 | 3/2003 |
| WO | WO 03/023013 | 3/2003 |
| WO | WO 03/024392 | 3/2003 |
| WO | WO 03/025138 | 3/2003 |
| WO | WO 03/025148 | 3/2003 |
| WO | WO 03/025228 | 3/2003 |
| WO | WO 03/026493 | 4/2003 |
| WO | WO 03/026577 | 4/2003 |
| WO | WO 03/029262 | 4/2003 |
| WO | WO 03/029277 | 4/2003 |
| WO | WO 03/029421 | 4/2003 |
| WO | WO 03/034984 | 5/2003 |
| WO | WO 03/035846 | 5/2003 |
| WO | WO 03/042661 | 5/2003 |
| WO | WO 03/043583 | 5/2003 |
| WO | WO 03/045422 | 6/2003 |
| WO | WO 03/048202 | 6/2003 |
| WO | WO 03/054152 | 7/2003 |
| WO | WO 03/055439 | 7/2003 |
| WO | WO 03/055443 | 7/2003 |
| WO | WO 03/060612 | 7/2003 |
| WO | WO 03/062401 | 7/2003 |
| WO | WO 03/072035 | 9/2003 |
| WO | WO 03/072036 | 9/2003 |
| WO | WO 03/077836 | 9/2003 |
| WO | WO 03/081210 | 10/2003 |
| WO | WO 03/083041 | 10/2003 |
| WO | WO 03/083047 | 10/2003 |
| WO | WO 03/083074 | 10/2003 |
| WO | WO 03/087306 | 10/2003 |
| WO | WO 03/087768 | 10/2003 |
| WO | WO 03/088808 | 10/2003 |
| WO | WO 03/089624 | 10/2003 |
| WO | WO 03/089904 | 10/2003 |
| WO | WO 03/093444 | 11/2003 |
| WO | WO 03/097803 | 11/2003 |
| WO | WO 03/101283 | 12/2003 |
| WO | WO 03/101400 | 12/2003 |
| WO | WO 03/104270 | 12/2003 |
| WO | WO 03/104275 | 12/2003 |

(56) References Cited

FOREIGN PATENT DOCUMENTS

| | | |
|---|---|---|
| WO | WO 03/104399 | 12/2003 |
| WO | WO 03/105758 | 12/2003 |
| WO | WO 2004/000221 | 12/2003 |
| WO | WO 2004/000997 | 12/2003 |
| WO | WO 2004/001004 | 12/2003 |
| WO | WO 2004/005598 | 1/2004 |
| WO | WO 2004/009622 | 1/2004 |
| WO | WO 2004/011611 | 2/2004 |
| WO | WO 2004/015426 | 2/2004 |
| WO | WO 2004/016225 | 2/2004 |
| WO | WO 2004/020583 | 3/2004 |
| WO | WO 2004/020595 | 3/2004 |
| WO | WO 2004/022709 | 3/2004 |
| WO | WO 2004/022778 | 3/2004 |
| WO | WO 2004/027049 | 4/2004 |
| WO | WO 2004/031238 | 4/2004 |
| WO | WO 2004/032828 | 4/2004 |
| WO | WO 2004/032842 | 4/2004 |
| WO | WO 2004/040000 | 5/2004 |
| WO | WO 2004/042346 | 5/2004 |
| WO | WO 2004/043361 | 5/2004 |
| WO | WO 2004/043963 | 5/2004 |
| WO | WO 2004/044178 | 5/2004 |
| WO | WO 2004/045516 | 6/2004 |
| WO | WO 2004/045520 | 6/2004 |
| WO | WO 2004/045553 | 6/2004 |
| WO | WO 2004/046342 | 6/2004 |
| WO | WO 2004/047749 | 6/2004 |
| WO | WO 2004/048938 | 6/2004 |
| WO | WO 2004/053079 | 6/2004 |
| WO | WO 2004/058309 | 7/2004 |
| WO | WO 2004/063355 | 7/2004 |
| WO | WO 2004/063362 | 7/2004 |
| WO | WO 2004/063709 | 7/2004 |
| WO | WO 2004/065576 | 8/2004 |
| WO | WO 2004/065577 | 8/2004 |
| WO | WO 2004/074320 | 9/2004 |
| WO | WO 2005/023814 | 3/2005 |
| WO | WO 2005/040170 | 5/2005 |
| WO | WO 2005/042535 | 5/2005 |
| WO | WO 2005/079479 | 9/2005 |
| WO | WO 2005/082023 | 9/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/044515 | 4/2007 |
| WO | WO 2007/085930 | 8/2007 |
| WO | WO 2008/010101 | 1/2008 |
| WO | WO 2008/047242 | 4/2008 |
| WO | WO 2008/070593 | 6/2008 |
| WO | WO 2009/016516 | 2/2009 |
| WO | WO 2009/052249 | 4/2009 |
| WO | WO 2009/117531 | 9/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/038159 | 3/2011 |
| WO | WO 2011/100227 | 8/2011 |
| WO | WO 2011/130598 | 10/2011 |
| WO | WO 2011/130613 | 10/2011 |
| WO | WO 2011/130615 | 10/2011 |
| WO | WO 2011/130616 | 10/2011 |
| WO | WO 2012/112708 | 8/2012 |
| WO | WO 2012/128868 | 9/2012 |
| WO | WO 2012/153193 | 11/2012 |
| WO | WO 2013/041606 | 3/2013 |
| WO | WO 2013/053871 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2014/011518 | 1/2014 |
| WO | WO 2014/011519 | 1/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/022679 | 6/2014 |

OTHER PUBLICATIONS

Alley, S. C., Bioconjugate Chem 2008, 19, 759-765.
Althius, T. H. and Hess, H. J., "Synthesis and Identification of the Major Metabolites of Prazosin Formed in Dog and Rat," J. Medicinal Chem. (1977) 20(1):146-148.
Altuvia et al., J. Mol. Biol., 249, 244-250 (1995).
Amiel J., et al., "Heterozygous endothelin receptor B {EDNRB) mutations in isolated Hirschsprung disease," Hum. Mol. Genet. 5, 355-357, 1996.
Amir et al., "Self-Immolative Dendrimers," (2003) Angew. Chem. Int. Ed. 42:4494-4499.
Amsberry, et al, "The Lactonization of 2'-Hydroxyhydrocinnamic Acid Amides: A Potential Prodrug for Amines," (1990) J. Org. Chem. 55:5867-5877.
Antonow, D. et al., "Synthesis of DNA-Interactive Pyrrolo [2,1-c][1,4] benzodiazepines (PBDs)" Chemical Reviews, 2011, 111(4):2815-2864.
Antonow, D. et al., J Med. Chem., 2010, 53, 2927-2941.
Antonow, D. et al.,"Parallel synthesis of a novel C2-aryl pyrrolo[2,1-c][1,4]benzodiazepine (PBD) library," J. Comb. Chem. (2007) 9:437-445.
Arai H., et al., "Molecular cloning of human endothelin receptors and their expressiOn in vascular endothelial cells and smooth muscle cells," Jpn. Circ. J. 56, 1303-1307, 1992.
Arai H., et al., "The Human Endotbelin-B Receptor Gene. Structural Organization and Chromosomal Assignment," J. Biol. Chem. 268, 3463-3470, 1993.
Arima et al., "Studies on Tomaymycin, a New Antibiotic. I. Isolation and Properties of Tomaymycin," J. Antibiotics (1972) 25:437-444.
Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. (2006) 5(6):1602-1609.
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Axup et al., Proc Natl Acad Sci U S A., 2012, 109(40):16101-16106.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., Modern Pharmaceutics, Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of

(56) References Cited

OTHER PUBLICATIONS

Nonrandom Sequence Variation in Their Conserved Loop-Domains," Genomics 3, 59-66, 1988.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid is Generated by Alternative Splicing of Exon 3," J. Clin. Endocrinol. Metab. 82, 3116-3123, 1997.
Brinster et al., "Introits increase transcriptional efficiency in transgenic mice," (1988) Proc. Natl. Acad. Sci. USA 85:836-840.
Buchman and Berg "Comparison of Intron-Dependent and Intron-Independent Gene Expression," (1988) Mol. Cell Biol. 8:4395.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Cancer, 2012, http://wiki.answers.com/Q/How-many-different-types of cancer are there.
Cancer2, 2012, http://en.wikipedia.org/wiki/Management of cancer.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chem. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chang et al., "Five different anti-prostate-specific membrane antigen (PSMA) antibodies confirm PSMA expression in tumor-associated neovasculature," Cancer Research (1999) 59:3192-3198.
Chen, Z. et al., "A novel approach to the synthesis of cytotoxic C2—C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chem. 274: 24335-24341.
Cho et al., "Structure of the extracellular region of HER2 alone and in complex with the Herceptin Fab," Nature 421, 756-760, 2003.
Ciccodicola, A., et al., "Molecular characterization of a gene of the 'EGF family' expressed in undifferentiated, human NTERA2 teratocarcinoma cells," EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
ClinicalTrial, 2011, http://www.nature.com/news/2011/110928/full/477526a.html.
Collins, "Generation and initial analysis of more than 15,000 full-length human and mouse eDNA sequences," Proc Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey E. Quinn JE, Buhler KR, et al., "LuCap35: a new model of prostate cancer progression to androgen independence." The Prostate 2003;55:239-46.
Courtney, S. M. et al., "A new convenient procedure for the synthesis of pyrrolo[2,1-c] [1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use• of ATP bioluminescence as a measure of cell proliferation and cytotoxicity," (1993) J. lmmunol. Meth. 160:81-88.
Dall'Acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

(56) References Cited

OTHER PUBLICATIONS

Davis et al., "Identification of a family of Fc receptor homo logs with preferential B cell expression," (2001) Proc. Natl. Acad. Sci. USA 98(17):9772-9777.
de Groot et al., ""Cascade-Release Dendrimers" Liberate All End Groups upon a Single Triggering Event in the Dendritic Core," (2003) Angew. Chem. Int. Ed. 42:4490-4494.
de Groot et al., "Elongated Multiple Electronic Cascade and Cyclization Spacer Systems in Activatible Anticancer Prodrug for Enhanced Drug Release," (2001) J. Org. Chem. 66:8815-88 Improving the Pharmacokinetics of Proteins J Biol Chem. 277:35035-3504330.
Dennis et al., (2002) "Albumin Binding as a General Strategy for Improving the Pharmacokinetics of Proteins" J. Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. lmmunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove crosslinking pyrrolobenzodiazepine dimer," J. Antimicrob. Chemo., Aug. 2009, 64(5):949-959.
Dubowchik et al, Bioorganic & Medicinal Chemistry Letters, 8:3341-3346, (1998).
Dubowchik et al, Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation by IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The Ephrins and EPH Receptors in Neural Development," Annu. Rev. Neurosci. 21:309-345 (1998).
Foloppe, M.P. et al., "DNA-binding properties of pyrrolo[2,1-c][1,4]benzodiazephine N10—C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154
Galsky et al., "Phase 1 trial of the prostate-specific membrane antigen-directed immunoconjugate MLN2704 in patients with progressive metastatic castration-resistant prostate cancer," J. Clin. Oncol. (2008) 26:2147-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A Novel Transiently Expressed, Integral Membrane Protein Linked to Cell Activation. Molecular Cloning via the Rapid Degradation Signal Auuua," (1992) J. Biol. Chem. 267 (16):11267-11273.
Gavezzotti, A., "Are crystal structures predictable?" Acc. Chem. Res. (1994) 27:309-314.
Geiser et al "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AAA60209.1 (1993).
Genbank accession No. AB040878 (2001).
Genbank accession No. AF116456 (1999).
Genbank accession No. AF179274 (2001).

(56) References Cited

OTHER PUBLICATIONS

Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. M99487.1 (1993).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP_001194 (2013).
Genbank accession No. NP_001774.10 (2013).
Genbank accession No. NP_003203 (2013).
Genbank accession No. NP 002111.1 (2013).
Genbank accession No. NP_001707.1 (2013).
Genbank accession No. NP_001773.1 (2013).
Genbank accession No. NP_002552.2 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, A Proteogl Ycan Identified in Prostate Cancer That Is Associated With Disease Progression and Androgen Independence," (2001) Int J Cancer. Oct. 15; 94(2): 178-184.
Gordon et al., "Somatic hypermutation of the B cell receptor genes 829 (1gf3, CD79b) and mb1 (lga, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 23-200, 503-549, 633-647.

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2—C3/C2'—C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C—C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular Cloning and Expression Pattern of a Human Gene Homologous to the Murine mb-1 Gene," (1992) J. lmmunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc Pharmacal. 20, s1-S4, 1992.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Hara et al., "DC 102, a new glycosidic pyrrolo(1,4)benzodiazepine antibiotic produced by *Streptomyces* sp.", J. Antibiotics, 41, 702-704 (1988).
Hartley J A: "The development of pyrrolobenzodiazepines as antitumour agents", Expert Opinion on Investigational Drugs, Ashley Publications Ltd., vol. 28, No. 6, Jan. 1, 2011, pp. 733-744.

(56) References Cited

OTHER PUBLICATIONS

Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (1g-alpha/mb-1) gene," (1994) Immunogenetics 40(4 ):287-295.
Hay et al., "A 2-Nitroimidazole Carbamate Prodrug of 5-Amino-1-(Chloromethyl)-3-[(5,6,7-Trimethoxyindol-2-Yl)Carbonyl]-1,2-Dihydr0-3H-Benz[E]Indole (Amino-SECO-CBI-TMI) for Use With ADEPT and GDEPT," (1999) Bioorg. Med. Chem. Lett. 9:2237-2242.
Henry et al., "A prostate-specific membrane antigen-targeted monoclonal antibody-chemotherapeutic conjugate designed for the teratment of prostate cancer," Cancer Res. (2004) 64:7995-8001.
Herdwijn et al., "Synthesis of trans(+ )6-phenoxyacetamido-l-methylene-3,3-dicarboxymethyl-1-cathapenam," Canadian Journal of Chemistry. 1982, 60, 2903-2907.
Hermanson, G.T., "Heterobifunctional Cross-linkers," (1996) Bioconjugate Techniques; Academic Press: New York, p. 234-242.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)," Eur. J. Hum. Genet. 5, 180-185, 1997.
Hofstra R.M.W., et al., "Mutations in Hirschsprung Disease: When Does a Mutation Contribute to the Phenotype," Nat. Genet. 12, 445-447, 1996.
Horie et al., "Identification and Characterization of TMEFF2, a Novel Surviv Factor for Hippocampal and Mesencephalic Neurons," (2000) Genornics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1- c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.

Hurley, L. and Needham-Vandevanier, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Itoh et al., "Sibanomicin, a new pyrrolo(1,4)benzodiazepine antitumor antibiotic produced by a *micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey et al., Bioconjugate Chemistry, 5, 2006, 17, 831-840.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine, " Nature Reviews: Drug Discovery (2003) 2:205-213.
Junutula et al., "Rapid identification of reactive cysteine residues for site-specific labeling of antibody-Fabs," (2008) Jour of lmmun. Methods 332:41-52.
Junutula, et al., "Site-specific conjugation of a cytotoxic drug to an antibody improves the therapeutic index," 2008 Nature Biotech., 26(8):925-932.
Kamal et al., "Synthesis and DNA-binding affinity of A-C8/C-C2 alkoxyamido-linked pyrrolo[2,1c][1,4]benzodiazepine dimers" Biorg. Med. Chem. Lett. (2003) 13(22):3955-3958.
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A. "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo[2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

(56) References Cited

OTHER PUBLICATIONS

Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1688-1689.
Kasahara et al., "Nucleotide sequence of a chimpanzee DOB cDNA clone," (1989) Immunogenetics 30(1):66-68.
King et al., "Facile synthesis of maleimide bifunctional linkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor cDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin•6," (1999) Brit. Jour. Cancer 79(5-6):707-717.
Lambert J., "Drug-conjugated monoclonal antibodies for the treatment of cancer," (2005) Current Opin. in Pharmacol. 5:543-549.
Langley, D.R. and Thurston, D.E., "A versatile and efficient synthesis of cathinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and cDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).

Leimgruber, W. et al., "Total synthesis of anthramycin," J. Am. Chem. Soc., 90, 5641-5643 (1968).
Levenson et al., "MCF-7: The First Hormone-responsive Breast Cancer Cell Line," (1997) Cancer Res. 57(15):3071-3078.
Liang et al., "The Gene for a Novel Transmembrane Protein Containing Epidermal Growth Factor and Follistatin Domains is Frequently Hypermethylated in Human Tumor Cells," (2000) Cancer Res. 60:4907-4912.
Liu et al., "Constitutive and antibody-induced internalization of prostate-specific membrane antigen," Cancer Res. 1998) 58:4-55-4060.
Liu et al., "Monoclonal antibodies to the extracellular domain of prostate-specific membrane antigen also react with tumor vascular endothelium," Cancer Res. (1997) 57:3629-3634.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mastroberardino et al., "Amino-acid transport by heterodimers of 4F2hc/CD98 and members of a permease family," Nature 395 (6699):288-291 (1998).
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," , (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Milowsky et al., "Phase I trial of Yttrium-90-labeled anti-prostate-spedcific membrane antigen monoclonal antibody 1591 for androgen-independent prostate cancer," J. Clin. Oncol. (2004) 22:2522-2531.
Milowsky et al., "Vascular targeted therapy with anti-prostate-specific membrane antigen monoclonal antibody 1591 in advanced solid tumors," J. Clin. Oncol. (2007) 25:540-547.
Miura et al., "RP1OS is Associated With MD-1 and Transmits an Activation Signal in Human B Cells," (1996) Genomics 38(3):299-304.
Miura et al., "RP1OS is Associated With MD-1 and Transmits an Activation Signal in Human B Cells," (1998) Blood 92:2815-2822.
Moore M., et al., "Molecular cloning of the cDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morris et al., "Phase I evaluation of J591 as a vascular targeting agent in progressive solid tumors," Clin. Cancer Res. (2007) 13(9).
Morrison et al., "Chimeric human antibody molecules: Mouse antigen-binding domains with human constant region domains," (1984) Proc. Natl. Acad. Sci. USA, 81:6851-6855.

(56) References Cited

OTHER PUBLICATIONS

Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. lmmunol. 22 (6): 1621-1625.
Mungall A.J., et al., "The DNA sequence and analysis of human chromosome 6," Nature 425, 805-811, 2003.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2): 143-150.
Nakamuta M., et al., "Cloning and Sequence Analysis of a cDNA Encoding Human Non-Selective Type of Endothelin Receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastmnd cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin 01: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.
O'Neil, Chemical Abstract No. 171573p, "The synthesis of Functionalized Pyrrolo[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human EndothelinB," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Payne, G. "Progress in immunoconjugate cancer therapeutics," (2003) Cancer Cell 3:207-212.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'homme et al., "Structure and expression of the mb-1 transcript in human lymphoid cells," (1992) Clin. Exp. lmmunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., ""Conformations of complexes between pyrrolo[1,4]benzodiazepines and DNA segments,"" J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.

(56) References Cited

OTHER PUBLICATIONS

Ross et al., "Prostate Stem Cell Antigen as Therapy Target: Tissue Expression and in Vivo Efficacy of an Immunoconjugate," (2002) Cancer Res. 62:2546-2553.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-Iike structural properties," (1988) EMBO J. 7(11):3457-3464.
Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A. 82, 6497-6501, 1985.
Servenius et al., "Class II Genes of the Human Major Histocompatibility Complex, The DOBeta Gene is a Divergent Member of the Class II P Gene Family," (1987) J. Biol. Chem. 262:8759-8766.
Shamis et al., "Bioactivation of Self-lmmolative Dendritic Prodrugs by Catalytic Antibody 38C2," (2004) J. Am. Chem. Soc. 126:1726-1731.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu et al., "Prothracarcin, a novel antitumor antibiotic," The Journal of Antibiotics (1982) 29, 2492-2503.
Shimizu, K et al., "Prothracarcin, a Novel Antitumor Antibiotic," J Antibiotics, 35, 972-978 (1982).
Sinha S.K., et al., "Characterization of the EBV /C3d Receptor on the Human Jurkat T Cell Line: Evidence for a Novel Transcript," (1993) J.lmmunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., Anal. Biochem., 1985, 150(1): 76-85.
Souillac, P. et al., "Chracterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model-facilitating anti-cancer preclinical pharmacodynamics and improving animal welfare," Int. J. Oncol. (2006) 29(6):1493-1499.

Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Tawaragi Y., et al., "Primary Structure of Nonspecific Crossreacting Antigen (NCA), A Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson, J.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Biorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs,"(2002) J. Org. Chem. 67:1866-1872.
Tonnelle et al., "DOBeta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a

(56) References Cited

OTHER PUBLICATIONS 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer lmmunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a Human Protein Homologous to the Mouse Lyb-2 B Cell Differentiation Antigen and Sequence of the Corresponding cDNA," (1990) J. lmmunol. 144(12):4870-4877.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the Human B Lymphocyte Receptor for C3d and the Epstein-Barr Virus and Relatedness to Other Members of the Family of C3/C4 Binding Proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wilkinson, "Eph Receptors and Ephrins: Regulators of Guidance and Assembly," Int. Rev. Cytol. 196:177-244.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42:4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for The welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody-drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na +—Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).
Yamamoto T., et al., "Similarity of protein encoded by the human c-erb-B-2 gene to epidermal growth factor receptor," Nature 319, 230-234, 1986.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Yu et al., "Human mb-1 Gene: Complete eDNA Sequence and Its Expression in B Cells Bearing Membrane Ig of Various Isotypes," (1992) J. lmmunol. 148(2) 633-637.
International Search Report for Application No. PCT/GB2014/053051 dated Feb. 4, 2015 (3 pages).
Written Opinion for Application No. PCT/GB2014/053051 dated Feb. 4, 2015 (4 pages).
U.S. Appl. No. 14/346,006, filed Mar. 20, 2014, Howard et al.
U.S. Appl. No. 14/397,842, filed Oct. 29, 2014, Howard et al.
U.S. Appl. No. 14/397,843, filed Oct. 29, 2014, Howard et al.
U.S. Appl. No. 14/579,094, filed Dec. 22, 2014, Howard et al.
U.S. Appl. No. 62/051,387, filed Sep. 17, 2014, Flygare et al.

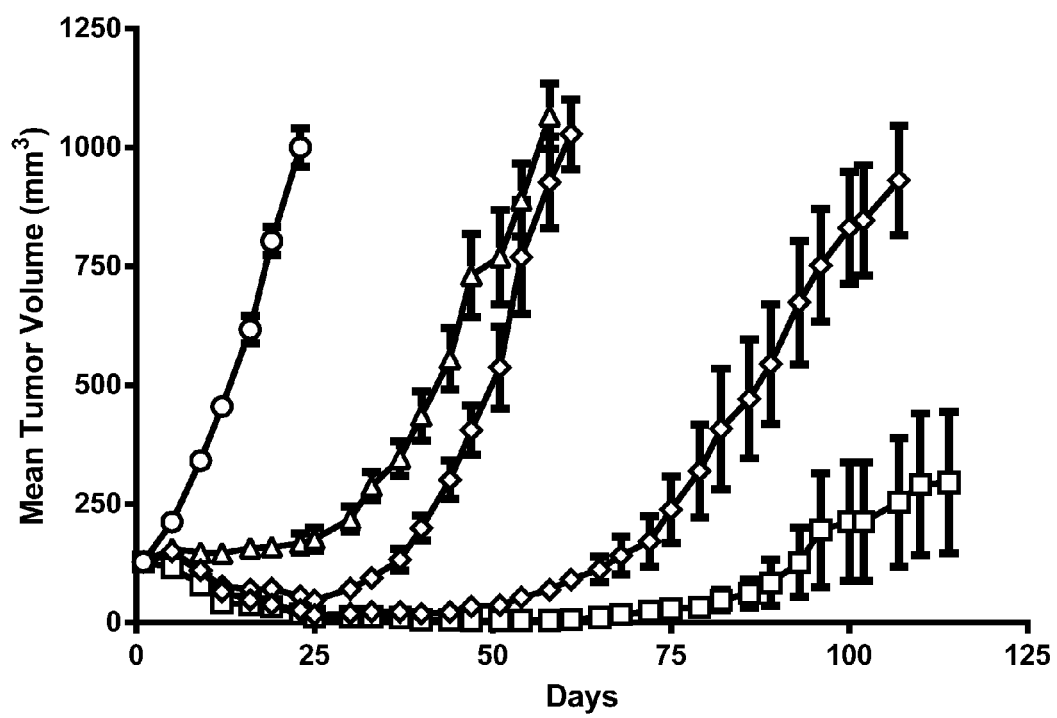

PYRROLOBENZODIAZEPINE-ANTIBODY CONJUGATES

The present invention relates to pyrrolobenzodiazepines (PBDs) having a labile protecting group in the form of a linker to an antibody.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

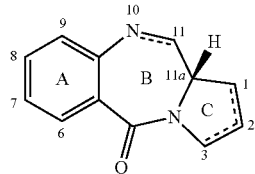

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

One pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

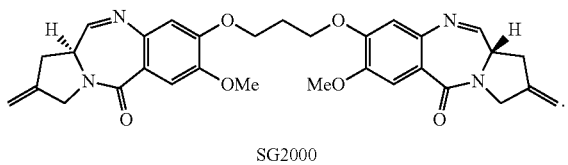

SG2000

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, have been described in WO 2011/130613 and WO 2011/130616. The linker in these compounds is attached to the PBD core via the C2 position, and are generally cleaved by action of an enzyme on the linker group. In WO 2011/130598, the linker in these compounds is attached to one of the available N10 positions on the PBD core, and are generally cleaved by action of an enzyme on the linker group.

Antibody-drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6): 3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) *Blood* 114(13):2721-2729; U.S. Pat. No. 7,521,541; U.S. Pat. No. 7,723,485; WO2009/052249; McDonagh (2006) Protein Eng. Design & Sel. 19(7): 299-307; Doronina et al (2006) Bioconj. Chem. 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

The present inventors have developed particular PBD dimer antibody conjugates.

SUMMARY OF THE INVENTION

A first aspect of the present invention provides a conjugate of formula ConjA:

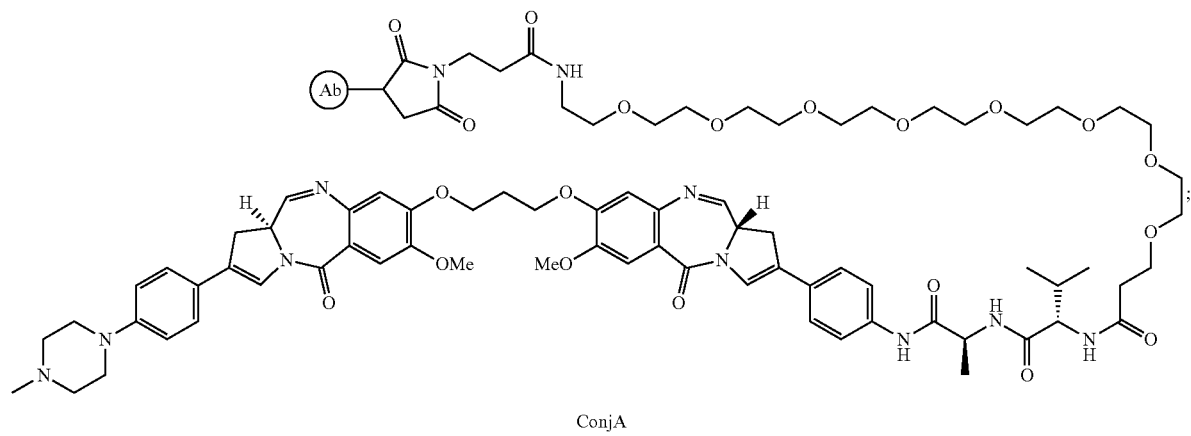
ConjA
ConjB:
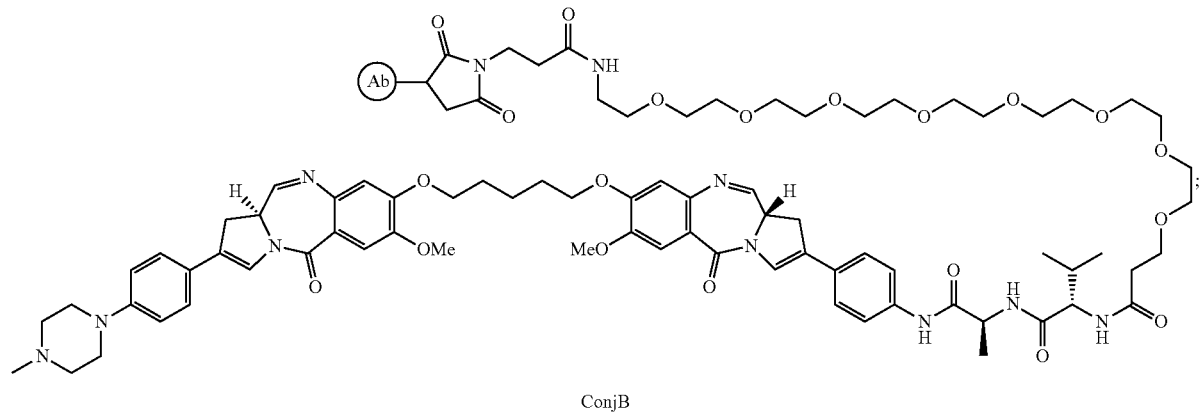
ConjB
ConjC
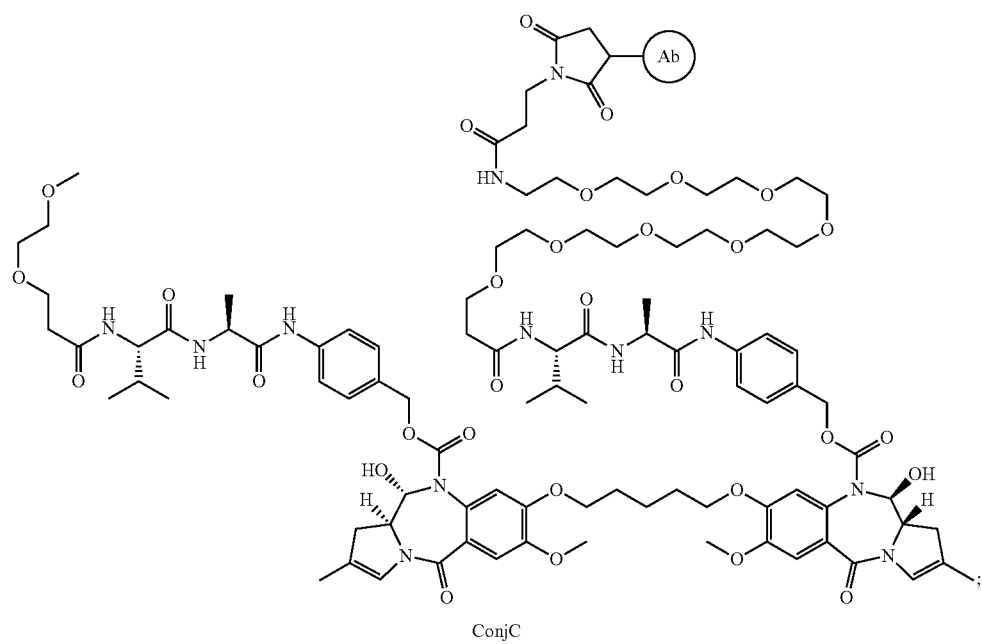
ConjC or
ConjDE:
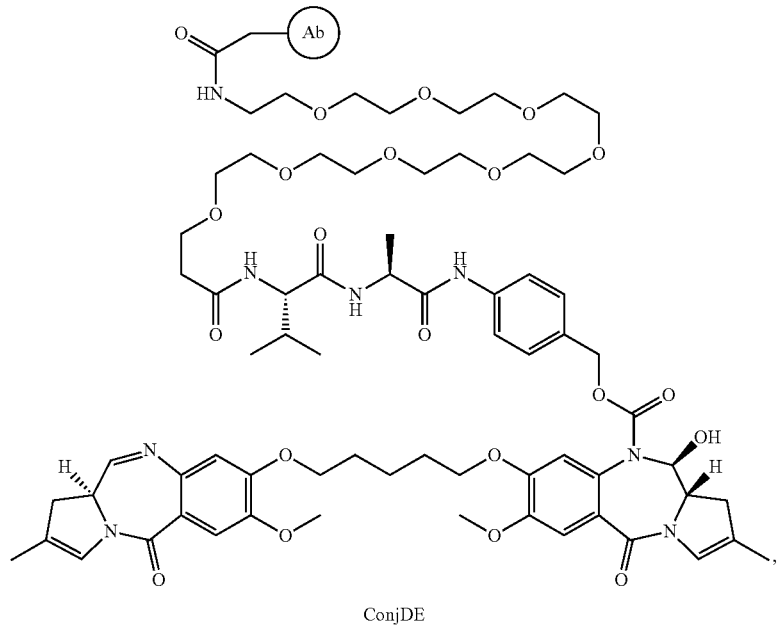
ConjDE
where Ab represents an antibody as defined below. The link to the moiety shown is via a free S (active thiol) on the cell binding agent.
A second aspect of the invention provides a method of making a conjugate according to the first aspect of the invention comprising conjugating a compound which is selected from A:
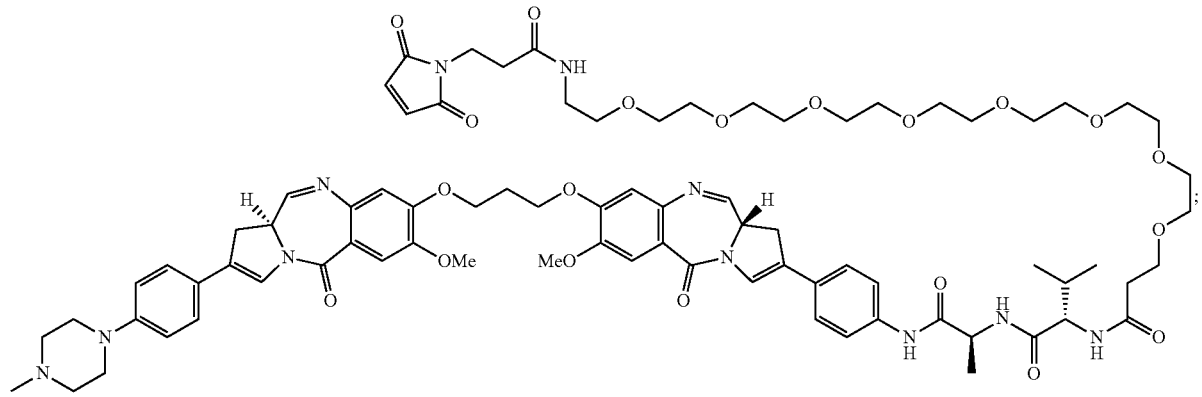
A, 20

B:
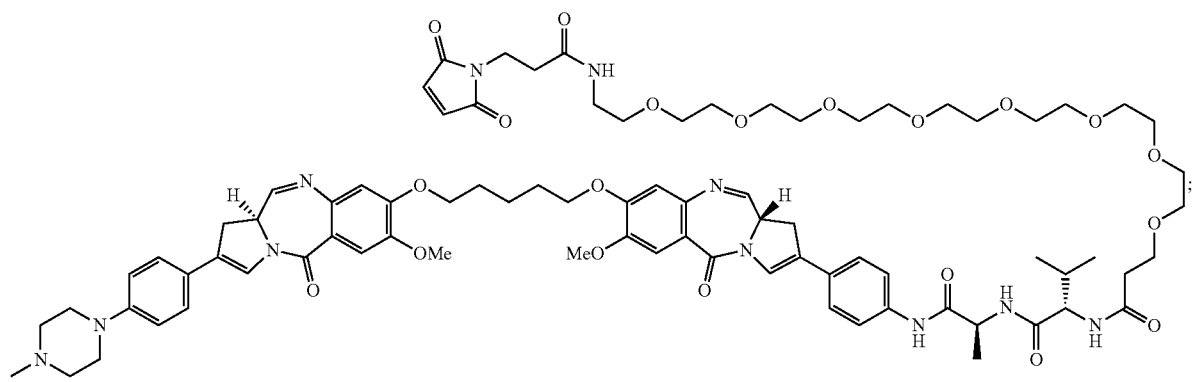
B, 26
C:
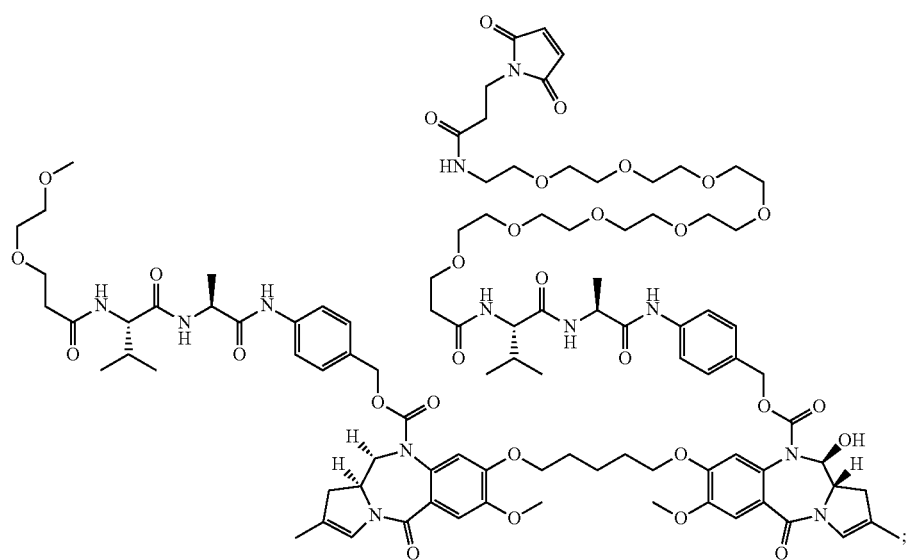
C, 43
D:
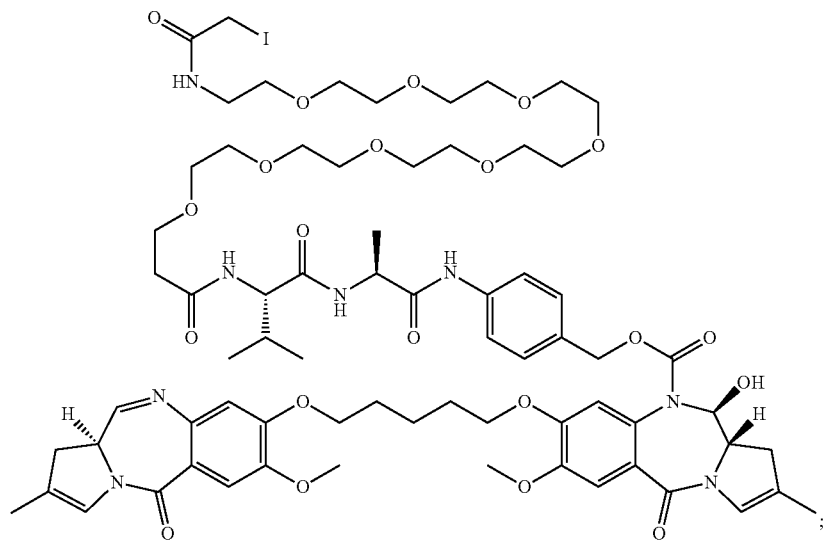
D and
E:

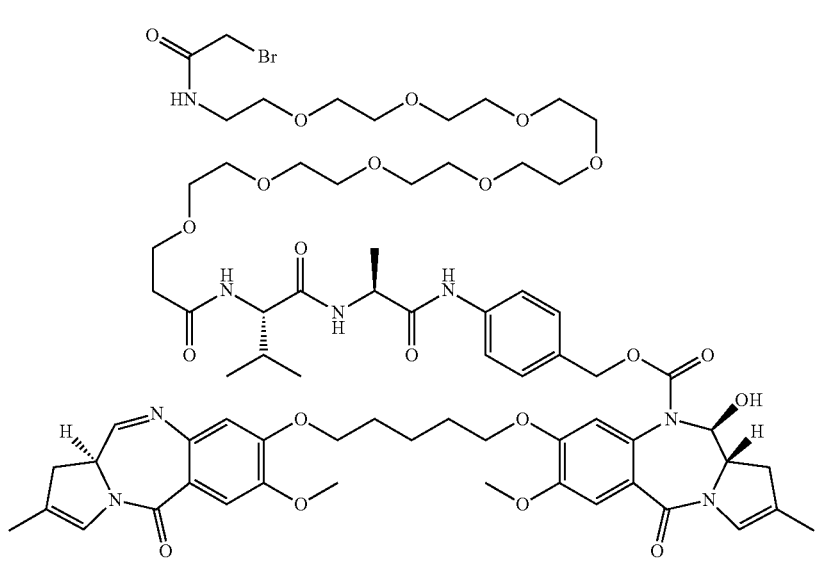

with an antibody as defined below.

WO 2010/043380 and WO 2011/130613 disclose compound 30:

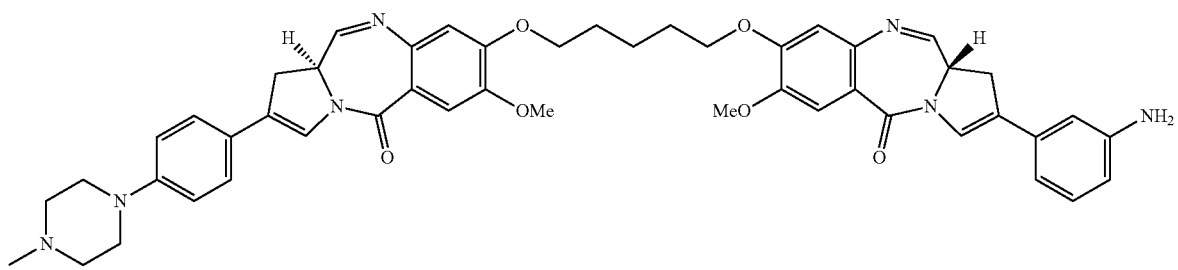

WO 2011/130613 also discloses compound 51:

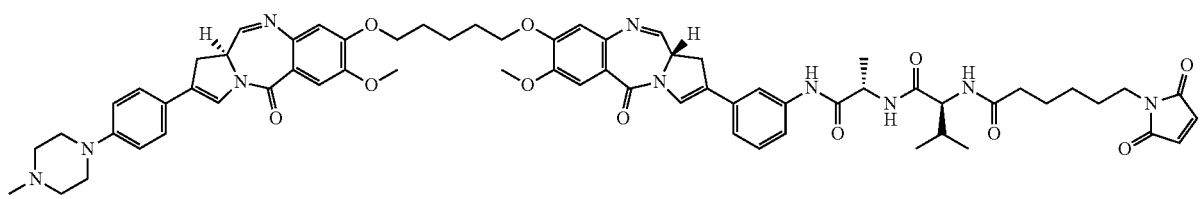

Compound A differs from compound 30 by only having a (CH$_2$)$_3$ tether between the PBD moieties, instead of a (CH$_2$)$_5$ tether, which reduces the lipophilicity of the released PBD dimer. The linking group in both Compounds A and B is attached to the C2-phenyl group in the para rather than meta position.

Compounds C, D and E differ from previously disclosed PBD dimers with a drug linker having a C2-3 endo-double bond, by having a smaller, less lipophilic C2 substituent, e.g. 4F-phenyl, propylene. As such, the conjugates of compounds C, D and E are less likely to aggregate once synthesised. Such aggregation of conjugates can be measured by Size exclusion chromatography (SEC).

Compound C has a cleavable protecting group on the second imine group which avoids cross-reactions during its synthesis and in the final product avoids the formation of carbinolamine and carbinolamine methyl ethers. This protection also avoids the presence of a reactive imine group in the molecule.

Compounds D and E comprise an iodoacetamide and bormoacetamide groups respectively for linking to the cell binding agent.

All five compounds have two $sp^2$ centres in each C-ring, which may allow for stronger binding in the minor groove of DNA, than for compounds with only one $sp^2$ centre in each C-ring.

DETAILED DESCRIPTION OF THE INVENTION

The present invention provides a PBD dimer with a linker connected through the C2 or N10 position on one of the PBD moieties conjugated to an antibody as defined below.

The present invention is suitable for use in providing a PBD compound to a preferred site in a subject. The conjugate allows the release of an active PBD compound that does not retain any part of the linker. There is no stub present that could affect the reactivity of the PBD compound. Thus ConjA would release the compound RelA:

The specified link between the PBD dimer and the cell binding agent, e.g. antibody, in the present invention is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targetted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA, RelB, or RelC is achieved at the desired activation site of the conjugates of formulae ConjA, ConjB, ConjC or ConjDE by the

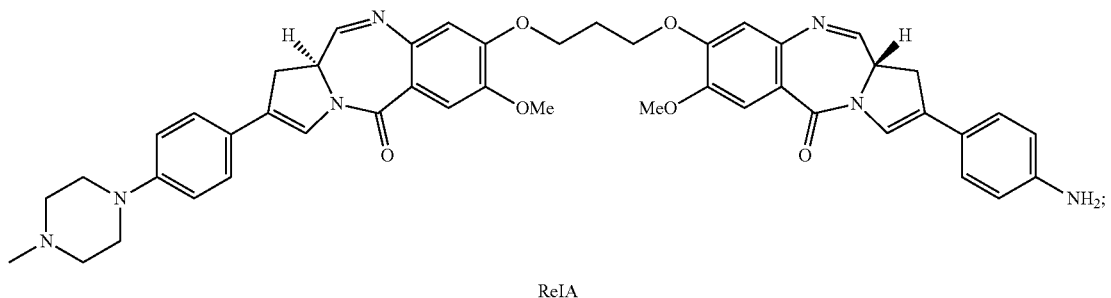 [SMILES: COc1cc2c(cc1OCCCOc1cc3c(cc1OC)C(=O)N1C=C(c4ccc(N5CCN(C)CC5)cc4)C[C@H]1C=N3)N=C[C@@H]1CC(c3ccc(N)cc3)=CN1C2=O ; "ReIA"]

RelA

ConjB would release the compound RelB:

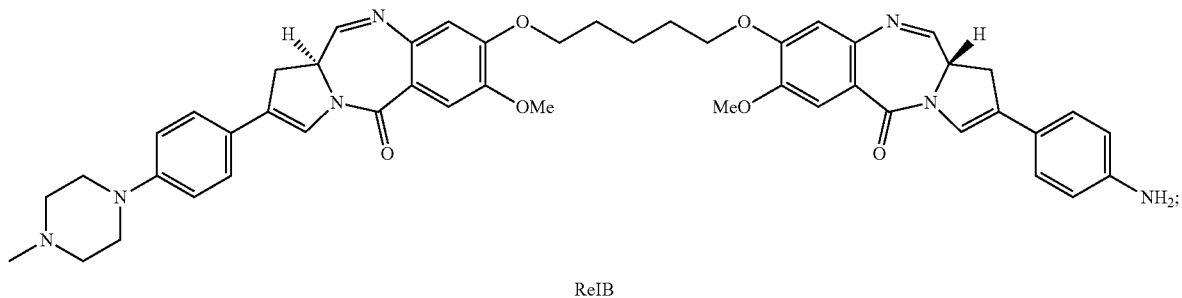 [SMILES: COc1cc2c(cc1OCCCCCOc1cc3c(cc1OC)C(=O)N1C=C(c4ccc(N5CCN(C)CC5)cc4)C[C@H]1C=N3)N=C[C@@H]1CC(c3ccc(N)cc3)=CN1C2=O ; "ReIB"]

RelB and

ConjC and ConjDE would release the compound RelC:

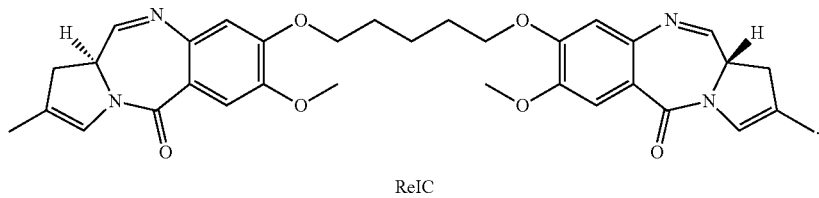

RelC action of an enzyme, such as cathepsin, on the linking group, and in particular on the valine-alanine dipeptide moiety.

Antibody

In one aspect the antibody is in one aspect the antibody is an antibody that binds to PSMA, the antibody comprising a VH domain having the sequence according to any one of SEQ ID NOs. 1, 3, 5, 7, 8, 9, or 10.

The antibody may further comprise a VL domain. In some embodiments the antibody further comprises a VL domain having the sequence according to any one of SEQ ID NOs. 2, 4, 6, 11, 12, 13, 14, 15, 16, 17, or 18.

In some embodiments the antibody comprises a VH domain paired with a VL domain, the VH and VL domains having sequences selected from the group consisting of:

SEQ ID NO. 1 paired with any one of SEQ ID NOs. 2, 4, 6, 11, 12, 13, 14, 15, 16, 17, or 18;

SEQ ID NO. 3 paired with any one of SEQ ID NOs. 2, 4, 6, 11, 12, 13, 14, 15, 16, 17, or 18;

SEQ ID NO. 5 paired with any one of SEQ ID NOs. 2, 4, 6, 11, 12, 13, 14, 15, 16, 17, or 18;

SEQ ID NO. 7 paired with any one of SEQ ID NOs. 2, 4, 6, 11, 12, 13, 14, 15, 16, 17, or 18; SEQ ID NO. 8 paired with any one of SEQ ID NOs. 2, 4, 6, 11, 12, 13, 14, 15, 16, 17, or 18;

SEQ ID NO. 9 paired with any one of SEQ ID NOs. 2, 4, 6, 11, 12, 13, 14, 15, 16, 17, or 18; or SEQ ID NO. 10 paired with any one of SEQ ID NOs. 2, 4, 6, 11, 12, 13, 14, 15, 16, 17, or 18. For example SEQ ID NO. 1 paired with SEQ ID NO. 2, SEQ ID NO. 3 paired with SEQ ID NO. 4, SEQ ID NO. 5 paired with SEQ ID NO. 6, SEQ ID NO. 7 paired with SEQ ID NO. 11, SEQ ID NO. 7 paired with SEQ ID NO. 12, SEQ ID NO. 7 paired with SEQ ID NO. 13, SEQ ID NO. 7 paired with SEQ ID NO. 14, SEQ ID NO. 7 paired with SEQ ID NO. 15, SEQ ID NO. 7 paired with SEQ ID NO. 16, SEQ ID NO. 7 paired with SEQ ID NO. 17, SEQ ID NO. 7 paired with SEQ ID NO. 18, SEQ ID NO. 8 paired with SEQ ID NO. 11, SEQ ID NO. 8 paired with SEQ ID NO. 12, SEQ ID NO. 8 paired with SEQ ID NO. 13, SEQ ID NO. 8 paired with SEQ ID NO. 14, SEQ ID NO. 8 paired with SEQ ID NO. 15, SEQ ID NO. 8 paired with SEQ ID NO. 16, SEQ ID NO. 8 paired with SEQ ID NO. 17, SEQ ID NO. 8 paired with SEQ ID NO. 18, SEQ ID NO. 9 paired with SEQ ID NO. 11, SEQ ID NO. 9 paired with SEQ ID NO. 12, SEQ ID NO. 9 paired with SEQ ID NO. 13, SEQ ID NO. 9 paired with SEQ ID NO. 14, SEQ ID NO. 9 paired with SEQ ID NO. 15, SEQ ID NO. 9 paired with SEQ ID NO. 16, SEQ ID NO. 9 paired with SEQ ID NO. 17, SEQ ID NO. 9 paired with SEQ ID NO. 18, SEQ ID NO. 10 paired with SEQ ID NO. 11, SEQ ID NO. 10 paired with SEQ ID NO. 12, SEQ ID NO. 10 paired with SEQ ID NO. 13, SEQ ID NO. 10 paired with SEQ ID NO. 14, SEQ ID NO. 10 paired with SEQ ID NO. 15, SEQ ID NO. 10 paired with SEQ ID NO. 16, SEQ ID NO. 10 paired with SEQ ID NO. 17, or SEQ ID NO. 10 paired with SEQ ID NO. 18.

The VH and VL domain(s) may pair so as to form an antibody antigen binding site that binds PSMA.

In some embodiments the antibody is an intact antibody comprising a VH domain paired with a VL domain, the VH and VL domains having sequences selected from the group consisting of:

SEQ ID NO. 1 paired with any one of SEQ ID NOs. 2, 4, 6, 11, 12, 13, 14, 15, 16, 17, or 18;

SEQ ID NO. 3 paired with any one of SEQ ID NOs. 2, 4, 6, 11, 12, 13, 14, 15, 16, 17, or 18;

SEQ ID NO. 5 paired with any one of SEQ ID NOs. 2, 4, 6, 11, 12, 13, 14, 15, 16, 17, or 18;

SEQ ID NO. 7 paired with any one of SEQ ID NOs. 2, 4, 6, 11, 12, 13, 14, 15, 16, 17, or 18;

SEQ ID NO. 8 paired with any one of SEQ ID NOs. 2, 4, 6, 11, 12, 13, 14, 15, 16, 17, or 18;

SEQ ID NO. 9 paired with any one of SEQ ID NOs. 2, 4, 6, 11, 12, 13, 14, 15, 16, 17, or 18; or SEQ ID NO. 10 paired with any one of SEQ ID NOs. 2, 4, 6, 11, 12, 13, 14, 15, 16, 17, or 18. For example SEQ ID NO. 1 paired with SEQ ID NO. 2, SEQ ID NO. 3 paired with SEQ ID NO. 4, SEQ ID NO. 5 paired with SEQ ID NO. 6, SEQ ID NO. 7 paired with SEQ ID NO. 11, SEQ ID NO. 7 paired with SEQ ID NO. 12, SEQ ID NO. 7 paired with SEQ ID NO. 13, SEQ ID NO. 7 paired with SEQ ID NO. 14, SEQ ID NO. 7 paired with SEQ ID NO. 15, SEQ ID NO. 7 paired with SEQ ID NO. 16, SEQ ID NO. 7 paired with SEQ ID NO. 17, SEQ ID NO. 7 paired with SEQ ID NO. 18, SEQ ID NO. 8 paired with SEQ ID NO. 11, SEQ ID NO. 8 paired with SEQ ID NO. 12, SEQ ID NO. 8 paired with SEQ ID NO. 13, SEQ ID NO. 8 paired with SEQ ID NO. 14, SEQ ID NO. 8 paired with SEQ ID NO. 15, SEQ ID NO. 8 paired with SEQ ID NO. 16, SEQ ID NO. 8 paired with SEQ ID NO. 17, SEQ ID NO. 8 paired with SEQ ID NO. 18, SEQ ID NO. 9 paired with SEQ ID NO. 11, SEQ ID NO. 9 paired with SEQ ID NO. 12, SEQ ID NO. 9 paired with SEQ ID NO. 13, SEQ ID NO. 9 paired with SEQ ID NO. 14, SEQ ID NO. 9 paired with SEQ ID NO. 15, SEQ ID NO. 9 paired with SEQ ID NO. 16, SEQ ID NO. 9 paired with SEQ ID NO. 17, SEQ ID NO. 9 paired with SEQ ID NO. 18, SEQ ID NO. 10 paired with SEQ ID NO. 11, SEQ ID NO. 10 paired with SEQ ID NO. 12, SEQ ID NO. 10 paired with SEQ ID NO. 13, SEQ ID NO. 10 paired with SEQ ID NO. 14, SEQ ID NO. 10 paired with SEQ ID NO. 15, SEQ ID NO. 10 paired with SEQ ID NO. 16, SEQ ID NO. 10 paired with SEQ ID NO. 17, or SEQ ID NO. 10 paired with SEQ ID NO. 18.

In some embodiments, the antibody competes with the antibody secreted by hybridoma ATCC accession No. HB-12126 for binding to PSMA. In another aspect, the antibody competes with the antibody secreted by hybridoma ATCC accession No. HB-12109 for binding to PSMA. In one embodiment the antibody binds PSMA with an association constant ($K_a$) no less than 2, 5 or 10-fold less than the antibody secreted by the hybridoma.

In one aspect the antibody is the antibody secreted by a hydridoma. In one embodiment the hybridoma is ATCC accession No. HB-12126. In another embodiment the hybridoma is ATCC accession No. HB-12109.

In some embodiments the antibody is the J415 antibody disclosed in WO02/098897.

In some embodiments the antibody is the J519 antibody disclosed in WO02/098897.

In aspect the antibody is an antibody as described herein which has been modified (or further modified) as described below. In some embodiments the antibody is a humanised, deimmunised or resurfaced version of an antibody disclosed herein. For example, a humanised, deimmunised or resurfaced version of (i) the antibody comprising the VH domain SEQ ID NO. 1 paired with the VL domain SEQ ID NO. 2, (ii) the J519 antibody disclosed in WO02/098897, (iii) the antibody secreted by the hybridoma ATCC accession No. HB-12109, (iv) the antibody comprising the VH domain SEQ ID NO. 5 paired with the VL domain SEQ ID NO. 6, (v) the J415 antibody disclosed in WO02/098897, (vi) the antibody secreted by the hybridoma ATCC accession No. HB-12126.

Terminology

The term "antibody" herein is used in the broadest sense and specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind PSMA (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1 m1 [that, is any allotype other than G1 m1], G1m17, G2m23, G3m21, G3m28, G3m11, G3m5, G3m13, G3m14, G3m10, G3m15, G3m16, G3m6, G3m24, G3m26, G3m27, A2 m1, A2m2, Km1, Km2 and Km3) of immunoglobulin molecule. The immunoglobulins can be derived from any species, including human, murine, or rabbit origin.

As used herein, "binds PSMA" is used to mean the antibody binds PSMA with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds PSMA with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the invention can bind PSMA with a high affinity. For example, in some embodiments the antibody can bind PSMA with a $K_D$ equal to or less than about $10^{-6}$ M, such as $1 \times 10^{-6}$, $10^{-7}$, $10^{-5}$, $10^{-9}$, $10^{-10}$, $10^{-11}$, $10^{-12}$, $10^{-13}$ or $10^{-14}$.

As used herein, PSMA refers to Prostate-Specific Membrane Antigen. In one embodiment, PSMA polypeptide corresponds to Genbank accession no. AAA60209, version no. AAA60209.1 GI:190664, record update date: Jun. 23, 2010 08:48 AM. In one embodiment, the nucleic acid encoding PSMA polypeptide corresponds to Genbank accession no. M99487, version no. M99487.1 GI:190663, record update date: Jun. 23, 2010 08:48 AM. "Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA*, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Modification of Antibodies

The antibodies disclosed herein may be modified. For example, tomake them less immunogenic to a human subject. This may be achieved using any of a number of techniques familiar to the person skilled in the art. Some of these techniques are described in more detail below.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:

(a) determining the conformational structure of the variable region of the non-human (e.g. rodent) antibody (or fragment thereof) by constructing a three-dimensional model of the non-human antibody variable region;

(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;

(c) defining for the non-human antibody to be humanized, a set of heavy and light chain surface exposed amino acid residues using the set of framework positions generated in step (b);

(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;

(e) substituting, in the amino acid sequence of the non-human antibody to be humanized, the set of heavy and light chain surface exposed amino acid residues defined in step (c) with the set of heavy and light chain surface exposed amino acid residues identified in step (d);

(f) constructing a three-dimensional model of the variable region of the non-human antibody resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and (h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Embodiments

Embodiments of the present invention include ConjA wherein the antibody is as defined above.

Embodiments of the present invention include ConjB wherein the antibody is as defined above.

Embodiments of the present invention include ConjC wherein the antibody is as defined above.

Drug Loading

The drug loading is the average number of PBD drugs per antibody, e.g. antibody. Where the compounds of the invention are bound to cysteines, drug loading may range from 1 to 8 drugs ($D^L$) per antibody, i.e. where 1, 2, 3, 4, 5, 6, 7, and 8 drug moieties are covalently attached to the antibody. Compositions of conjugates include collections of antibodies, conjugated with a range of drugs, from 1 to 8. Where the compounds of the invention are bound to lysines, drug loading may range from 1 to 80 drugs ($D^L$) per antibody, although an upper limit of 40, 20, 10 or 8 may be preferred. Compositions of conjugates include collections of antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p >5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. No. 7,521,541; U.S. Pat. No. 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Alternatively, site-specific conjugation can be achieved by engineering antibodies to contain unnatural amino acids in their heavy and/or light chains as described by Axup et al. ((2012), Proc Natl Acad Sci USA. 109(40):16101-16116). The unnatural amino acids provide the additional advantage that orthogonal chemistry can be designed to attach the linker reagent and drug.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 20. In some embodiments the range is selected from 1 to 8, 2 to 8, 2 to 6, 2 to 4, and 4 to 8.

In some embodiments, there is one dimer pyrrolobenzodiazepine group per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^AOH$, where $R^A$ is $C_{1-4}$ alkyl):

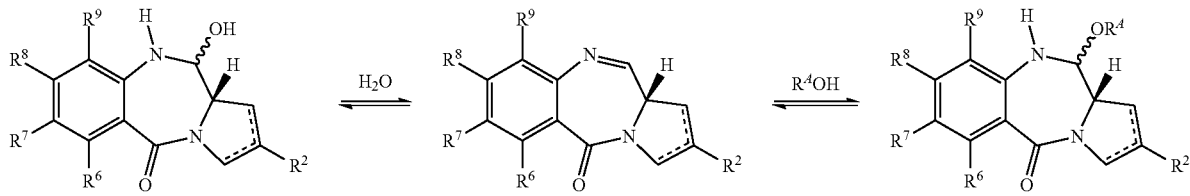

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

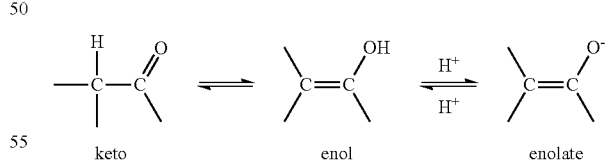

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity
In Vitro Cell Proliferation Assays

Generally, the cytotoxic or cytostatic activity of an antibody-drug conjugate (ADC) is measured by: exposing mammalian cells having receptor proteins to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of *Coleoptera* luciferase (U.S. Pat. Nos. 5,583,024; 5,674,713 and 5,700, 670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 μl per well) into black 96 well plates. Plates of adherent cell lines are incubated overnight to allow adherence. Suspension cell cultures can be used on the day of seeding.

A stock solution (1 ml) of ADC (20 μg/ml) is made in the appropriate cell culture medium. Serial 10-fold dilutions of stock ADC are made in 15 ml centrifuge tubes by serially transferring 100 μl to 900 μl of cell culture medium.

Four replicate wells of each ADC dilution (100 μl) are dispensed in 96-well black plates, previously plated with cell suspension (100 μl), resulting in a final volume of 200 μl. Control wells receive cell culture medium (100 μl).

If the doubling time of the cell line is greater than 30 hours, ADC incubation is for 5 days, otherwise a four day incubation is done.

At the end of the incubation period, cell viability is assessed with the Alamar blue assay. AlamarBlue (Invitrogen) is dispensed over the whole plate (20 μl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

Use

The conjugates of the invention may be used to provide a PBD compound at a target location.

The target location is preferably a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound RelA, RelB, or RelC. Thus, the conjugate may be used to selectively provide a compound RelA, RelB or RelC to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Cancers of particular interest include, but are not limited to, prostate cancers.

PSMA has also shown to be widely expressed in the neovasculature of non-prostate solid tumors including carcinomas of the colon, breast, bladder, pancreas, kidney and melanoma, but not normal vasculature. Thus, a PSMA specific ADC can be used for the treatment of non-prostate tumors with PSMA positive neovasculature.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CBI-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug Conjugates

Antibody drug conjugates may be prepared by several routes, employing organic chemistry reactions, conditions, and reagents known to those skilled in the art, including reaction of a nucleophilic group of an antibody with a drug-linker reagent. This method may be employed to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

BRIEF DESCRIPTION OF THE DRAWING

FIG. 1 shows shows the effect on mean tumour volume in groups of 10 miced dosed with two different conjugates of the invention.

EXAMPLES

General Experimental Methods

Reaction progress was monitored by thin-layer chromatography (TLC) using Merck Kieselgel 60 F254 silica gel, with fluorescent indicator on aluminium plates. Visualisation of TLC was achieved with UV light or iodine vapour unless otherwise stated. Flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH.

$^1$H and $^{13}$C NMR spectra were obtained on a Bruker Avance 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), q (quartet), p (pentuplet) and m (multiplet). IR spectra were recorded on a Perkin-Elmer FT/IR paragon 1000 spectrophotometer by application of the sample in a solution of chloroform using the ATR "golden gate" system. Optical rotations were measured at ambient temperature using a Bellingham and Stanley ADP 220 polarimeter. Mass spectrometry was performed on a ThermoQuest Navigator from Thermo Electron, Electrospray (ES) spectra were obtained at 20 to 30 V. Accurate mass measurements were performed using Micromass Q-TOF global tandem. All samples were run under electrospray ionization mode using 50% acetonitrile in water and 0.1% formic acid as a solvent. Samples were run on W mode which gives a typical resolution of 19000 at FWHH. The instrument was calibrated with [Glu]-Fibrinopeptide B immediately prior to measurement.

LCMS

LC/MS (Shimazu LCMS-2020) using a mobile phase of water (A) (formic acid 0.1%) and acetonitrile (B) (formic acid 0.1%).

Gradient: initial composition 5% B held over 0.25 min, then increase from 5% B to 100% B over a 2 min period. The composition was held for 0.50 min at 100% B, then returned to 5% B in 0.05 minutes and hold there for 0.05 min. Total gradient run time equals 3 min. Flow rate 0.8 mL/min. Wavelength detection range: 190 to 800 nm. Oven temperature: 50° C. Column: Waters Acquity UPLC BEH Shield RP18 1.7 μm 2.1×50 mm.

Preparative HPLC

The conditions for the preparative HPLC were as follow: the HPLC (Shimadzu UFLC) was run using a mobile phase of water (0.1% formic acid) A and acetonitrile (0.1% formic acid) B. Wavelength detection range: 254 nm.

Column: Phenomenex Gemini 5μ C18 150×21-20 mm.

Gradient:

|  | B |
| --- | --- |
| t = 0 | 13% |
| t = 15.00 | 95% |
| t = 17.00 | 95% |
| t = 17.10 | 13% |
| t = 20.00 | 13% |

Total gradient run time is 20 min; flow rate 20.00 mL/min.

Synthesis of Intermediate 12
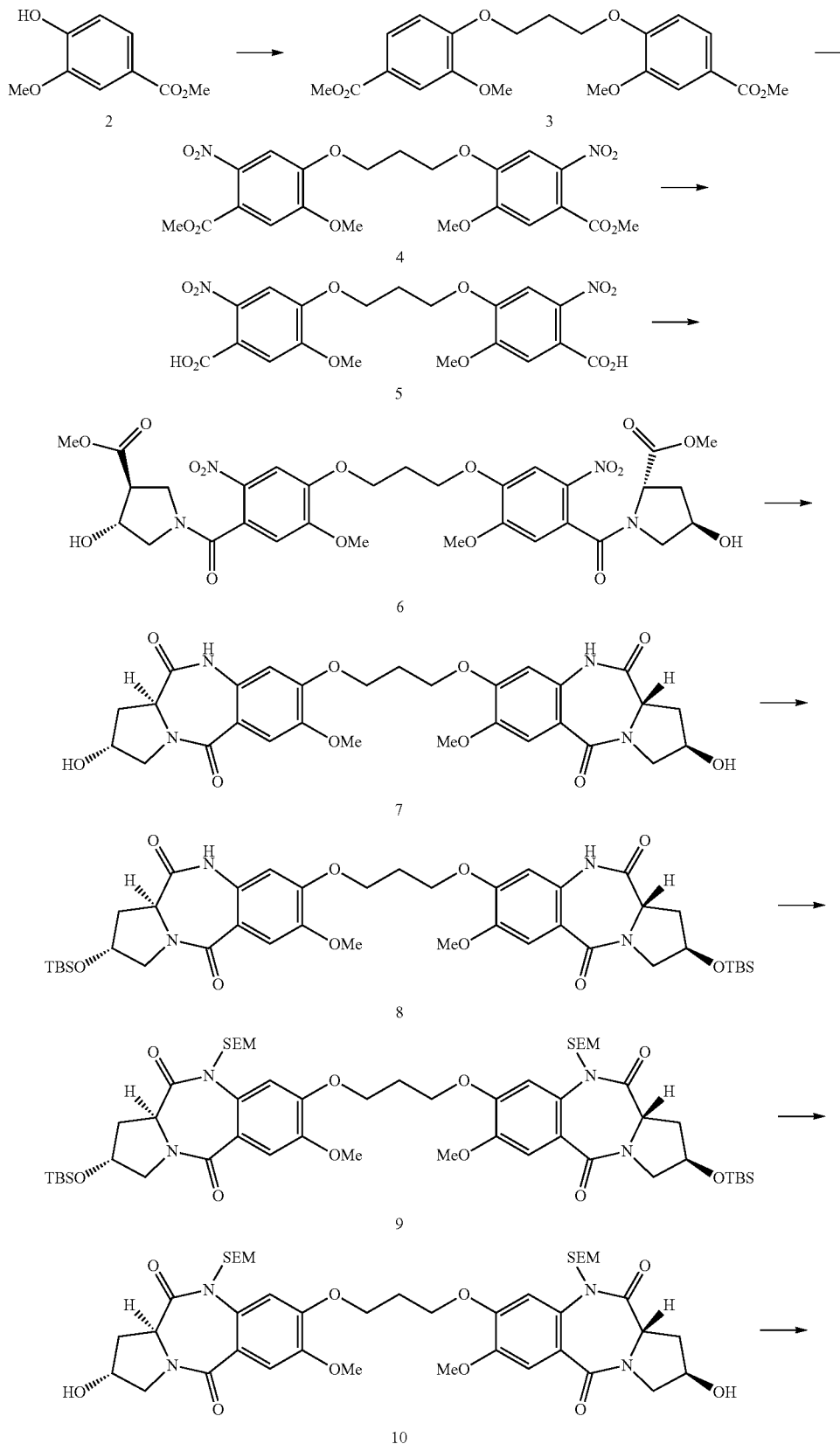

-continued

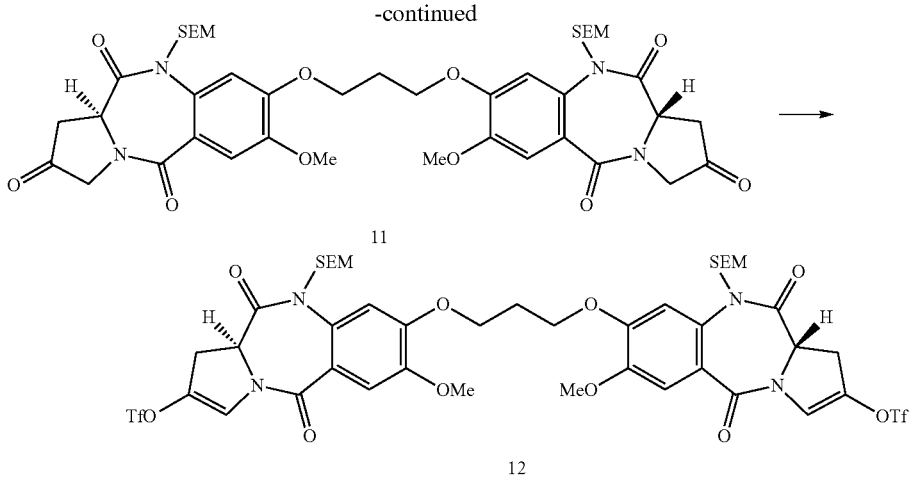

(a) 1',3'-Bis[2-methoxy-4-(methoxycarbonyl)phenoxy]propane (3)

Diisopropyl azodicarboxylate (71.3 mL, 73.2 g, 362 mmol) was added drop-wise over a period of 60 min to an overhead stirred solution of methyl vanillate 2 (60.0 g, 329 mmol) and Ph$_3$P (129.4 g, 494 mmol) in anhydrous THF (800 mL) at 0-5° C. (ice/acetone) under a nitrogen atmosphere. The reaction mixture was allowed to stir at 0-5° C. for an additional 1 hour after which time a solution of 1,3-propanediol (11.4 mL, 12.0 g, 158 mmol) in THF (12 mL) was added drop-wise over a period of 20 min. The reaction mixture was allowed to warm to room temperature and stirred for 5 days. The resulting white precipitate 3 was collected by vacuum filtration, washed with THF and dried in a vacuum desiccator to constant weight. Yield=54.7 g (84% based on 1,3-propanediol). Purity satisfactory by LC/MS (3.20 min (ES+) m/z (relative intensity) 427 ([M+Na]$^+$, 10); $^1$H NMR (400 MHz, CDCl$_3$) δ 7.64 (dd, 2H, J=1.8, 8.3 Hz), 7.54 (d, 2H, J=1.8 Hz), 6.93 (d, 2H, J=8.5 Hz), 4.30 (t, 4H, J=6.1 Hz), 3.90 (s, 6H), 3.89 (s, 6H), 2.40 (p, 2H, J=6.0 Hz).

(b) 1',3'-Bis[2-methoxy-4-(methoxycarbonyl)-5-nitrophenoxy]propane (4)

Solid Cu(NO$_3$)$_2$.3H$_2$O (81.5 g, 337.5 mmol) was added slowly to an overhead stirred slurry of the bis-ester 3 (54.7 g, 135 mmol) in acetic anhydride (650 mL) at 0-5° C. (ice/acetone). The reaction mixture was allowed to stir for 1 hour at 0-5° C. and then allowed to warm to room temperature. A mild exotherm (ca. 40-50° C.), accompanied by thickening of the mixture and evolution of NO$_2$ was observed at this stage. Additional acetic anhydride (300 mL) was added and the reaction mixture was allowed to stir for 16 hours at room temperature. The reaction mixture was poured on to ice (~1.5 L), stirred and allowed to return to room temperature. The resulting yellow precipitate was collected by vacuum filtration and dried in a desiccator to afford the desired bis-nitro compound 4 as a yellow solid. Yield=66.7 g (100%). Purity satisfactory by LC/MS (3.25 min (ES+) m/z (relative intensity) 517 ([M+Na]$^+$, 40); $^1$H NMR (400 MHz, CDCl$_3$) δ 7.49 (s, 2H), 7.06 (s, 2H), 4.32 (t, 4H, J=6.0 Hz), 3.95 (s, 6H), 3.90 (s, 6H), 2.45-2.40 (m, 2H).

(c) 1',3'-Bis(4-carboxy-2-methoxy-5-nitrophenoxy)propane (5)

A slurry of the methyl ester 4 (66.7 g, 135 mmol) in THF (700 mL) was treated with 1N NaOH (700 mL) and the reaction mixture was allowed to stir vigorously at room temperature. After 4 days stirring, the slurry became a dark coloured solution which was subjected to rotary evaporation under reduced pressure to remove THF. The resulting aqueous residue was acidified to pH 1 with concentrated HCl and the colourless precipitate 5 was collected and dried thoroughly in a vacuum oven (50° C.). Yield=54.5 g (87%). Purity satisfactory by LC/MS (2.65 min (ES+) m/z (relative intensity) 489 ([M+Na]$^+$, 30)); $^1$H NMR (400 MHz, DMSO-d$_6$) δ 7.62 (s, 2H), 7.30 (s, 2H), 4.29 (t, 4H, J=6.0 Hz), 3.85 (s, 6H), 2.30-2.26 (m, 2H).

(d) 1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate] (6)

Oxalyl chloride (24.5 mL, 35.6 g, 281 mmol) was added to a stirred suspension of the nitrobenzoic acid 5 (43 g, 92.3 mmol) and DMF (6 mL) in anhydrous DCM (600 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation under reduced pressure; the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 min to a stirred suspension of (2S,4R)-methyl-4-hydroxypyrrolidine-2-carboxylate hydrochloride (38.1 g, 210 mmol) and TEA (64.5 mL, g, 463 mmol) in DCM (400 mL) at −40° C. (dry ice/CH$_3$CN). Immediately, the reaction was complete as judged by LC/MS (2.47 min (ES+) m/z (relative intensity) 721 ([M+H]$^+$, 100). The mixture was diluted with DCM (200 mL) and washed with 1N HCl (300 mL), saturated NaHCO$_3$ (300 mL), brine (400 mL), dried (MgSO$_4$), filtered and the solvent evaporated in vacuo to give the pure product 6 as an orange solid (66.7 g, 100%).

[α]$^{22}_D$=−46.1° (c=0.47, CHCl$_3$); $^1$H NMR (400 MHz, CDCl$_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, CDCl$_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl$_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^+$·, 47), 388 (80); HRMS [M+H]$^+$· theoretical C$_{31}$H$_{36}$N$_4$O$_{16}$ m/z 721.2199, found (ES$^+$) m/z 721.2227.

(e) 1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (7)

Method A: A solution of the nitro-ester 6 (44 g, 61.1 mmol) in MeOH (2.8 L) was added to freshly purchased Raney® nickel (~50 g of a ~50% slurry in H$_2$O) and anti-bumping granules in a 5 L 3-neck round bottomed flask. The mixture was heated at reflux and then treated dropwise with a solution of hydrazine hydrate (21.6 mL, 22.2 g, 693 mmol) in MeOH (200 mL) at which point vigorous effervescence was observed. When the addition was complete (~45 min) additional Raney® nickel was added carefully until effervescence had ceased and the initial yellow colour of the reaction mixture was discharged. The mixture was heated at reflux for a further 5 min at which point the reaction was deemed complete by TLC (90:10 v/v CHCl$_3$/MeOH) and LC/MS (2.12 min (ES+) m/z (relative intensity) 597 ([M+H]$^+$·, 100)). The reaction mixture was filtered hot immediately through a sinter funnel containing celite with vacuum suction. The filtrate was reduced in volume by evaporation in vacuo at which point a colourless precipitate formed which was collected by filtration and dried in a vacuum desiccator to provide 7 (31 g, 85%). [α]$^{27}_D$=+404° (c=0.10, DMF); $^1$H NMR (400 MHz, DMSO-d$_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-d$_6$) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^+$·, 10), 597 ([M+H]$^+$·, 52), 445 (12), 326 (11); HRMS [M+H]$^+$· theoretical C$_{29}$H$_{32}$N$_4$O$_{10}$ m/z 597.2191, found (ES$^+$) m/z 597.2205.

Method B: A suspension of 10% Pd/C (7.5 g, 10% w/w) in DMF (40 mL) was added to a solution of the nitro-ester 6 (75 g, 104 mmol) in DMF (360 mL). The suspension was hydrogenated in a Parr hydrogenation apparatus over 8 hours. Progress of the reaction was monitored by LC/MS after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2:1 volume of precipitate) and dried in a vacuum desiccator to provide 7 (50 g, 81%). Analytical data for method B: Identical to those obtained for Method A (optical rotation, $^1$H NMR, LC/MS and TLC).

(f) 1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (8)

TBSCl (27.6 g, 182.9 mmol) and imidazole (29.9 g, 438.8 mmol) were added to a cloudy solution of the tetralactam 7 (21.8 g, 36.6 mmol) in anhydrous DMF (400 mL) at 0° C. (ice/acetone). The mixture was allowed to stir under a nitrogen atmosphere for 3 hours after which time the reaction was deemed complete as judged by LC/MS (3.90 min (ES+) m/z (relative intensity) 825 ([M+H]$^+$·, 100). The reaction mixture was poured onto ice (~1.75 L) and allowed to warm to room temperature with stirring. The resulting white precipitate was collected by vacuum filtration, washed with H$_2$O, diethyl ether and dried in the vacuum desicator to provide pure 8 (30.1 g, 99%). [α]$^{23}_D$=+234° (c=0.41, CHCl$_3$); $^1$H NMR (400 MHz, CDCl$_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, CDCl$_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl$_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) m/z (relative intensity) 825 ([M+H]$^+$·, 62), 721 (14), 440 (38); HRMS [M+H]$^+$· theoretical C$_{41}$H$_{60}$N$_4$O$_{10}$Si$_2$ m/z 825.3921, found (ES$^+$) m/z 825.3948.

(g) 1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (9)

A solution of n-BuLi (68.3 mL of a 1.6 M solution in hexane, 109 mmol) was added dropwise to a stirred suspension of the tetralactam 8 (30.08 g, 36.4 mmol) in anhydrous THF (600 mL) at −30° C. (dry ice/ethylene glycol) under a nitrogen atmosphere. The reaction mixture was allowed to stir at this temperature for 1 hour (now a reddish orange colour) at which point a solution of SEMCl (19.3 mL, 18.2 g, 109 mmol) in anhydrous THF (120 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^+$·, 100). The THF was removed by evaporation in vacuo and the resulting residue dissolved in EtOAc (750 mL), washed with H$_2$O (250 mL), brine (250 mL), dried (MgSO$_4$) filtered and evaporated in vacuo to provide the crude N10-SEM-protected tetralactam 9 as an oil (max$^m$ 39.5 g, 100%). Product carried through to next step without purification. [α]$^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81

Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^+$·, 48), 1085 ([M+H]$^+$·, 100), 1009 (5), 813 (6); HRMS [M+H]$^+$· theoretical C$_{53}$H$_{88}$N$_4$O$_{12}$Si$_4$ m/z 1085.5548, found (ES$^+$) m/z 1085.5542.

(h) 1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (10)

A solution of TBAF (150 mL of a 1.0 M solution in THF, 150 mmol) was added to a stirred solution of the crude bis-silyl ether 9 [84.0 g (max$^m$ 56.8 g), 52.4 mmol] in THF (800 mL) at room temperature. After stirring for 1 hour, analysis of the reaction mixture by TLC (95:5 v/v CHCl$_3$/MeOH) revealed completion of reaction. The THF was removed by evaporation under reduced pressure at room temperature and the resulting residue dissolved in EtOAc (500 mL) and washed with NH$_4$Cl (300 mL). The combined organic layers were washed with brine (60 mL), dried (MgSO$_4$), filtered and evaporated under reduced pressure to provide the crude product. Purification by flash chromatography (gradient elution: 100% CHCl$_3$ to 96:4 v/v CHCl$_3$/MeOH) gave the pure tetralactam 10 as a white foam (36.0 g, 79%). LC/MS 3.33 min (ES+) m/z (relative intensity) 879 ([M+Na]$^+$·, 100), 857 ([M+H]$^+$·, 40); [α]$^{23}_D$=+202° (c =0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, CHCl$_3$) 2956, 1684, 1625, 1604, 1518, 1464, 1434, 1361, 1238, 1058, 1021 cm$^{-1}$; MS (ES$^+$) m/z (relative intensity) 885 ([M+29]$^+$·, 70), 857 ([M+H]$^+$·, 100), 711 (8), 448 (17); HRMS [M+H]$^+$· theoretical C$_{41}$H$_{60}$N$_4$O$_{12}$Si$_2$ 857.3819, found (ES$^+$) m/z 857.3826.

(i) 1,1'-[[(Propane-1,3-diyl)dioxy]bis(11aS)-7-methoxy-2-oxo-10-((2-(trimethylsilyl)ethoxy)methyl)-1,2,3,10,11,11a-hexahydro-5H-pyrrolo[2,1-c][1,4]-benzodiazepin-5,11-dione] (11)

Diol 10 (25.6 g, 30 mmol, 1 eq.), NaOAc (6.9 g, 84 mmol, 2.8 eq.) and TEMPO (188 mg, 1.2 mmol, 0.04 eq.) were dissolved in DCM (326 mL) under Ar. This was cooled to −8° C. (internal temperature) and TCCA (9.7 g, 42 mmol, 1.4 eq.) was added portionwise over 15 minutes. TLC (EtOAc) and LC/MS [3.60 min. (ES+) m/z (relative intensity) 854.21 ([M+H]$^+$·, 40), (ES−) m/z (relative intensity) 887.07 ([M−H+Cl]$^−$·, 10)] after 30 minutes indicated that reaction was complete. Cold DCM (200 mL) was added and the mixture was filtered through a pad of Celite before washing with a solution of saturated sodium hydrogen carbonate/sodium thiosulfate (1:1 v/v; 200 mL×2). The organic layer was dried with MgSO$_4$, filtered and the solvent removed in vacuo to yield a yellow/orange sponge (25.4 g, 99%). LC/MS [3.60 min. (ES+) m/z (relative intensity) 854.21 ([M+H]$^+$·, 40); [α]$^{20}_D$=+291° (c=0.26, CHCl$_3$); $^1$H NMR (400 MHz, CDCl$_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}$C NMR (100 MHz, CDCl$_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, CHCl$_3$) 2957, 1763, 1685, 1644, 1606, 1516, 1457, 1434, 1360, 1247, 1209, 1098, 1066, 1023 cm$^{-1}$; MS (ES$^+$) m/z (relative intensity) 881 ([M+29]$^+$·, 38), 853 ([M+H]$^+$·, 100), 707 (8), 542 (12); HRMS [M+H]$^+$· theoretical C$_{41}$H$_{56}$N$_4$O$_{12}$Si$_2$ 853.3506, found (ES$^+$) m/z 853.3502.

(j) 1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (12)

Anhydrous 2,6-lutidine (5.15 mL, 4.74 g, 44.2 mmol) was injected in one portion to a vigorously stirred solution of bis-ketone 11 (6.08 g, 7.1 mmol) in dry DCM (180 mL) at −45° C. (dry ice/acetonitrile) under a nitrogen atmosphere. Anhydrous triflic anhydride, taken from a freshly opened ampoule (7.2 mL, 12.08 g, 42.8 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated NaHCO$_3$ (200 mL), brine (100 mL) and dried (MgSO$_4$). Filtration and evaporation of the solvent under reduced pressure afforded the crude product which was purified by flash column chromatography (gradient elution: 90:10 v/v n-hexane/EtOAc to 70:30 v/v n-hexane/EtOAc) to afford bis-enol triflate 12 as a yellow foam (5.5 g, 70%). LC/MS 4.32 min (ES+) m/z (relative intensity) 1139 ([M+Na]$^+$·, 20); [α]$^{24}_D$=+271° (c=0.18, CHCl$_3$); $^1$H NMR (400 MHz, CDCl$_3$) δ 7.33 (s, 2H), 7.26 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H); $^{13}$C NMR (100 MHz, CDCl$_3$) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, −1.25; IR (ATR, CHCl$_3$) 2958, 1690, 1646, 1605, 1517, 1456, 1428, 1360, 1327, 1207, 1136, 1096, 1060, 1022, 938, 913 cm$^{-1}$; MS (ES$^+$) m/z (relative intensity) 1144 ([M+28]$^+$·, 100), 1117 ([M+H]$^+$·, 48), 1041 (40), 578 (8); HRMS [M +H]$^+$· theoretical C$_{43}$H$_{54}$N$_4$O$_{16}$Si$_2$S$_2$F$_6$ m/z 1117.2491, found (ES$^+$) m/z 1117.2465.

Synthesis of Intermediate 15

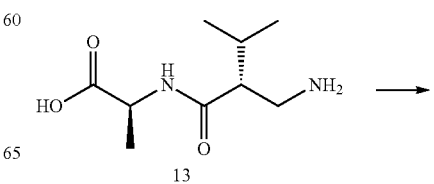

13

-continued

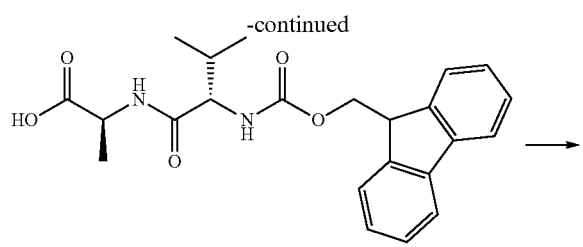

14

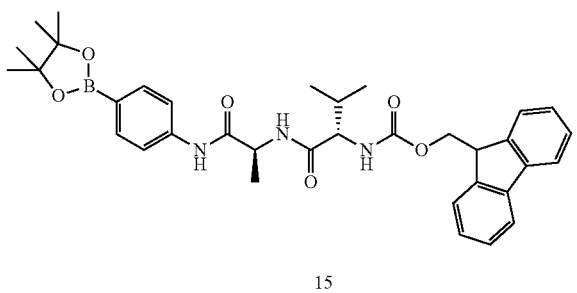

15

(a) (R)-2-((R)-2-(((((9H-fluoren-9-yl)methoxy)carbonyl)amino)-3-methylbutanamido) propanoic acid (14)

HO-Ala-Val-H 13 (350 mg, 1.86 mmol) and Na$_2$CO$_3$ (493 mg, 4.65 mmol) were dissolved in distilled H$_2$O (15 mL) and the mixture was cooled to 0° C. before dioxane (15 mL) was added (partial precipitation of the amino acid salt occurred). A solution of Fmoc-Cl (504 mg, 1.95 mmol) in dioxane (15 mL) was added dropwise with vigorous stirring over 10 minutes. The resulting mixture was stirred at 0° C. for 2 hours before the ice bath was removed and stirring was maintained for 16 hours. The solvent was removed by rotary evaporation under reduced pressure and the residue dissolved in water (150 mL). The pH was adjusted from 9 to 2 with 1N HCl and the aqueous layer was subsequently extracted with EtOAc (3×100 mL). The combined organics were washed with brine (100 mL), dried with MgSO$_4$, filtered and the volatiles removed by rotary evaporation under reduced pressure to afford pure HO-Ala-Val-Fmoc 14 (746 mg, 97% yield). LC/MS 2.85 min (ES+) m/z (relative intensity) 410.60; $^1$H-NMR (400 MHz, CDCl$_3$) δ 7.79 (d, J=7.77 Hz, 2H), 7.60 (d, J=7.77 Hz, 2H), 7.43 (d, J=7.5 Hz, 2H), 7.34 (d, J=7.5 Hz, 2H), 6.30 (bs, 1H), 5.30 (bs, 1H), 4.71-7.56 (m, 1H), 4.54-4.36 (m, 2H), 4.08-3.91 (m, 1H), 2.21-2.07 (m, 1H), 1.50 (d, J=7.1 Hz, 3H), 1.06-0.90 (m, 6H).

(b) (9H-fluoren-9-yl)methyl ((S)-3-methyl-1-oxo-1-(((S)-1-oxo-1-((4-(4,4,5,5-tetramethyl-1,3,2-dioxaborolan-2-yl)phenyl)amino)propan-2-yl)amino)butan-2-yl)carbamate (15)

4-Aminophenylboronic acid pinacol ester was added (146.9 mg, 0.67 mmol) was added to a solution of HO-Ala-Val-Fmoc 14 (330 mg, 0.8 mmol), DCC (166 mg, 0.8 mmol) and DMAP (5 mg, cat.) in dry DCM (8 mL) previously stirred for 30 minutes at room temperature in a flask flushed with argon. The reaction mixture was then allowed to stir at room temperature overnight. The reaction was followed by LCMS and TLC. The reaction mixture was diluted with CH$_2$Cl$_2$ and the organics were washed with H$_2$O and brine before being dried with MgSO$_4$, filtered and the solvent removed by rotary evaporation under reduced pressure. The crude product was dryloaded on a silicagel chromatography column (Hexane/EtOAc, 6:4) and pure product 15 was isolated as a white solid in 88% yield (360 mg).

Example 1

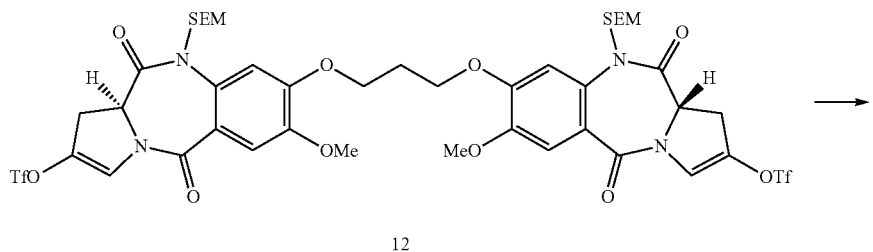

12

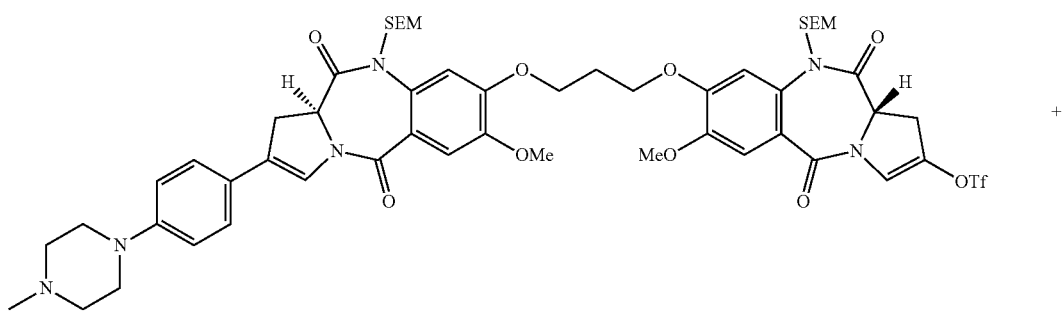

16

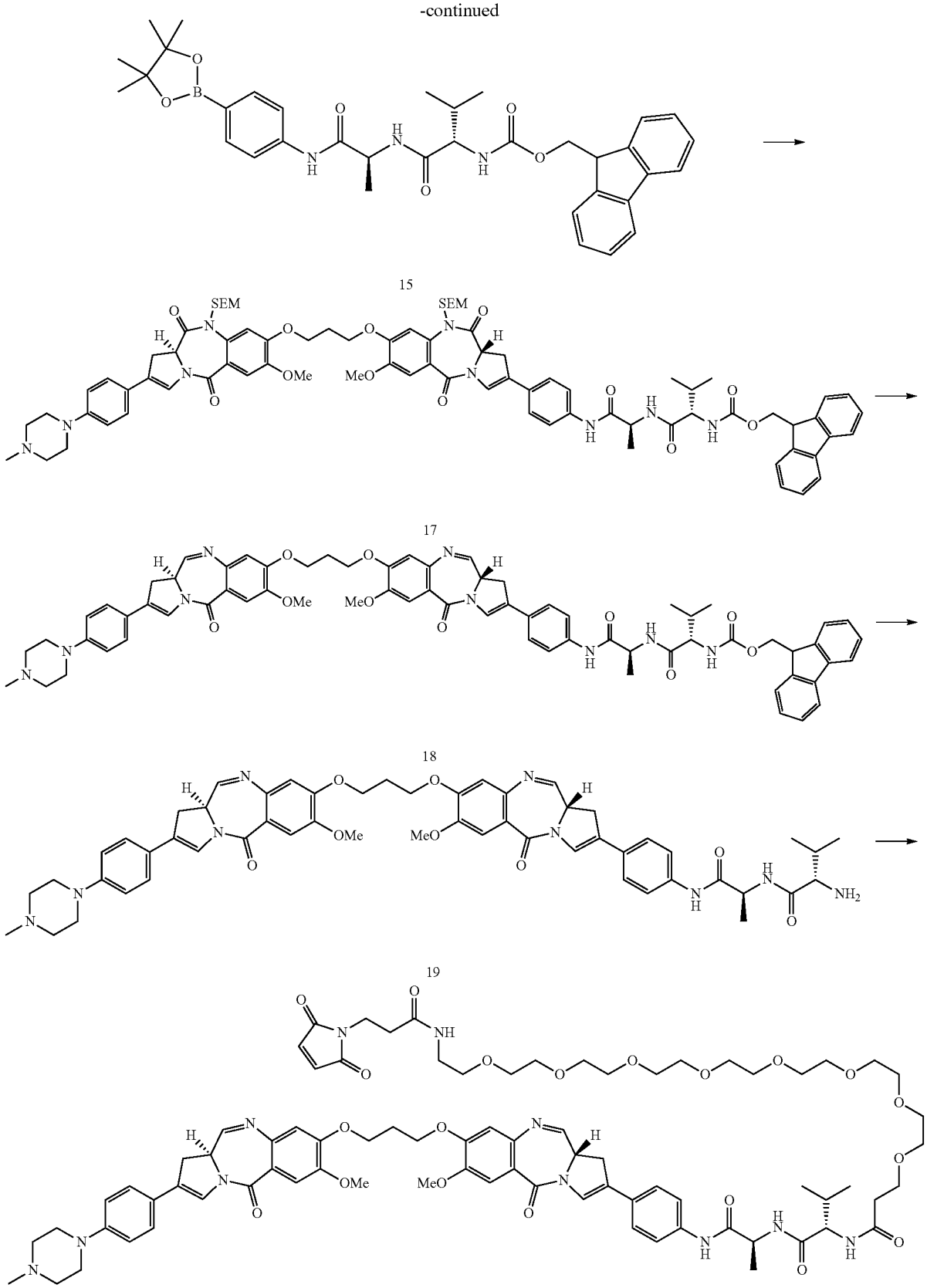

(a) (S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl trifluoromethanesulfonate (16)

Pd(PPh$_3$)$_4$ (20.6 mg, 0.018 mmol) was added to a stirred mixture of the bis-enol triflate 12 (500 mg, 0.44 mmol), N-methyl piperazine boronic ester (100 mg, 0.4 mmol), Na$_2$CO$_3$ (218 mg, 2.05 mmol), MeOH (2.5 mL), toluene (5 mL) and water (2.5 mL). The reaction mixture was allowed to stir at 30° C. under a nitrogen atmosphere for 24 hours after which time all the boronic ester has consumed. The reaction mixture was then evaporated to dryness before the residue was taken up in EtOAc (100 mL) and washed with H$_2$O (2×50 mL), brine (50 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 16 as a yellowish foam (122.6 mg, 25%). LC/MS 3.15 min (ES+) m/z (relative intensity) 1144 ([M+H]$^+$, 20%).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl)carbamate (17)

PBD-triflate 16 (359 mg, 0.314 mmol), boronic pinacol ester 15 (250 mg, 0.408 mmol) and triethylamine (0.35 mL, 2.51 mmol) were dissolved in a mixture of toluene/MeOH/H$_2$O, 2:1:1 (3 mL). The microwave vessel was purged and filled with argon three times before tetrakis(triphenylphosphine)palladium(0) (21.7 mg, 0.018 mmol) was added and the reaction mixture placed in the microwave at 80° C. for 10 minutes. Subsequently, CH$_2$Cl$_2$ (100 mL) was added and the organics were washed with water (2×50 mL) and brine (50 mL) before being dried with MgSO$_4$, filtered and the volatiles removed by rotary evaporation under reduced pressure. The crude product was purified by silica gel chromatography column (CHCl$_3$/MeOH, 100% to 9:1) to afford pure 17 (200 mg, 43% yield). LC/MS 3.27 min (ES+) m/z (relative intensity) 1478 ([M+H]$^+$, 100%).

(c) (9H-fluoren-9-yl)methyl ((S)-1-(((S)-1-((4-((S)-7-methoxy-8-(3-(((S)-7-methoxy-2-(4-(4-methyl piperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (18)

A solution of Super-Hydride® (0.34 mL, 1M in THF) was added dropwise to a solution of SEM-dilactam 17 (200 mg, 0.135 mmol) in THF (5 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with MgSO$_4$, filtered and the solvent removed by rotary evaporation under reduced pressure. The crude product was dissolved in MeOH (6 mL), CH$_2$Cl$_2$ (3 mL), water (1 mL) and enough silica gel to form a thick stirring suspension. After 5 days, the suspension was filtered through a sintered funnel and washed with CH$_2$Cl$_2$/MeOH (9:1) (100 mL) until the elution of the product was complete. The organic layer was washed with brine (2×50 mL), dried with MgSO$_4$, filtered and the solvent removed by rotary evaporation under reduced pressure. Purification by silica gel column chromatography (100% CHCl$_3$ to 96% CHCl$_3$/4% MeOH) afforded the product 18 as a yellow solid (100 mg, 63%). LC/MS 2.67 min (ES+) m/z (relative intensity) 1186 ([M+H]$^+$, 5%).

(d) (S)-2-amino-N—((S)-1-((4-((R)-7-methoxy-8-(3-(((R)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (19)

Excess piperidine was added (0.1 mL, 1 mmol) to a solution of PBD 18 (36.4 mg, 0.03 mmol) in DMF (0.9 mL). The mixture was allowed to stir at room temperature for 20 min, at which point the reaction had gone to completion (as monitored by LC/MS). The reaction mixture was diluted with CH$_2$Cl$_2$ (50 mL) and the organic phase was washed with H$_2$O (3×50 mL) until complete piperidine removal. The organic phase was dried over MgSO$_4$, filtered and excess solvent removed by rotary evaporation under reduced pressure to afford crude product 19 which was used as such in the next step. LC/MS 2.20 min (ES+) m/z (relative intensity) 964 ([M+H]$^+$, 5%).

(e) 1-(3-(2,5-dioxo-2,5-dihydro-1H-pyrrol-1-yl)propanamido)-N-((2S)-1-(((2S)-1-((4-(7-methoxy-8-(3-((7-methoxy-2-(4-(4-methylpiperazin-1-yl)phenyl)-5-oxo-5,11a-dihydro-1H-benzo [e]pyrrolo[1,2-a][1,4]diazepin-8-yl)oxy)propoxy)-5-oxo-5,11a-dihydro-1H-benzo [e]pyrrolo[1,2-a][1,4]diazepin-2-yl)phenyl)amino)-1-oxopropan-2-yl)amino)-3-methyl-1-oxobutan-2-yl)-3,6,9,12,15,18,21,24-octaoxaheptacosan-27-amide (20)

EDCl hydrochloride (8 mg, 0.042 mmol) was added to a suspension of Maleimide-PEG$_8$-acid (25 mg, 0.042 mmol) in dry CH$_2$Cl$_2$ (4 mL) under argon atmosphere. PBD 19 (42 mg, crude) was added straight away and stirring was maintained until the reaction was complete (3 hours). The reaction was diluted with CH$_2$Cl$_2$ and the organic phase was washed with H$_2$O and brine before being dried over MgSO$_4$, filtered and excess solvent removed by rotary evaporation under reduced pressure by rotary evaporation under reduced pressure. The product was purified by careful silica gel chromatography (slow elution starting with 100% CHCl$_3$ up to 9:1 CHCl$_3$/MeOH) followed by reverse phase HPLC to remove unreacted maleimide-PEG$_8$-acid. The product 20 was isolated in 10% over two steps (6.6 mg). LC/MS 1.16 min (ES+) m/z (relative intensity) 770.20 ([M+2H]$^+$, 40%).

Example 2
Alternative Synthesis of Compound 17
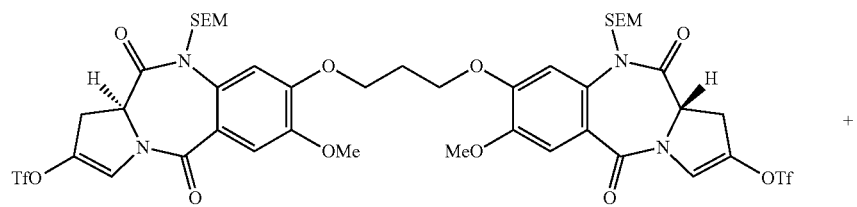
12
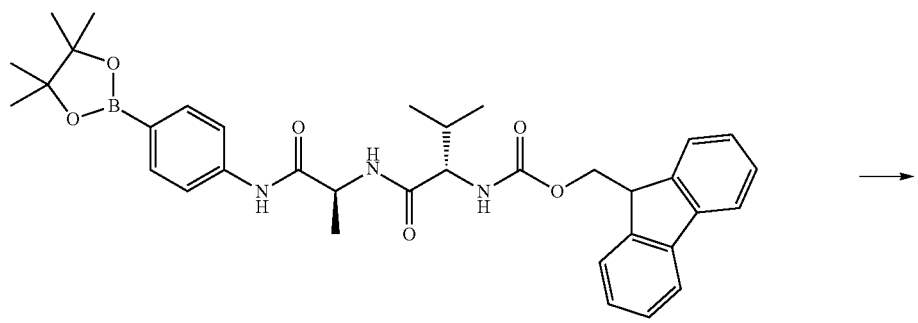
20
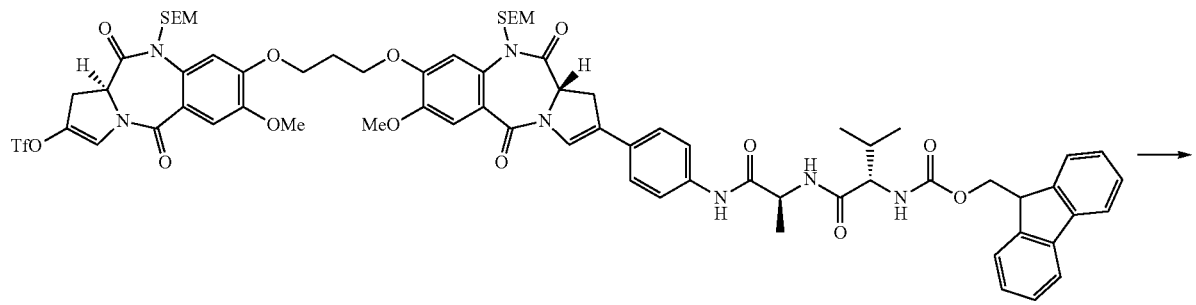
21
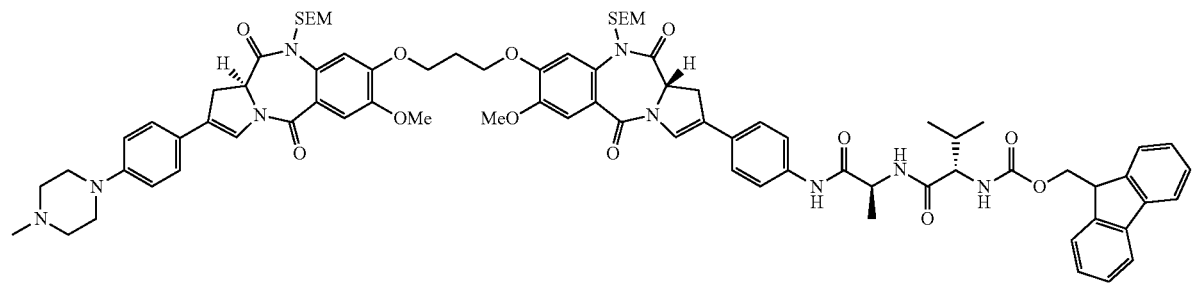
17

(a) 8-(3-((2-(4-((S)-2-((S)-2-((((9H-fluoren-9-yl)methoxy)carbonyl)amino)-3-methylbutanamido)propanamido)phenyl)-7-methoxy-5,11-dioxo-10-((2-(trimethylsilyl)ethoxy)methyl)-5,10,11,11a-tetrahydro-H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (21)

Bis-triflate 12 (2.03 g, 1.81 mmol), boronic pinacol ester 20 (1 g, 1.63 mmol) and Na$_2$CO$_3$ (881 mg, 8.31 mmol) were dissolved in a mixture of toluene/MeOH/H$_2$O, 2:1:1 (40 mL). The reaction flask was purged and filled with argon three times before tetrakis(triphenylphosphine)palladium(0) (41 mg, 0.035 mmol) was added and the reaction mixture heated to 30° C. overnight. The solvents were removed under reduce pressure and the residue was taken up in H$_2$O (100 mL) and extracted with EtOAc (3×100 mL). The combined organics were washed with brine (100 mL), dried with MgSO$_4$, filtered and the volatiles removed by rotary evaporation under reduced pressure. The crude product was purified by silica gel chromatography column (Hexane/EtOAc, 8:2 to 25:75) to afford pure 21 in 33% yield (885 mg). LC/MS 3.85 min (ES+) m/z (relative intensity) 1452.90; $^1$H NMR (400 MHz, CDCl$_3$) δ 7.78-7.16 (m, 17H), 7.13 (s, 1H), 6.51-6.24 (m, 1H), 5.51 (dd, J=10.0, 5.1 Hz, 2H), 5.36-5.11 (m, 1H), 4.74 (dd, J=10.1, 4.4 Hz, 2H), 4.70-4.53 (m, 2H), 4.47 (d, J=6.4 Hz, 1H), 4.37 (d, J=7.2 Hz, 1H), 4.27 (m, 4H), 4.20-4.14 (m, 1H), 3.90 (s, 3H), 3.89 (s, 3H), 3.77 (ddd, J=16.7, 9.0, 6.4 Hz, 3H), 3.71-3.61 (m, 2H), 3.24-2.91 (m, 3H), 2.55-2.33 (m, 2H), 2.22-2.07 (m, 1H), 1.52-1.37 (m, 3H), 1.04-0.86 (m, 10H), 0.00 (s, 18H).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl)carbamate (17)

PBD-triflate 21 (469 mg, 0.323 mmol), boronic pinacol ester (146.5 mg, 0.484 mmol) and Na$_2$CO$_3$ (157 mg, 1.48 mmol) were dissolved in a mixture of toluene/MeOH/H$_2$O, 2:1:1 (10 mL). The reaction flask was purged with argon three times before tetrakis(triphenylphosphine)palladium(0) (7.41 mg, 0.0064 mmol) was added and the reaction mixture heated to 30° C. overnight. The solvents were removed under reduced pressure and the residue was taken up in H$_2$O (50 mL) and extracted with EtOAc (3×50 mL). The combined organics were washed with brine (100 mL), dried with MgSO$_4$, filtered and the volatiles removed by rotary evaporation under reduced pressure. The crude product was purified by silica gel column chromatography (CHCl$_3$ 100% to CHCl$_3$/MeOH 95%:5%) to afford pure 17 in 33% yield (885 mg). LC/MS 3.27 min (ES+) m/z (relative intensity) 1478 ([M+H]$^{+\cdot}$, 100%).

Example 3

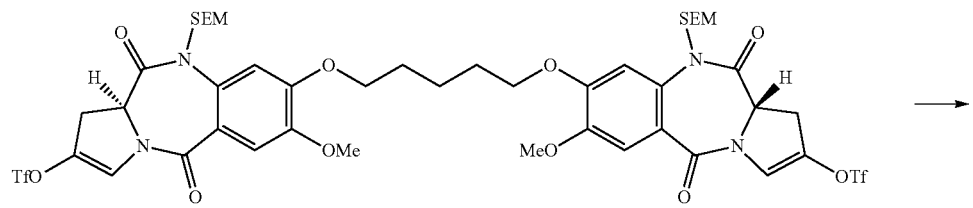

22

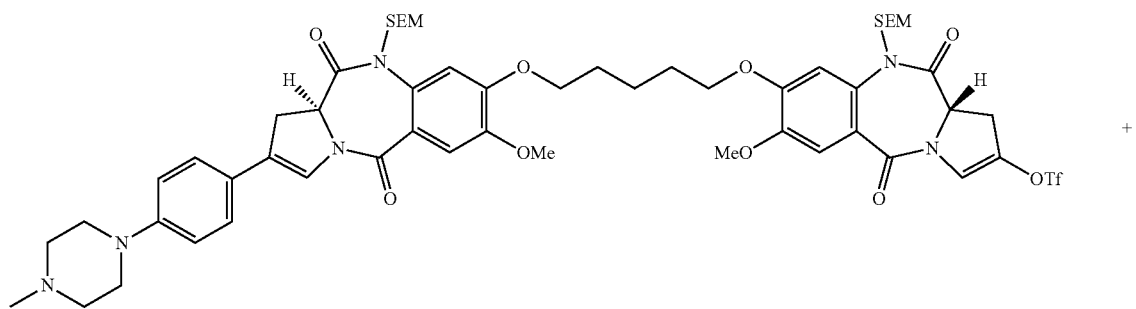

23

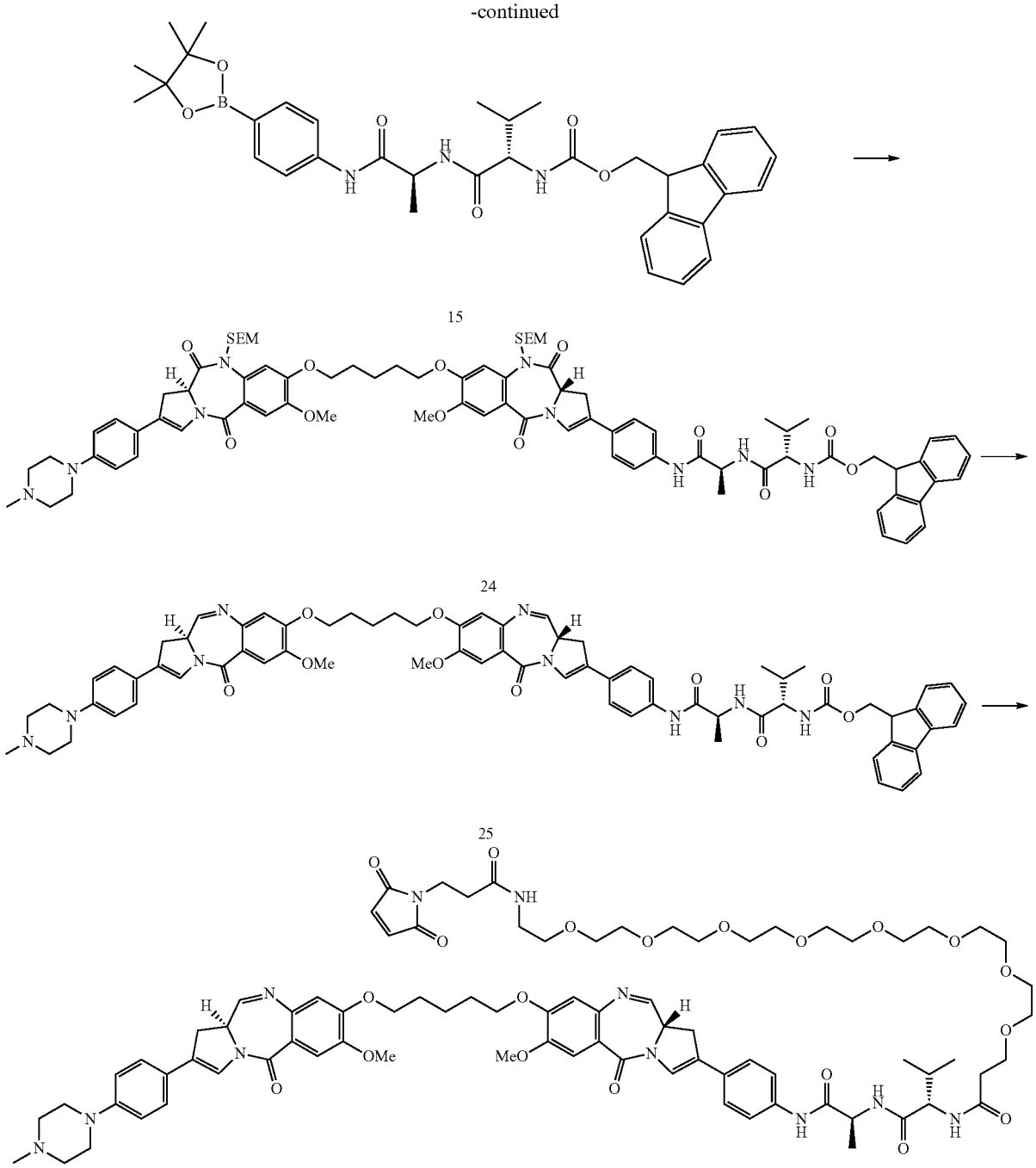

(a) (S)-7-methoxy-8-((5-(((S)-7-methoxy-2-(4-(4-methypiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (23)

Pd(PPh$_3$)$_4$ (30 mg, 26 μmol) was added to a stirred mixture of the bis-enol triflate 22 (1 g, 0.87 mmol), 4-(4-methylpiperazin-1-yl)phenylboronic acid, pinacol ester (264 mg, 0.87 mmol), Na$_2$CO$_3$ (138 mg, 1.30 mmol), EtOH (5 mL), toluene (10 mL) and water (5 mL). The reaction mixture was allowed to stir under a nitrogen atmosphere overnight at room temperature after which time the complete consumption of starting material was observed by TLC (EtOAc) and LC/MS (1.52 min (ES+) m/z (relative intensity) 1171.40 ([M+H]$^{+\cdot}$, 100)). The reaction mixture was diluted with EtOAc (400 mL) and washed with H$_2$O (2×300 mL), brine (200 mL), dried (MgSO$_4$), filtered and evaporated under reduced pressure to provide the crude product.

Purification by flash chromatography (gradient elution: 100:0 v/v EtOAc/MeOH to 85:15 v/v EtOAc/MeOH) afforded the asymmetrical triflate 23 (285 mg, 28%). $^1$H NMR (400 MHz, CDCl3) δ 7.39 (s, 1H), 7.37-7.29 (m, 4H), 7.23 (d, J=2.8 Hz, 2H), 7.14 (t, J=2.0 Hz, 1H), 6.89 (d, J=9.0 Hz, 2H), 5.54 (d, J=10.0 Hz, 2H), 4.71 (dd, J=10.0, 2.6 Hz, 2H), 4.62 (td, J=10.7, 3.5 Hz, 2H), 4.13-4.01 (m, 4H), 3.97-3.87 (m, 8H), 3.85-3.75 (m, 2H), 3.74-3.63 (m, 2H), 3.31-3.22 (m, 4H), 3.14 (tdd, J=16.2, 10.8, 2.2 Hz, 2H), 2.73-2.56 (m, 4H), 2.38 (d, J=2.4 Hz, 3H), 2.02-1.92 (m, 4H), 1.73 (dd, J=9.4, 6.0 Hz, 2H), 1.04-0.90 (m, 4H), 0.05--0.00 (m, 18H). MS (ES$^+$) m/z (relative intensity) 1171.40 ([M+H]$^{+\cdot}$, 100).

(b) (9H-fluoren-9-yl)methyl ((S)-1-(((S)-1-((4-((S)-7-methoxy-8-((5-(((S)-7-methoxy-2-(4-(4-methyl-piperazin-1-yl)phenyl)-5,11-dioxo-10-((2-(trimethyl-silyl)ethoxy)methyl)-5,10,11,11a -tetrahydro-1H-benzo[e]pyrrolo[1,2-a][1,4]diazepin-8-yl)oxy) pentyl)oxy)-5,11-dioxo-10-((2-(trimethylsilyl) ethoxy)methyl)-5,10,11,11a-tetrahydro-1H-benzo[e] pyrrolo[1,2-a][1,4]diazepin-2-yl)phenyl)amino)-1-oxopropan-2-yl)amino)-3-methyl-1-oxobutan-2-yl) carbamate (24)

Pd(PPh$_3$)$_4$ (8 mg, 7 µmol) was added to a stirred mixture of the asymmetrical triflate 23 (269 mg, 0.23 mmol), Fmoc-Val-Ala-4-aminophenylboronic acid, pinacol ester 15 (210 mg, 0.34 mmol), Na$_2$CO$_3$ (36.5 mg, 0.34 mmol), EtOH (5 mL), toluene (10 mL), THF (1 mL), and water (5 mL). The reaction mixture was allowed to stir under a nitrogen atmosphere at 35° C. for 2 hours after which time the complete consumption of starting material was observed by TLC (80:20 v/v EtOAc/MeOH) and LC/MS (1.68 min (ES+) m/z (relative intensity) 1508.10 ([M+H]$^{+\cdot}$, 100)). The reaction mixture was diluted with EtOAc (100 mL) and washed with H$_2$O (1×100 mL), brine (200 mL), dried (MgSO$_4$), filtered and evaporated under reduced pressure to provide the crude product. Purification by flash chromatography (gradient elution: 100:0 v/v EtOAc/MeOH to 80:20 v/v EtOAc/MeOH) afforded the SEM protected dimer 24 (240 mg, 69%). $^1$H NMR (400 MHz, CDCl$_3$) δ 8.42 (s, 1H), 7.76 (d, J=7.5 Hz, 2H), 7.63-7.49 (m, 4H), 7.45-7.28 (m, 9H), 7.25 (d, J=2.9 Hz, 1H), 6.87 (t, J=14.0 Hz, 2H), 6.41 (s, 1H), 5.63-5.49 (m, 2H), 5.25 (s, 1H), 4.71 (d, J=10.1 Hz, 2H), 4.68-4.57 (m, 2H), 4.49 (d, J=6.7 Hz, 2H), 4.20 (s, 1H), 4.16-4.02 (m, 4H), 4.00-3.87 (m, 7H), 3.86-3.61 (m, 7H), 3.30-3.21 (m, 4H), 3.19-3.05 (m, 2H), 2.69-2.54 (m, 4H), 2.37 (s, 3H), 2.04-1.92 (m, 4H), 1.91-1.79 (m, 4H), 1.72 (s, 2H), 1.46 (d, J=6.9 Hz, 3H), 1.04-0.82 (m, 8H), 0.04--0.02 (m, 18H). MS (ES$^+$) m/z (relative intensity) 1508.10 ([M+H]$^{+\cdot}$, 100).

(c) (9H-fluoren-9-yl)methyl ((S)-1-(((S)-1-((4-((S)-7-methoxy-8-((5-(((S)-7-methoxy-2-(4-(4-methyl-piperazin-1-yl)phenyl)-5-oxo-5,11a-dihydro-1H-benzo[e]pyrrolo[1,2-a][1,4]diazepin-8-yl)oxy) pentyl)oxy)-5-oxo-5,11a-dihydro-1H-benzo[e] pyrrolo[1,2-a][1,4]diazepin-2-yl)phenyl)amino)-1-oxopropan-2-yl)amino)-3-methyl-1-oxobutan-2-yl) carbamate (25)

Super hydride (0.358 mL, 0.358 mmol, 1.0 M in THF) was added dropwise to a stirred solution of the SEM-tetralactam 24 (216 mg, 0.143 mmol) in anhydrous THF (10 mL) at --78° C. The reaction mixture was allowed to stir for 3 hours after which time the complete conversion of starting material directly was observed by LC/MS (1.37 min (ES+) m/z (relative intensity) 608.15 (([M+2H]$^{2+}$)/2, 100)). The reaction mixture was carefully diluted with H$_2$O (100 mL) and extracted with DCM (100 mL). The organic layers was washed with brine (100 mL), dried over MgSO$_4$, filtered and evaporated under reduced pressure to provide the intermediate SEM-carbinolamine. The white solids were immediately dissolved in MeOH (100 mL), DCM (10 mL) and H$_2$O (20 mL) and treated with flash silica gel (50 g). The thick suspension was allowed to stir at room temperature for 4 days after which time the formation of a significant quantity of desired product was observed by TLC (90:10 v/v CHCl$_3$/MeOH). The reaction mixture was filtered through a porosity 3 sinter funnel and the pad rinsed slowly and thoroughly with 90:10 v/v CHCl$_3$/MeOH until no further product eluted (checked by TLC). The filtrate was washed with brine (100 mL), dried (MgSO$_4$), filtered and evaporated in vacuo, followed by high vacuum drying, to provide the crude product. Purification by flash chromatography (gradient elution: HPLC grade 98:2 v/v CHCl$_3$/MeOH to 88:12 v/v CHCl$_3$/MeOH) gave 25 as a mixture of carbinolamine ethers and imine (80 mg, 46%). $^1$H NMR (400 MHz, CDCl3) δ 8.52 (s, 1H), 7.87 (d, J=3.9 Hz, 2H), 7.75 (d, J=7.5 Hz, 2H), 7.66-7.26 (m, 12H), 6.90 (d, J=8.8 Hz, 2H), 6.81 (s, 1H), 6.64 (d, J=6.0 Hz, 1H), 5.37 (d, J=5.7 Hz, 1H), 4.74-4.58 (m, 2H), 4.54-4.31 (m, 4H), 4.26-3.98 (m, 6H), 3.94 (s, 2H), 3.86 (dd, J=13.6, 6.6 Hz, 1H), 3.63-3.48 (m, 2H), 3.37 (dd, J=16.5, 5.6 Hz, 2H), 3.31-3.17 (m, 4H), 2.66-2.51 (m, 4H), 2.36 (s, 3H), 2.16 (d, J=5.1 Hz, 1H), 2.06-1.88 (m, 4H), 1.78-1.55 (m, 6H), 1.46 (d, J=6.8 Hz, 3H), 0.94 (d, J=6.8 Hz, 6H). MS (ES$^+$) m/z (relative intensity) 608.15 (([M+2H]$^{2+}$)/2, 100).

(d) 1-(3-(2,5-dioxo-2,5-dihydro-1H-pyrrol-1-yl)pro-panamido)-N—((S)-1-(((S)-1-((4-((S)-7-methoxy-8-((5-(((S)-7-methoxy-2-(4-(4-methylpiperazin-1-yl) phenyl)-5-oxo-5,11a-dihydro-1H -benzo[e]pyrrolo [1,2-a][1,4]diazepin-8-yl)oxy)pentyl)oxy)-5-oxo-5,11a-dihydro-1H -benzo[e]pyrrolo[1,2-a][1,4] diazepin-2-yl)phenyl)amino)-1-oxopropan-2-yl) amino)-3-methyl-1-oxobutan-2-yl)-3,6,9,12,15,18, 21,24-octaoxaheptacosan-27-amide (26)

Piperidine (0.2 mL) was added to a solution of 25 (77 mg, 63.4 µmol) in DMF (1 mL). The reaction mixture was allowed to stir for 20 minutes. The reaction mixture was carefully diluted with DCM (50 mL) and washed with water (50 mL). The organic layers was washed with brine (100 mL), dried over MgSO$_4$, filtered and evaporated under reduced pressure to provide the unprotected valine intermediate. The crude residue was immediately redissolved in chloroform (5 mL). Mal(Peg)$_8$-acid (56 mg, 95 µmol) and EDCl (18 mg, 95 µmol) were added, followed by methanol (0.1 mL). The reaction was allowed to stir for 3 hours at room temperature at which point completion was observed by TLC and LC/MS (1.19 min (ES+) m/z (relative intensity) 784.25 (([M+2H]$^{2+}$)/2, 100)). The reaction mixture was diluted with chloroform (50 mL), washed with water (100 mL), dried (MgSO$_4$), filtered and evaporated in vacuo, followed by high vacuum drying, to provide the crude product.

Purification by flash chromatography (gradient elution: HPLC grade 96:4 v/v CHCl$_3$/MeOH to 90:10 v/v CHCl$_3$/MeOH) gave 26 as a yellow solid (43 mg, 43%). $^1$H NMR (400 MHz, CDCl$_3$) δ 8.73 (s, 1H), 7.88 (dd, J=7.6, 3.9 Hz, 2H), 7.75 (d, J=8.6 Hz, 2H), 7.52 (d, J=2.0 Hz, 2H), 7.44 (s, 1H), 7.40-7.28 (m, 4H), 6.91 (d, J=8.8 Hz, 2H), 6.81 (s, 2H), 6.69 (s, 2H), 6.48 (s, 1H), 4.72-4.63 (m, 1H), 4.46-4.34 (m, 2H), 4.25-4.03 (m, 6H), 3.95 (s, 4H), 3.84 (dd, J=17.2, 10.1 Hz, 4H), 3.72-3.46 (m, 30H), 3.44-3.32 (m, 4H), 3.30-3.20 (m, 4H), 2.75-2.63 (m, 1H), 2.59 (s, 4H), 2.55-2.43 (m, 3H), 2.37 (s, 3H), 2.29 (dd, J=12.7, 6.7 Hz, 1H), 2.03-1.89 (m, 4H), 1.72 (d, J=22.7 Hz, 8H), 1.46 (d, J=7.2 Hz, 3H), 1.01 (dd, J =11.5, 6.9 Hz, 6H). MS (ES+) m/z (relative intensity) 784.25 ((([M+2H]$^{2+}$)/2, 100).

Variations in General Experimental Methods for Example 4

The general methods for Example 4 are the same as above, except for:

Mass spectroscopy (MS) data were collected using a Waters Micromass LCT instrument coupled to a Waters 2795 HPLC separations module. Thin Layer Chromatography (TLC) was performed on silica gel aluminium plates (Merck 60, F$_{254}$). All other chemicals and solvents were used as supplied without further purification.

LCMS data were obtained using a Shimadzu Nexera series LC/MS with a Shimadzu LCMS-2020 quadrupole MS, with Electrospray ionisation. Mobile phase A—0.1% formic acid in water. Mobile phase B—0.1% formic acid in acetonitrile. Flow rate of 0.80 ml/min. Gradient from 5% B rising up to 100% B over 2.00 min, remaining at 100% B for 0.50 min and then back down to 5% B over 0.05 min (held for 0.45 min). The total run time is 3 min. Column: Waters Aquity UPLC BEH Shield RP18 1.7 μm, 2.1×50 mm.

Example 4

(i) (S)-((pentane-1,5-diylbis(oxy))bis(2-amino-5-methoxy-4,1-phenylene))bis(((S)-2-(((tert -butyldimethylsilyl)oxy)methyl)-4-methyl-2,3-dihydro-1H-pyrrol-1-yl)methanone) (35)

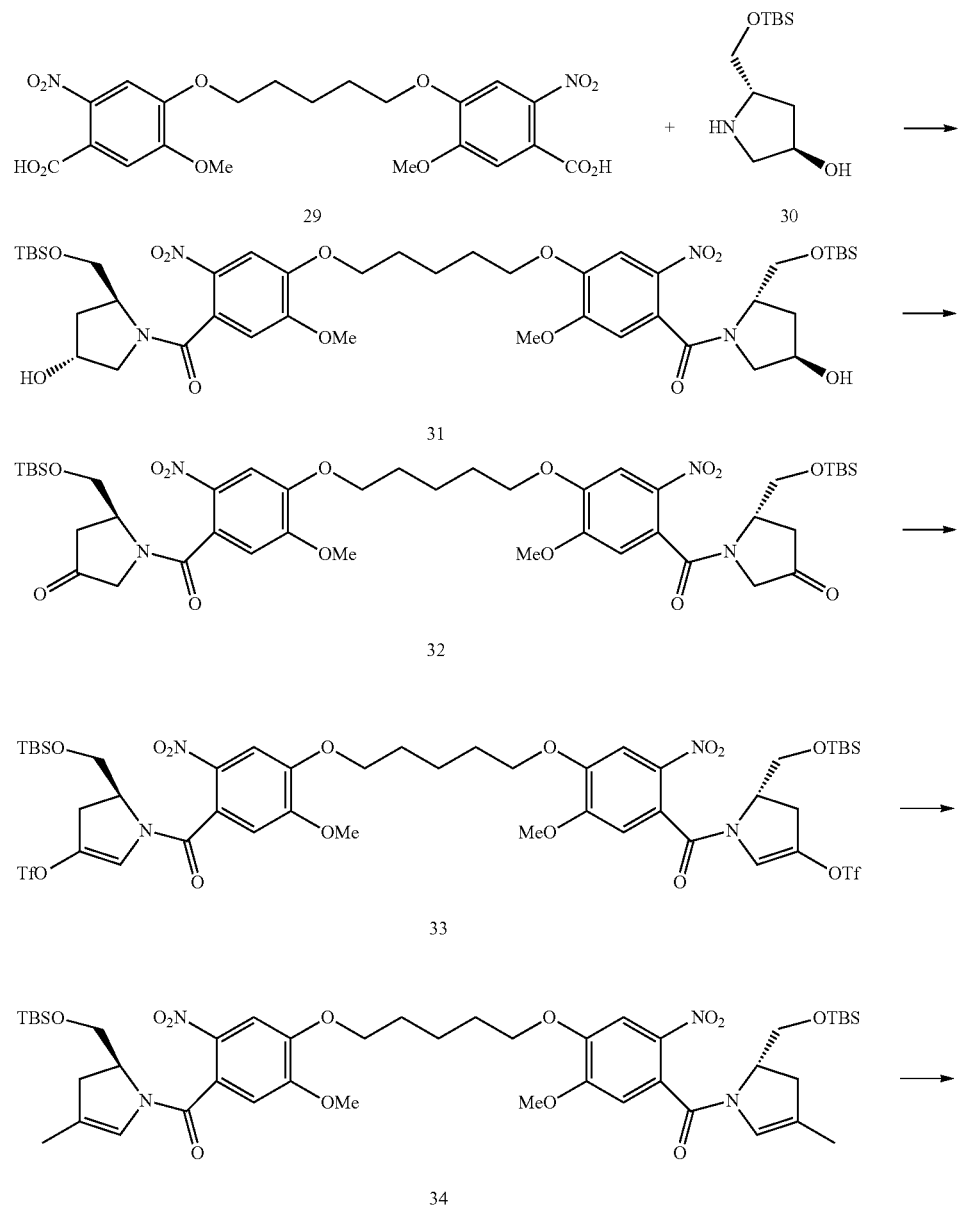

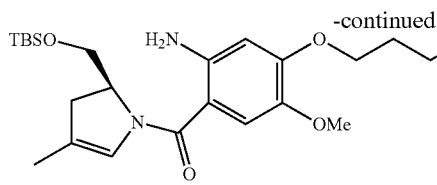
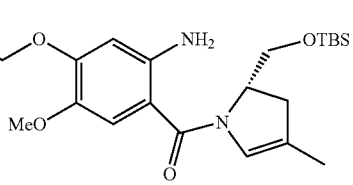

35

(a) (S,R)-((pentane-1,5-diylbis(oxy))bis(5-methoxy-2-nitro-4,1-phenylene))bis(((2S,4R)-2-(((tert-butyldimethylsilyl)oxy)methyl)-4-hydroxypyrrolidin-1-yl) methanone) (31)

Anhydrous DMF (approx. 0.5 mL) was added dropwise to a stirred suspension of 4,4'-(pentane-1,5-diylbis(oxy))bis(5-methoxy-2-nitrobenzoic acid) (29) (36.64 g, 74.0 mmol) and oxalyl chloride (18.79 mL, 0.222 mol, 3.0 eq.) in anhydrous DCM (450 mL) until vigorous effervescence occurred and the reaction mixture was left to stir overnight. The reaction mixture was evaporated to dryness, and triturated with diethyl ether. The resulting yellow precipitate was filtered from solution, washed with diethyl ether (100 mL) and immediately added to a solution of (3R,5S)-5-((tert-butyldimethylsilyloxy)methyl) pyrrolidin-3-ol (30) (39.40 g, 0.170 mol, 2.3 eq.) and anhydrous triethylamine (82.63 mL, 0.592 mol, 8 eq.) in anhydrous DCM (400 mL) at −40° C. The reaction mixture was allowed to slowly warm to room temperature (over 2.5 hours) after which, LCMS analysis indicated complete reaction. DCM (250 mL) was added and the mixture was transferred into a separating funnel. The organic layer was washed successively with 0.1M HCl (2×800 mL), saturated NaHCO$_3$ (500 mL) and brine (300 mL). After drying over MgSO$_4$ and filtration, evaporation of the solvent left the product as a yellow foam (62.8 g, 92%). LC/MS: RT 1.96 min; MS (ES+) m/z (relative intensity) 921.45 ([M+H]$^+$, 100).

(b) (5S,5'S)-1,1'-(4,4'-(pentane-1,5-diylbis(oxy))bis(5-methoxy-2-nitrobenzoyl))bis(5-(((tert-butyldimethylsilyl)oxy)methyl)pyrrolidin-3-one) (32)

Trichloroisocyanuric acid (21.86 g, 94.07 mmol, 1.4 eq) was added in one portion to a solution of diol 31 (61.90 g, 67.20 mmol) and TEMPO (2.10 g, 13.44 mmol, 0.2 eq) in anhydrous DCM (500 mL) under an atmosphere of argon at 0° C. The reaction mixture was stirred at 0° C. for 20 minutes after which, LCMS analysis of the reaction mixture showed complete reaction. The reaction mixture was diluted with DCM (400 mL) and washed with saturated sodium bicarbonate (500 mL), 0.2 M sodium thiosulfate solution (600 mL), brine (400 mL) and dried (MgSO$_4$). Evaporation of the solvent gave the crude product. Flash chromatography [gradient elution 80% n-hexane/20% ethyl acetate to 100% ethyl acetate] gave pure 31 as yellow solid (49.30 g, 80%). LC/MS: RT 2.03 min; MS (ES+) m/z (relative intensity) 917.55 ([M+H]$^+$, 100).

(c) (5S,5'S)-1,1'-(4,4'-(pentane-1, 5-diylbis(oxy))bis(5-methoxy-2-nitrobenzoyl))bis(5-(((tert-butyldimethylsilyl)oxy)methyl)-4,5-dihydro-1H-pyrrole-3,1-diyl)bis(trifluoromethanesulfonate), (33)

Triflic anhydride (24.19 mL, 0.144 mol, 6.0 eq) was added dropwise to a vigorously stirred solution of bis-ketone 31 (21.98 g, 23.96 mmol) in anhydrous DCM (400 mL) containing 2,6-lutidine (22.33 mL, 0.192 mol, 8.0 eq) at −40° C. The reaction mixture was stirred at −40° C. for 30 min after which, LCMS analysis indicated complete reaction. Reaction mixture was rapidly diluted with DCM (500 mL) and washed with ice-cold water (600 mL), ice-cold saturated sodium bicarbonate (400 mL) and brine (500 mL), dried over MgSO$_4$, filtered and evaporated to leave a crude brown oil. Flash chromatography [gradient elution 80% n-hexane/20% ethyl acetate to 66% n-hexane/33% ethyl acetate] gave pure 33 as a brown foam (16.40 g, 58%). LC/MS: RT 2.28 min; MS (ES+m/z (relative intensity) no data.

(d) (S)-((pentane-1,5-diylbis(oxy))bis(5-methoxy-2-nitro-4,1-phenylene))bis(((S)-2-(((tert-butyldimethylsilyl)oxy)methyl)-4-methyl-2,3-dihydro-1H-pyrrol-1-yl)methanone) (34)

Triflate 33 (5.06 g, 4.29 mmol), methyl boronic acid (1.80 g, 30.00 mmol, 7 eq) and triphenylarsine (1.05 g, 3.43 mmol, 0.8 eq) were dissolved in anhydrous dioxane and stirred under argon. Pd (II) bisbenzonitrile chloride was then added and the reaction mixture heated rapidly to 80° C. for 20 min. Reaction mixture cooled, filtered through Celite (washed through with ethyl acetate), filtrate washed with water (500 mL), brine (500 mL), dried over MgSO$_4$, filtered and evaporated. Flash chromatography [gradient elution 50% n-hexane/50% ethyl acetate] gave pure 34 as a brown foam (4.31 g, 59%). LC/MS: RT 2.23 min; MS (ES+) m/z (relative intensity) 913.50 ([M+H]$^+$, 100).

(e) (S)-((pentane-1,5-diylbis(oxy))bis(2-amino-5-methoxy-4,1-phenylene))bis(((S)-2-(((tert-butyldimethylsilyl)oxy)methyl)-4-methyl-2,3-dihydro-1H-pyrrol-1-yl)methanone) (35)

Zinc dust (26.48 g, 0.405 mol, 36.0 eq) was added in one portion to a solution of bis-nitro compound 34 (10.26 g, 11.24 mmol) in 5% formic acid/methanol (200 mL) keeping the temperature between 25-30° C. with the aid of a cold water bath. The reaction was stirred at 30° C. for 20 minutes after which, LCMS showed complete reaction. The reaction mixture was filtered through Celite to remove the excess zinc, which was washed with ethyl acetate (600 mL). The organic fractions were washed with water (500 mL), saturated sodium bicarbonate (500 mL) and brine (400 mL), dried over MgSO$_4$ and evaporated. Flash chromatography [gradient elution 100% chloroform to 99% chloroform/1% methanol] gave pure 35 as an orange foam (6.22 g, 65%). LC/MS: RT 2.20 min; MS (ES+) m/z (relative intensity) 853.50 ([M+H]$^+$, 100).

(ii) 4-((R)-2-((R)-2-(((allyloxy)carbonyl)amino)-3-methylbutanamido)propanamido)benzyl 4-((10R,13R)-10-isopropyl-13-methyl-8,11-dioxo-2,5-dioxa-9,12-diazatetradecanamido)benzyl ((S)-(pentane-1,5-diylbis(oxy))bis(2-((S)-2-(hydroxymethyl)-4-methyl-2,3-dihydro-1H-pyrrole-1-carbonyl)-4-methoxy-5,1-phenylene))dicarbamate (40)
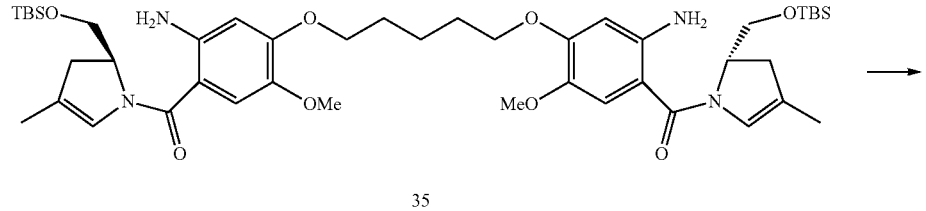
35
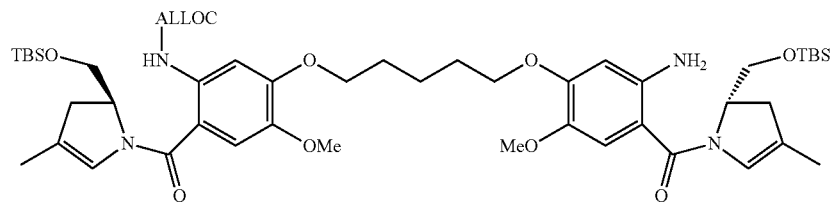
36
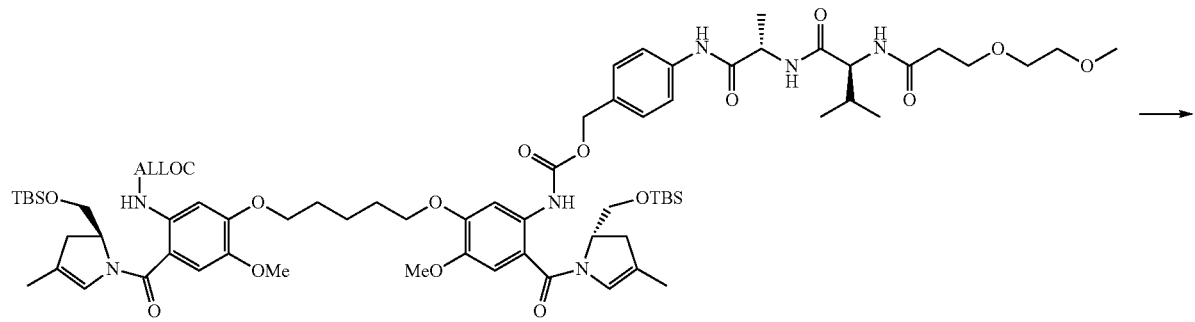
37
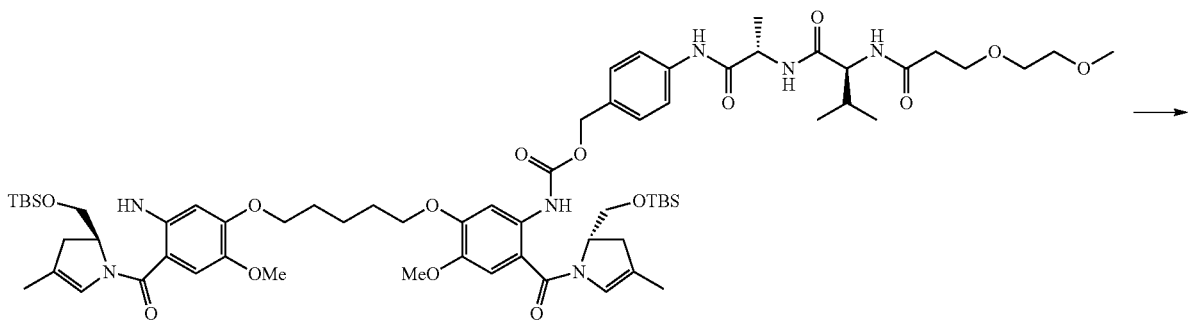
38

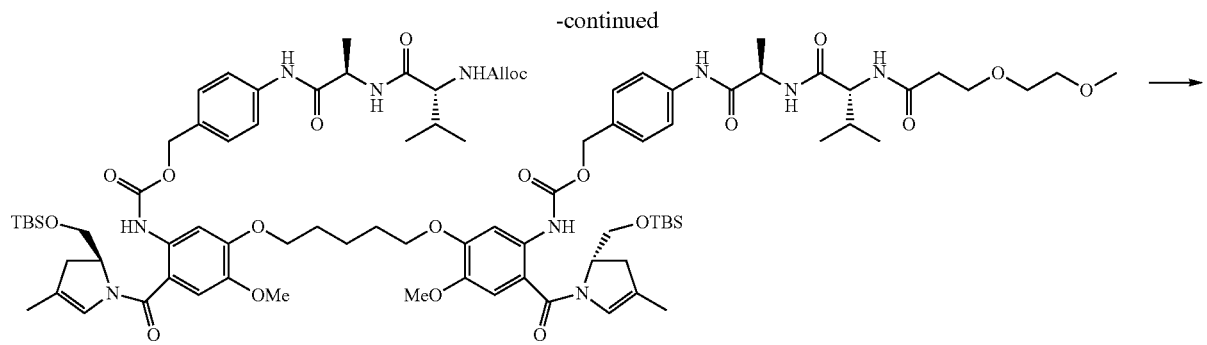

39

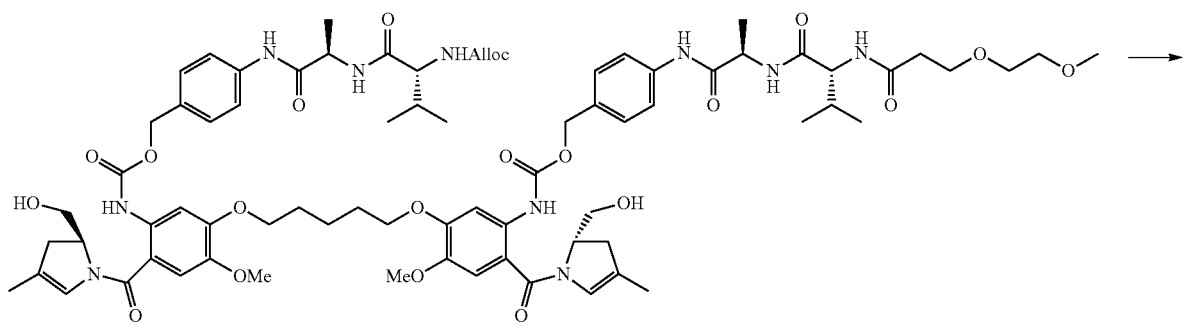

40

(a) Allyl (5-((5-(5-amino-4-((S)-2-(((tert-butydimethysily)oxy)methyl)-4-methy-2,3-dihydro-1H-pyrrole-1-carbonyl)-2-methoxyphenoxy)pentyl)oxy)-2-((S)-2-(((tert -butyldimethylsilyl)oxy)methyl)-4-methyl-2,3-dihydro-1H-pyrrole-1-carbonyl)-4-methoxyphenyl)carbamate (36)

Pyridine (1.156 mL, 14.30 mmol, 1.5 eq) was added to a solution of the bis-aniline 35 (8.14 g, 9.54 mmol) in anhydrous DCM (350 mL) at −78° C. under an atmosphere of argon. After 5 minutes, allyl chloroformate (0.911 mL, 8.58 mmol, 0.9 eq) was added and the reaction mixture allowed to warm to room temperature. The reaction mixture was diluted with DCM (250 mL), washed with saturated CuSO₄ solution (400 mL), saturated sodium bicarbonate (400 mL) and brine (400 mL), dried over MgSO₄. Flash chromatography [gradient elution 66% n-hexane/33% ethyl acetate to 33% n-hexane/66% ethyl acetate] gave pure 36 as an orange foam (3.88 g, 43%). LC/MS: RT 2.27 min; MS (ES+) m/z (relative intensity) 937.55 ([M+H]$^+$, 100).

(b) Allyl 4-((10S,13S)-10-isopropyl-13-methyl-8,11-dioxo-2,5-dioxa-9,12-diazatetradecanamido)benzyl ((S)-(pentane-1, 5-diylbis(oxy))bis(2-((S)-2-(((tert -butyldimethylsilyl)oxy)methyl)-4-methyl-2,3-dihydro-1H-pyrrole-1-carbonyl)-4-methoxy-5,1-phenylene))dicarbamate (37)

Triethylamine (0.854 mL, 6.14 mmol, 2.2 eq) was added to a stirred solution of the aniline 36 (2.62 g, 2.79 mmol) and triphosgene (0.30 g, 1.00 mmol, 0.36 eq) in anhydrous THF (50 mL) under argon 0° C. The reaction mixture was stirred at room temperature for 5 minutes. LCMS analysis of an aliquot quenched with methanol, showed formation of the isocyanate. A solution of mPEG₂-Val-Ala-PAB-OH (1.54 g, 3.63 mmol, 1.3 eq) and triethylamine (0.583 mL, 4.19 mmol, 1.5 eq) in dry THF (50 mL) was added in one portion and the resulting mixture was stirred overnight at 40° C. The solvent of the reaction mixture was evaporated leaving a crude product. Flash chromatography [gradient elution 100% chloroform to 98% chloroform/2% methanol] gave pure 37 as a light orange solid (2.38 g, 62%). LC/MS: RT 2.29 min; MS (ES+) m/z (relative intensity) no data.

(c) 4-((10S,13S)-10-isopropyl-13-methyl-8,11-dioxo-2,5-dioxa-9,12-diazatetradecanamido)benzyl (5-((5-(5-amino-4-((S)-2-(((tert-butyldimethylsilyl) oxy)methyl)-4-methyl-2,3-dihydro-1H-pyrrole-1-carbonyl)-2-methoxyphenoxy)pentyl)oxy)-2-((S)-2-(((tert -butyldimethylsilyl)oxy)methyl)-4-methyl-2, 3-dihydro-1H-pyrrole-1-carbonyl)-4-methoxyphenyl)carbamate (38)

Tetrakis(triphenylphosphine)palladium (39 mg, 0.034 mmol, 0.02 eq) was added to a stirred solution of 37 (2.35 g, 1.69 mmol) and pyrrolidine (0.35 mL, 4.24 mmol, 2.5 eq) in anhydrous DCM (25 mL) under argon at room temperature. Reaction mixture allowed to stir for 45 min then diluted with DCM (100 mL), washed with saturated ammonium chloride solution (100 mL), brine (100 mL), dried over MgSO₄, filtered and evaporated. Flash chromatography [gradient elution 100% chloroform to 95% chloroform/5% methanol] gave pure 38 as a yellow solid (1.81 g, 82%). LC/MS: RT 2.21 min; MS (ES+) m/z (relative intensity) 1303.65 ([M+H]$^+$, 100).

(d) 4-((R)-2-((R)-2-(((allyloxy)carbonyl)amino)-3-methylbutanamido)propanamido)benzyl 4-((10R,13R)-10-isopropyl-13-methyl-8,11-dioxo-2,5-dioxa-9,12-diazatetradecanamido)benzyl ((S)-(pentane-1,5-diylbis(oxy))bis(2-((S)-2-(((tert-butydimethysily)oxy)methy)-4-methy-2,3-dihydro-1H-pyrrole-1-carbonyl)-4-methoxy-5,1-phenylene))dicarbamate (39)

Triethylamine (0.419 mL, 3.01 mmol, 2.2 eq) was added to a stirred solution of the aniline 38 (1.78 g, 1.37 mmol) and triphosgene (0.15 g, 0.49 mmol, 0.36 eq) in anhydrous THF (50 mL) under argon 0° C. The reaction mixture was stirred at room temperature for 5 min. LCMS analysis of an aliquot quenched with methanol, showed formation of the isocyanate. A solution of Alloc-Val-Ala-PAB-OH (0.67 g, 1.78 mmol, 1.3 eq) and triethylamine (0.29 mL, 2.05 mmol, 1.5 eq) in dry THF (45 mL) was added in one portion and the resulting mixture was stirred overnight at 40° C. The solvent of the reaction mixture was evaporated leaving a crude product. Flash chromatography [gradient elution 100% ethyl acetate to 97% ethyl acetate/3% methanol] gave pure 39 as a pale yellow solid (1.33 g, 57%). LC/MS: RT 2.21 min; MS (ES+) m/z (relative intensity) no data.

(e) 4-((R)-2-((R)-2-(((allyloxy)carbonyl)amino)-3-methylbutanamido)propanamido)benzyl 4-((10R,13R)-10-isopropyl-13-methyl-8,11-dioxo-2,5-dioxa-9,12-diazatetradecanamido)benzyl ((S)-(pentane-1,5-diylbis(oxy))bis(2-((S)-2-(hydroxymethyl)-4-methyl-2,3-dihydro-1H-pyrrole-1-carbonyl)-4-methoxy-5,1-phenylene))dicarbamate (40)

Tetra-n-butylammonium fluoride (1 M, 1.52 mL, 1.52 mmol, 2.0 eq) was added to a solution of the TBS protected compound 39 (1.30 g, 0.76 mmol) in anhydrous THF (15 mL). The reaction mixture was stirred at room temperature for 4 hours. The reaction mixture was diluted with chloroform (100 mL) and washed sequentially with water (40 mL) and brine (40 mL). The organic phase was dried over $MgSO_4$ and evaporated to leave a yellow solid. Flash chromatography [gradient elution 95% ethyl acetate/5% methanol to 90% ethyl acetate/10% methanol] gave pure 40 as a pale yellow solid (1.00 g, 89%). LC/MS: RT 1.60 min; MS (ES+) m/z (relative intensity) 1478.45 (100).

(iii) (11S,11aS)-4-((2R,5R)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-1,11a-dihydro-1H-pyrrolo[2,1-c][1,4]benzodiazepine-10 (5H)-carboxylate (43)

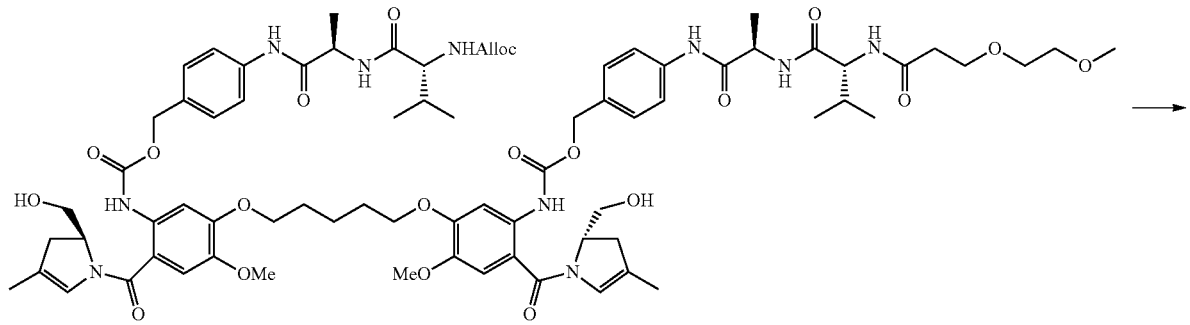

40

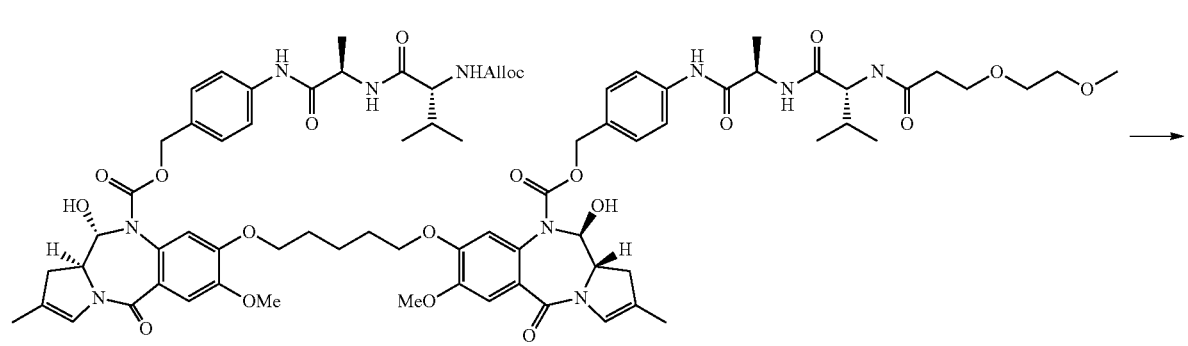

41

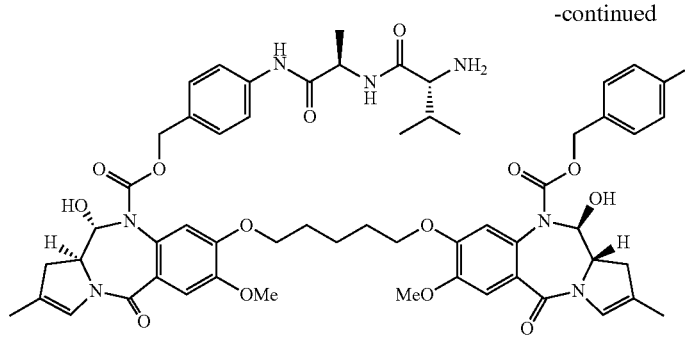

42

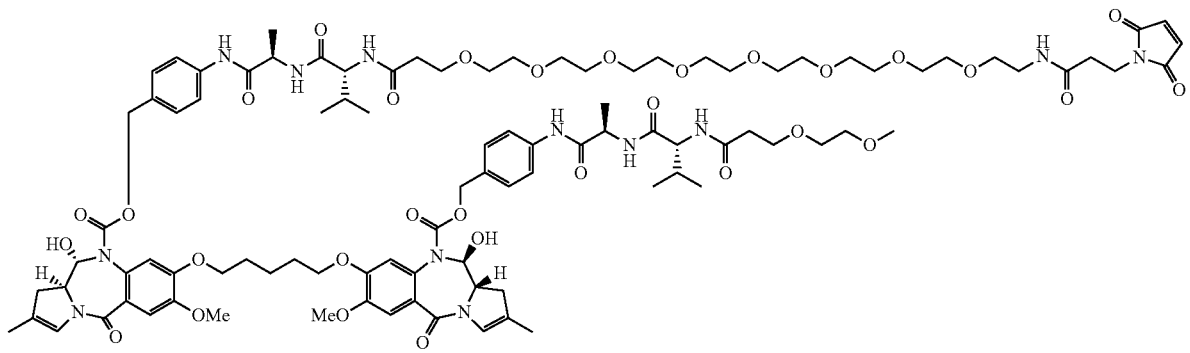

43

(a) (11S,11aS)-4-((R)-2-((R)-2-(((allyloxy)carbonyl)amino)-3-methylbutanamido)propanamido)benzyl 11-hydroxy-8-((5-(((11S,11aS)-11-hydroxy-10-(((4-((10R,13R)-10-isopropyl-1,3-methyl-8,11-dioxo-2,5-dioxa-9, 12-diazatetradecanamido)benzyl)oxy)carbonyl)-7-methoxy-2-methyl-5-oxo-5,10,11, 11a -tetrahydro-1H-pyrrolo[2, 1-c][1,4]benzodiazepin-8-yl)oxy)pentyl) oxy)-7-methoxy-2-methyl-5-oxo-11,11a-dihydro-1H-pyrrolo[2, 1-c][1,4]benzodiazepine-10 (5H)-carboxylate (41)

Dess-Martin periodinane (0.59 g, 1.38 mmol, 2.1 eq) was added to a stirred solution of 40 (0.97 g, 0.66 mmol) in anhydrous DCM under argon at room temperature. The reaction mixture was allowed to stir for 4 hours. Reaction mixture diluted with DCM (100 mL), washed with saturated sodium bicarbonate solution (3×100 mL), water (100 mL), brine (100 mL), dried over MgSO$_4$, filtered and evaporated. Flash chromatography [gradient elution 100% chloroform to 95% chloroform/5% methanol] gave pure 41 as a pale yellow solid (0.88 g, 90%). LC/MS: RT 1.57 min; MS (ES+) m/z (relative intensity) 1473.35 (100).

(b) (11S,11aS)-4-((R)-2-((R)-2-amino-3-methylbutanamido)propanamido)benzyl 11-hydroxy-8-((5-(((11S,11aS)-11-hydroxy-10-((4-((((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10 (5H)-carboxylate (42)

Tetrakis(triphenylphosphine)palladium (5 mg, 0.004 mmol, 0.06 eq) was added to a solution of 41 (105 mg, 0.071 mmol) and pyrrolidine (7 µL, 0.086 mmol, 1.2 eq) in anhydrous DCM (5 mL). The reaction mixture was stirred 15 minutes then diluted with chloroform (50 mL) and washed sequentially with saturated aqueous ammonium chloride (30 mL) and brine (30 mL). The organic phase was dried over magnesium sulphate, filtered and evaporated. Flash chromatography [gradient elution 100% chloroform to 90% chloroform/10% methanol] gave pure 42 as a pale yellow solid (54 mg, 55%). LC/MS: RT 1.21 min; MS (ES+) m/z (relative intensity) 1389.50 (100).

(c) (11S,11aS)-4-((2R,5R)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-8-((5-(((11S,11aS)-11-hydroxy-10-(((4-((((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10 (5H) -carboxylate (43)

N-(3-Dimethylaminopropyl)-N'-ethylcarbodiimide (28 mg, 0.146 mmol, 1 eq) was added to a solution of 42 (203 mg, 0.146 mmol) and maleimide-PEG$_8$ acid (87 mg, 0.146 mmol) in chloroform (5 mL). The reaction was stirred for 1.5 h then diluted with chloroform (50 mL), washed with water (50 mL), brine (30 mL), dried over magnesium sulphate, filtered and evaporated. Flash chromatography [gradient elution 100% DCM to 90% DCM/10% methanol] gave 43 as a pale yellow solid (205 mg, 72%). LC/MS: RT 5.75 min; MS (ES+) m/z (relative intensity) 982.90 (100), 1963.70 (5).

General Experimental Methods for Example 5

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B over 2.5 min. The composition was held for 0.5 min at 95% B, and then returned to 5% B in 0.1 minutes and held there for 0.9 min. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm Example 5

(i) (S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone (59)

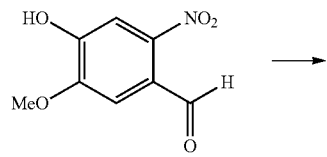

51

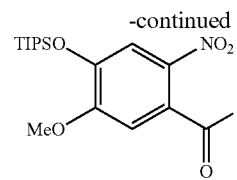

52

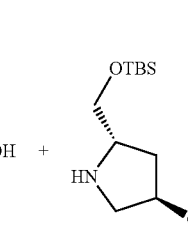

53 54

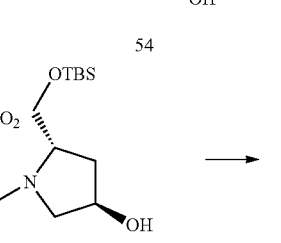

55

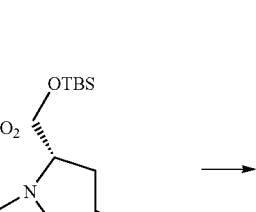

56

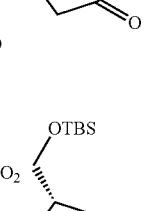

57

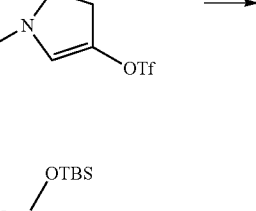

58

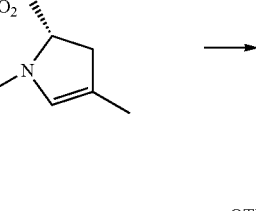

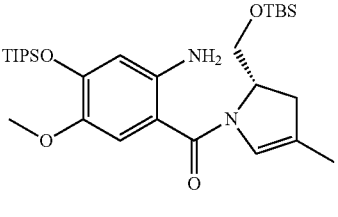

59

(a) 5-methoxy-2-nitro-4-((triisopropylsilyl)oxy)benzaldehyde (52)

Neat triisopropylsilylchloride (56.4 mL, 262 mmol) was added to a mixture of imidazole (48.7 g, 715.23 mmol) and 4-hydroxy-5-methoxy-2-nitrobenzaldehyde 51 (47 g, 238 mmol) (ground together). The mixture was heated until the phenol and imidazole melted and went into solution (100° C.). The reaction mixture was allowed to stir for 15 minutes and was then allowed to cool, whereupon a solid was observed to form at the bottom of the flask (imidazole chloride). The reaction mixture was diluted with 5% EtOAc/hexanes and loaded directly onto silica gel and the pad was eluted with 5% EtOAc/hexanes, followed by 10% EtOAc/hexanes (due to the low excess, very little unreacted TIPSCI was found in the product). The desired product was eluted with 5% ethyl acetate in hexane. Excess eluent was removed by rotary evaporation under reduced pressure, followed by drying under high vacuum to afford a crystalline light sensitive solid (74.4 g, 88%). Purity satisfactory by LC/MS (4.22 min (ES+) m/z (relative intensity) 353.88 ([M+H]$^{+\cdot}$, 100)); $^1$H NMR (400 MHz, CDCl$_3$) δ 10.43 (s, 1H), 7.60 (s, 1H), 7.40 (s, 1H), 3.96 (s, 3H), 1.35-1.24 (m, 3H), 1.10 (m, 18H).

(b) 5-methoxy-2-nitro-4-((triisopropylsilyl)oxy)benzoic acid (53)

A solution of sodium chlorite (47.3 g, 523 mmol, 80% technical grade) and sodium dihydrogenphosphate monobasic (35.2 g, 293 mmol) (NaH$_2$PO$_4$) in water (800 mL) was added to a solution of compound 52 (74 g, 209 mmol) in tetrahydrofuran (500 mL) at room temperature. Hydrogen peroxide (60% w/w, 140 mL, 2.93 mol) was immediately added to the vigorously stirred biphasic mixture. The reaction mixture evolved gas (oxygen), the starting material dissolved and the temperature of the reaction mixture rose to 45° C. After 30 minutes LC/MS revealed that the reaction was complete. The reaction mixture was cooled in an ice bath and hydrochloric acid (1 M) was added to lower the pH to 3 (this step was found unnecessary in many instances, as the pH at the end of the reaction is already acidic; please check the pH before extraction). The reaction mixture was then extracted with ethyl acetate (1 L) and the organic phases washed with brine (2×100 mL) and dried over magnesium sulphate. The organic phase was filtered and excess solvent removed by rotary evaporation under reduced pressure to afford the product 53 in quantitative yield as a yellow solid. LC/MS (3.93 min (ES−) m/z (relative intensity) 367.74 ([M−H]$^{-\cdot}$, 100)); $^1$H NMR (400 MHz, CDCl$_3$) δ 7.36 (s, 1H), 7.24 (s, 1H), 3.93 (s, 3H), 1.34-1.22 (m, 3H), 1.10 (m, 18H).

(c) ((2S,4R)-2-(((tert-butyldimethylsilyl)oxy)methyl)-4-hydroxypyrrolidin-1-yl) (5-methoxy-2-nitro-4-((triisopropylsilyl)oxy)phenyl)methanone (55)

DCC (29.2 g, 141 mmol, 1.2 eq) was added to a solution of acid 53 (43.5 g, 117.8 mmol, 1 eq), and hydroxybenzotriazole hydrate (19.8 g, 129.6 mmol, 1.1 eq) in dichloromethane (200 mL) at 0° C. The cold bath was removed and the reaction was allowed to proceed for 30 mins at room temperature, at which time a solution of (2S,4R)-2-t-butyldimethylsilyloxymethyl-4-hydroxypyrrolidine 54 (30 g, 129.6 mmol, 1.1 eq) and triethylamine (24.66 mL, 176 mmol, 1.5 eq) in dichloromethane (100 mL) was added rapidly at −10° C. under argon (on large scale, the addition time could be shortened by cooling the reaction mixture even further. The reaction mixture was allowed to stir at room temperature for 40 minutes to 1 hour and monitored by LC/MS and TLC (EtOAc). The solids were removed by filtration over celite and the organic phase was washed with cold aqueous 0.1 M HCl until the pH was measured at 4 or 5. The organic phase was then washed with water, followed by saturated aqueous sodium bicarbonate and brine. The organic layer was dried over magnesium sulphate, filtered and excess solvent removed by rotary evaporation under reduced pressure. The residue was subjected to column flash chromatography (silica gel; gradient 40/60 ethyl acetate/hexane to 80/20 ethyl acetate/hexane). Excess solvent was removed by rotary evaporation under reduced pressure afforded the pure product 55, (45.5 g of pure product 66%, and 17 g of slightly impure product, 90% in total). LC/MS 4.43 min (ES+) m/z (relative intensity) 582.92 ([M+H]$^{+\cdot}$, 100); $^1$H NMR (400 MHz, CDCl$_3$) δ 7.66 (s, 1H), 6.74 (s, 1H), 4.54 (s, 1H), 4.40 (s, 1H), 4.13 (s, 1H), 3.86 (s, 3H), 3.77 (d, J=9.2 Hz, 1H), 3.36 (dd, J=11.3, 4.5 Hz, 1H), 3.14-3.02 (m, 1H), 2.38-2.28 (m, 1H), 2.10 (ddd, J=13.3, 8.4, 2.2 Hz, 1H), 1.36-1.19 (m, 3H), 1.15-1.05 (m, 18H), 0.91 (s, 9H), 0.17-0.05 (m, 6H), (presence of rotamers).

(d) (S)-5-(((tert-butyldimethylsilyl)oxy)methyl)-1-(5-methoxy-2-nitro-4-((triisopropylsilyl)oxy)benzoyl)pyrrolidin-3-one (56)

TCCA (8.82 g, 40 mmol, 0.7 eq) was added to a stirred solution of 55 (31.7 g, 54 mmol, 1 eq) and TEMPO (0.85 g, 5.4 mmol, 0.1 eq) in dry dichloromethane (250 mL) at 0° C. The reaction mixture was vigorously stirred for 20 minutess, at which point TLC (50/50 ethyl acetate/hexane) revealed complete consumption of the starting material. The reaction mixture was filtered through celite and the filtrate washed with aqueous saturated sodium bicarbonate (100 mL), sodium thiosulphate (9 g in 300 mL), brine (100 mL) and dried over magnesium sulphate. Rotary evaporation under reduced pressure afforded product 6 in quantitative yield. LC/MS 4.52 min (ES+) m/z (relative intensity) 581.08 ([M+H]$^{+\cdot}$, 100); $^1$H NMR (400 MHz, CDCl$_3$) δ 7.78-7.60 (m, 1H), 6.85-6.62 (m, 1H), 4.94 (dd, J=30.8, 7.8 Hz, 1H), 4.50-4.16 (m, 1H), 3.99-3.82 (m, 3H), 3.80-3.34 (m, 3H), 2.92-2.17 (m, 2H), 1.40-1.18 (m, 3H), 1.11 (t, J=6.2 Hz, 18H), 0.97-0.75 (m, 9H), 0.15-−0.06 (m, 6H), (presence of rotamers).

(e) (S)-5-(((tert-butyldimethylsilyl)oxy)methyl)-1-(5-methoxy-2-nitro-4-((triisopropylsilyl)oxy)benzoyl)-4, 5-dihydro-1H-pyrrol-3-yl trifluoromethanesulfonate (57)

Triflic anhydride (27.7 mL, 46.4 g, 165 mmol, 3 eq) was injected (temperature controlled) to a vigorously stirred suspension of ketone 56 (31.9 g, 55 mmol, 1 eq) in dry dichloromethane (900 mL) in the presence of 2,6-lutidine (25.6 mL, 23.5 g, 220 mmol, 4 eq, dried over sieves) at −50° C. (acetone/dry ice bath). The reaction mixture was allowed to stir for 1.5 hours when LC/MS, following a mini work-up (water/dichloromethane), revealed the reaction to be complete. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel;

10/90 v/v ethyl acetate/hexane), removal of excess eluent afforded the product 57 (37.6 g, 96%) LC/MS, method 2, 4.32 min (ES+) m/z (relative intensity) 712.89 ([M+H]+·, 100); ¹H NMR (400 MHz, CDCl₃) δ 7.71 (s, 1H), 6.75 (s, 1H), 6.05 (d, J=1.8 Hz, 1H), 4.78 (dd, J=9.8, 5.5 Hz, 1H), 4.15-3.75 (m, 5H), 3.17 (ddd, J=16.2, 10.4, 2.3 Hz, 1H), 2.99 (ddd, J=16.3, 4.0, 1.6 Hz, 1H), 1.45-1.19 (m, 3H), 1.15-1.08 (m, 18H), 1.05 (s, 6H), 0.95-0.87 (m, 9H), 0.15-0.08 (m, 6H).

(f) (S)-(2-(((tert-butyldimethylsilyl)oxy)methyl)-4-methyl-2,3-dihydro-1H-pyrrol-1-yl) (5-methoxy-2-nitro-4-((triisopropylsilyl)oxy)phenyl)methanone (58)

Triphenylarsine (1.71 g, 5.60 mmol, 0.4 eq) was added to a mixture of triflate 57 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(II) chloride (540 mg, 1.40 mmol, 0.1 eq) was added. The reaction was flushed with argon 3 more times before being warmed instantaneously to 110° C. (the drysyn heating block was previously warmed to 110° C. prior addition of the flask). After 10 mins the reaction was cooled to room temperature and filtered through a pad celite. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 58 (4.5 g, 55%). LC/MS, 4.27 min (ES+) m/z (relative intensity) 579.18 ([M+H]+·, 100); ¹H NMR (400 MHz, CDCl₃) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(g) (S)-(2-amino-5-methoxy-4-((triisopropylsilyl)oxy)phenyl) (2-(((tert-butyldimethylsilyl)oxy)methyl)-4-methyl-2,3-dihydro-1H-pyrrol-1-yl)methanone (59)

Zinc powder (28 g, 430 mmol, 37 eq) was added to a solution of compound 58 (6.7 g, 11.58 mmol) in 5% formic acid in ethanol v/v (70 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 59 (5.1 g, 80%). LC/MS, 4.23 min (ES+) m/z (relative intensity) 550.21 ([M+H]+·, 100); ¹H NMR (400 MHz, CDCl₃) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03--0.03 (m, J=6.2 Hz, 6H).

(ii) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate

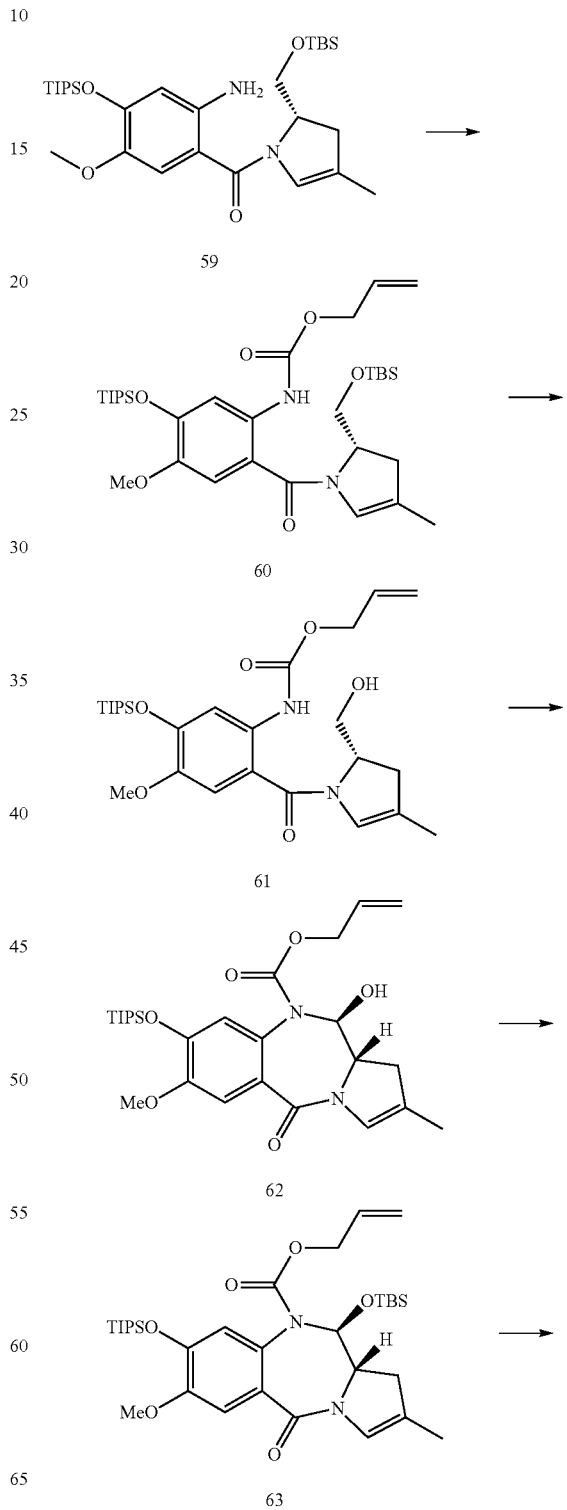

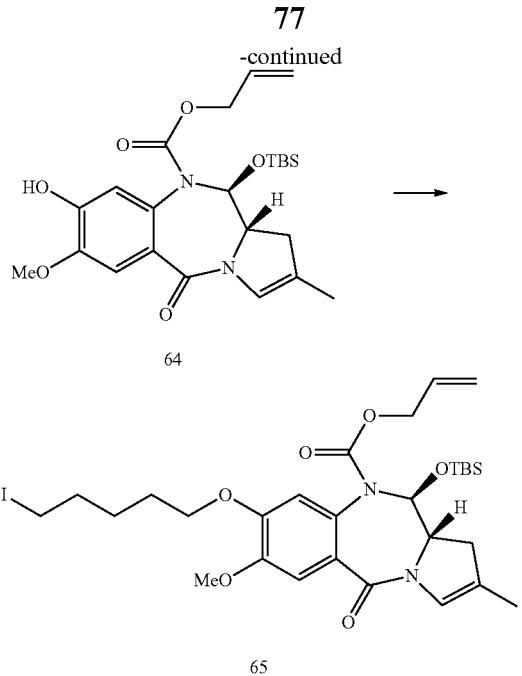

(a) (S)-allyl (2-(2-(((tert-butyldimethylsilyl)oxy)methyl)-4-methyl-2,3-dihydro-1H-pyrrole-1-carbonyl)-4-methoxy-5-((triisopropylsilyl)oxy)phenyl) carbamate (60)

Allyl chloroformate (0.30 mL, 3.00 mmol, 1.1 eq) was added to a solution of amine 59 (1.5 g, 2.73 mmol) in the presence of dry pyridine (0.48 mL, 6.00 mmol, 2.2 eq) in dry dichloromethane (20 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 60 which was used directly in the next reaction. LC/MS, 4.45 min (ES+) m/z (relative intensity) 632.91 ([M+H]+·, 100)

(b) (S)-allyl (2-(2-(hydroxymethyl)-4-methyl-2,3-dihydro-1H-pyrrole-1-carbonyl)-4-methoxy-5-((triisopropylsilyl)oxy)phenyl)carbamate (61)

The crude 60 was dissolved in a 7:1:1:2 mixture of acetic acid/methanol/tetrahydrofuran/water (28:4:4:8 mL) and allowed to stir at room temperature.
After 3 hours, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel, 25% ethyl acetate in hexane). Pure fractions were collected and combined and excess eluent was removed by rotary evaporation under reduced pressure to afford the desired product 61 (1 g, 71%). LC/MS, 3.70 min (ES+) m/z (relative intensity) 519.13 ([M+H]+·, 95); $^1$H NMR (400 MHz, CDCl$_3$) δ 8.34 (s, 1H), 7.69 (s, 1H), 6.78 (s, 1H), 6.15 (s, 1H), 5.95 (ddt, J=17.2, 10.5, 5.7 Hz, 1H), 5.33 (dq, J=17.2, 1.5 Hz, 1H), 5.23 (ddd, J=10.4, 2.6, 1.3 Hz, 1H), 4.73 (tt, J=7.8, 4.8 Hz, 1H), 4.63 (dt, J=5.7, 1.4 Hz, 2H), 4.54 (s, 1H), 3.89-3.70 (m, 5H), 2.87 (dd, J=16.5, 10.5 Hz, 1H), 2.19 (dd, J=16.8, 4.6 Hz, 1H), 1.70 (d, J=1.3 Hz, 3H), 1.38-1.23 (m, 3H), 1.12 (s, 10H), 1.10 (s, 8H).

(c) (11S,11aS)-allyl 11-hydroxy-7-methoxy-2-methyl-5-oxo-8-((triisopropylsilyl)oxy)-11,11a -dihydro-1H-benzo[e]pyrrolo[1,2-a][1,4]diazepine-10(5H)-carboxylate (62)

Dimethyl sulphoxide (0.35 mL, 4.83 mmol, 2.5 eq) was added dropwise to a solution of oxalyl chloride (0.2 mL, 2.32 mmol, 1.2 eq) in dry dichloromethane (10 mL) at −78° C. (dry ice /acetone bath) under an atmosphere of argon. After 10 minutes a solution of 61 (1 g, 1.93 mmol) in dry dichloromethane (8 mL) was added slowly with the temperature still at −78° C. After 15 min triethylamine (1.35 mL, dried over 4 Å molecular sieves, 9.65 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 62 (658 mg, 66%). LC/MS, 3.52 min (ES+) m/z (relative intensity) 517.14 ([M+H]+·, 100); $^1$H NMR (400 MHz, CDCl$_3$) δ 7.20 (s, 1H), 6.75-6.63 (m, J=8.8, 4.0 Hz, 2H), 5.89-5.64 (m, J=9.6, 4.1 Hz, 2H), 5.23-5.03 (m, 2H), 4.68-4.38 (m, 2H), 3.84 (s, 3H), 3.83-3.77 (m, 1H), 3.40 (s, 1H), 3.05-2.83 (m, 1H), 2.59 (d, J=17.1 Hz, 1H), 1.78 (d, J=1.3 Hz, 3H), 1.33-1.16 (m, 3H), 1.09 (d, J=2.2 Hz, 9H), 1.07 (d, J=2.1 Hz, 9H).

(d) (11S,11aS)-allyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H) -carboxylate (63)

Tert-butyldimethylsilyltriflate (0.70 mL, 3.00 mmol, 3 eq) was added to a solution of compound 62 (520 mg, 1.00 mmol) and 2,6-lutidine (0.46 mL, 4.00 mmol, 4 eq) in dry dichloromethane (40 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 63 (540 mg, 85%). LC/MS, 4.42 min (ES+) m/z (relative intensity) 653.14 ([M+Na]+·, 100); $^1$H NMR (400 MHz, CDCl$_3$) δ 7.20 (s, 1H), 6.71-6.64 (m, J=5.5 Hz, 2H), 5.83 (d, J=9.0 Hz, 1H), 5.80-5.68 (m, J=5.9 Hz, 1H), 5.14-5.06 (m, 2H), 4.58 (dd, J=13.2, 5.2 Hz, 1H), 4.36 (dd, J=13.3, 5.5 Hz, 1H), 3.84 (s, 3H), 3.71 (td, J=10.1, 3.8 Hz, 1H), 2.91 (dd, J=16.9, 10.3 Hz, 1H), 2.36 (d, J=16.8 Hz, 1H), 1.75 (s, 3H), 1.31-1.16 (m, 3H), 1.12-1.01 (m, J=7.4, 2.1 Hz, 18H), 0.89-0.81 (m, 9H), 0.25 (s, 3H), 0.19 (s, 3H).

(e) (11S,11aS)-allyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (64)

Lithium acetate (87 mg, 0.85 mmol) was added to a solution of compound 63 (540 mg, 0.85 mmol) in wet dimethylformamide (6 mL, 50:1 DMF/water). After 4 hours, the reaction was complete and the reaction mixture was diluted with ethyl acetate (25 mL) and washed with aqueous citric acid solution (pH ~3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 64 (400 mg, quantitative). LC/MS, (3.33 min (ES+) m/z (relative intensity) 475.26 ([M+H]$^+$, 100).

(f) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate (65)

Diiodopentane (0.63 mL, 4.21 mmol, 5 eq) and potassium carbonate (116 mg, 0.84 mmol, 1 eq) were added to a solution of phenol 64 (400 mg, 0.84 mmol) in acetone (4 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate,). Pure fractions were collected and combined and excess eluent was removed to provide 15 in 90% yield. LC/MS, 3.90 min (ES+) m/z (relative intensity) 670.91 ([M]$^+$, 100). $^1$H NMR (400 MHz, CDCl$_3$) δ 7.23 (s, 1H), 6.69 (s, 1H), 6.60 (s, 1H), 5.87 (d, J=8.8 Hz, 1H), 5.83-5.68 (m, J=5.6 Hz, 1H), 5.15-5.01 (m, 2H), 4.67-4.58 (m, 1H), 4.45-4.35 (m, 1H), 4.04-3.93 (m, 2H), 3.91 (s, 3H), 3.73 (td, J=10.0, 3.8 Hz, 1H), 3.25-3.14 (m, J=8.5, 7.0 Hz, 2H), 2.92 (dd, J=16.8, 10.3 Hz, 1H), 2.38 (d, J=16.8 Hz, 1H), 1.95-1.81 (m, 4H), 1.77 (s, 3H), 1.64-1.49 (m, 2H), 0.88 (s, 9H), 0.25 (s, 3H), 0.23 (s, 3H).

(iii) (11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (70)

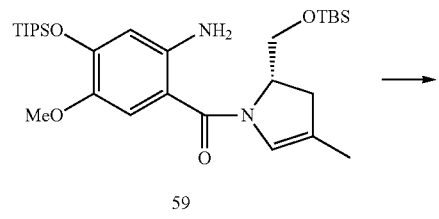

59

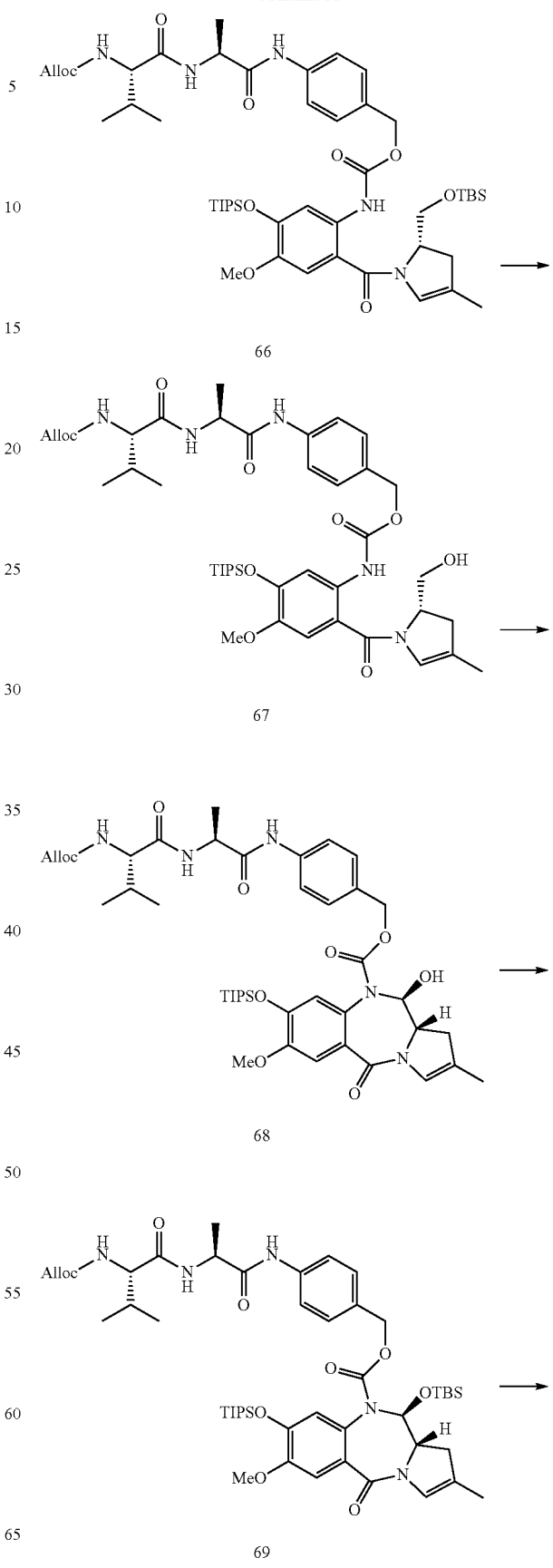

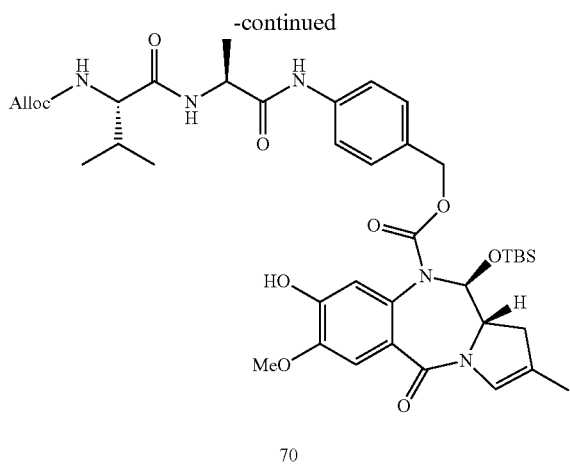

70

(a) Allyl 3-(2-(2-(4-(((((2-((S)-2-(((tert-butyldimethylsilyl)oxy)methyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate (66)

Triethylamine (2.23 mL, 18.04 mmol, 2.2 eq) was added to a stirred solution of the amine 59 (4 g, 8.20 mmol) and triphosgene (778 mg, 2.95 mmol, 0.36 eq) in dry tetrahydrofuran (40 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (4.12 g, 12.30 mmol, 1.5 eq) and triethylamine (1.52 mL, 12.30 mmol, 1.5 eq) in dry tetrahydrofuran (40 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 66 (3.9 g, 50%). LC/MS, 4.23 min (ES+) m/z (relative intensity) 952.36 ([M+H]$^{+\cdot}$, 100); $^1$H NMR (400 MHz, CDCl$_3$) δ 8.62 (br s, 1H), 8.46 (s, 1H), 7.77 (br s, 1H), 7.53 (d, J=8.4 Hz, 2H), 7.32 (d, J=8.5 Hz, 2H), 6.76 (s, 1H), 6.57 (d, J=7.6 Hz, 1H), 6.17 (s, 1H), 6.03-5.83 (m, 1H), 5.26 (dd, J=33.8, 13.5 Hz, 3H), 5.10 (s, 2H), 4.70-4.60 (m, 2H), 4.58 (dd, J=5.7, 1.3 Hz, 2H), 4.06-3.99 (m, 1H), 3.92 (s, 1H), 3.82-3.71 (m, 1H), 3.75 (s, 3H), 2.79-2.64 (m, 1H), 2.54 (d, J=12.9 Hz, 1H), 2.16 (dq, J=13.5, 6.7 Hz, 1H), 1.67 (s, 3H), 1.46 (d, J=7.0 Hz, 3H), 1.35-1.24 (m, 3H), 1.12 (s, 9H), 1.10 (s, 9H), 0.97 (d, J=6.8 Hz, 3H), 0.94 (d, J=6.8 Hz, 3H), 0.87 (s, 9H), 0.07--0.02 (m, 6H).

(b) Allyl 3-(2-(2-(4-(((((2-((S)-2-(hydroxymethyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate (67)

The TBS ether 66 (1.32 g, 1.38 mmol) was dissolved in a 7:1:1:2 mixture of acetic acid/methanol/tetrahydrofuran/water (14:2:2:4 mL) and allowed to stir at room temperature. After 3 hours no more starting material was observed by LC/MS. The reaction mixture was diluted with ethyl acetate (25 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol in dichloromethane). Pure fractions were collected and combined and excess eluent was removed by rotary evaporation under reduced pressure to afford the desired product 67 (920 mg, 80%). LC/MS, 3.60 min (ES+) m/z (relative intensity) 838.18 ([M+H]$^{+\cdot}$, 100). $^1$H NMR (400 MHz, CDCl$_3$) δ 8.55 (s, 1H), 8.35 (s, 1H), 7.68 (s, 1H), 7.52 (d, J=8.1 Hz, 2H), 7.31 (d, J=8.4 Hz, 2H), 6.77 (s, 1H), 6.71 (d, J=7.5 Hz, 1H), 6.13 (s, 1H), 5.97-5.82 (m, J=5.7 Hz, 1H), 5.41-5.15 (m, 3H), 5.10 (d, J=3.5 Hz, 2H), 4.76-4.42 (m, 5H), 4.03 (t, J=6.6 Hz, 1H), 3.77 (s, 5H), 2.84 (dd, J=16.7, 10.4 Hz, 1H), 2.26-2.08 (m, 2H), 1.68 (s, 3H), 1.44 (d, J=7.0 Hz, 3H), 1.30 (dt, J=14.7, 7.4 Hz, 3H), 1.12 (s, 9H), 1.10 (s, 9H), 0.96 (d, J=6.8 Hz, 3H), 0.93 (d, J=6.8 Hz, 3H).

(c) (11S,11aS)-4-(2-(1-((1-(allyloxy)-4-methyl-1,2-dioxopentan-3-yl)amino)-1-oxopropan-2-yl)hydrazinyl)benzyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (68)

Dimethyl sulphoxide (0.2 mL, 2.75 mmol, 2.5 eq) was added dropwise to a solution of oxalyl chloride (0.11 mL, 1.32 mmol, 1.2 eq) in dry dichloromethane (7 mL) at −78° C. (dry ice/acetone bath) under an atmosphere of argon. After 10 minutes a solution of 67 (920 mg, 1.10 mmol) in dry dichloromethane (5 mL) was added slowly with the temperature still at −78° C. After 15 min triethylamine (0.77 mL, dried over 4 Å molecular sieves, 5.50 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 2% methanol to 5% methanol in dichloromethane). Pure fractions were collected and combined and removal of excess eluent by rotary evaporation under reduced pressure afforded the product 68 (550 mg, 60%). LC/MS, 3.43 min (ES+) m/z (relative intensity) 836.01 ([M]$^{+\cdot}$, 100). $^1$H NMR (400 MHz, CDCl$_3$) δ 8.39 (s, 1H), 7.52-7.40 (m, 2H), 7.21-7.08 (m, J=11.5 Hz, 2H), 6.67 (s, 1H), 6.60-6.47 (m, J=7.4 Hz, 1H), 5.97-5.83 (m, 1H), 5.79-5.66 (m, 1H), 5.38-4.90 (m, 6H), 4.68-4.52 (m, J =18.4, 5.5 Hz, 4H), 4.04-3.94 (m, J=6.5 Hz, 1H), 3.87-3.76 (m, 5H), 3.00-2.88 (m, 1H), 2.66-2.49 (m, 2H), 2.21-2.08 (m, 2H), 1.76 (s, 3H), 1.45 (d, J=7.0 Hz, 3H), 1.09-0.98 (m, J=8.9 Hz, 18H), 0.96 (d, J=6.7 Hz, 3H), 0.93 (d, J=6.9 Hz, 3H).

(d) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (69)

Tert-butyldimethylsilyltriflate (0.38 mL, 1.62 mmol, 3 eq) was added to a solution of compound 68 (450 mg, 0.54 mmol) and 2,6-lutidine (0.25 mL, 2.16 mmol, 4 eq) in dry dichloromethane (5 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 69 (334 mg, 65%). LC/MS, 4.18 min (ES+) m/z (relative intensity) 950.50 ([M]+·, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(e) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (70)

Lithium acetate (50 mg, 0.49 mmol) was added to a solution of compound 69 (470 mg, 0.49 mmol) in wet dimethylformamide (4 mL, 50:1 DMF/water). After 4 hours, the reaction was complete and the reaction mixture was diluted with ethyl acetate and washed with citric acid (pH ~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 25/75 v/v hexane/ethyl acetate). Pure fractions were collected and combined and excess eluent was removed by rotary evaporation under reduced pressure to give the product 70 (400 mg, quantitative). LC/MS, 3.32 min (ES+) m/z (relative intensity) 794.18 ([M+H]+·, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J =34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(iv) (11S)-4-(2-(1-((1-amino-3-methyl-1-oxobutan-2-yl)amino)-1-oxopropan-2-yl)hydrazinyl)benzyl 11-hydroxy-7-methoxy-8-((5-((7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (73)

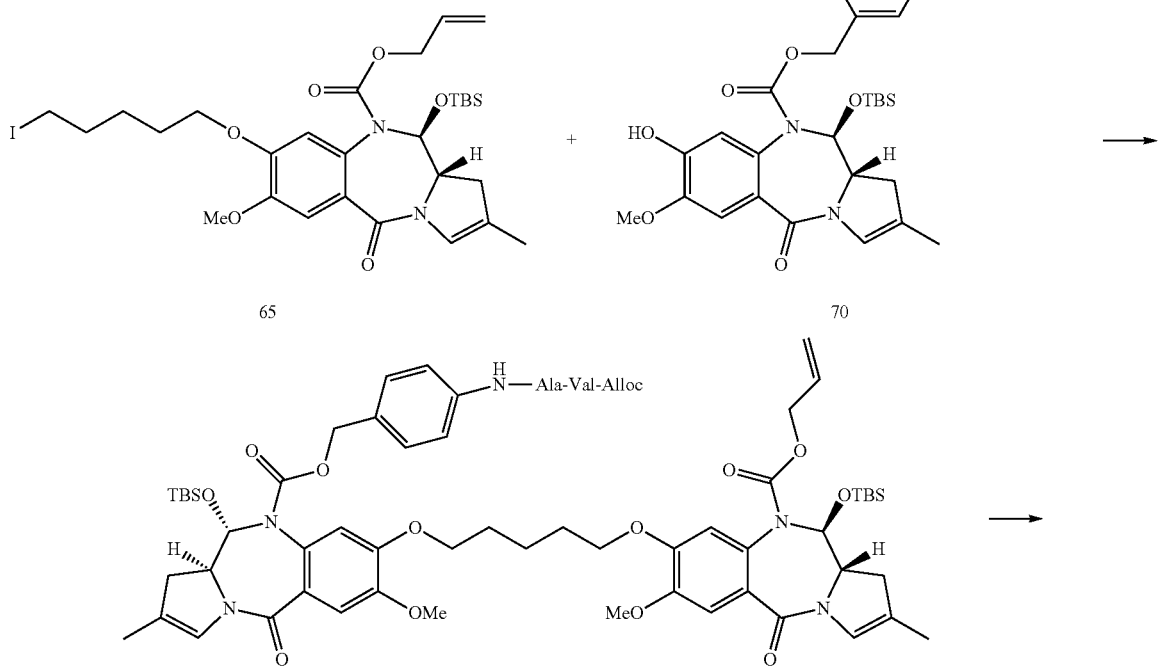

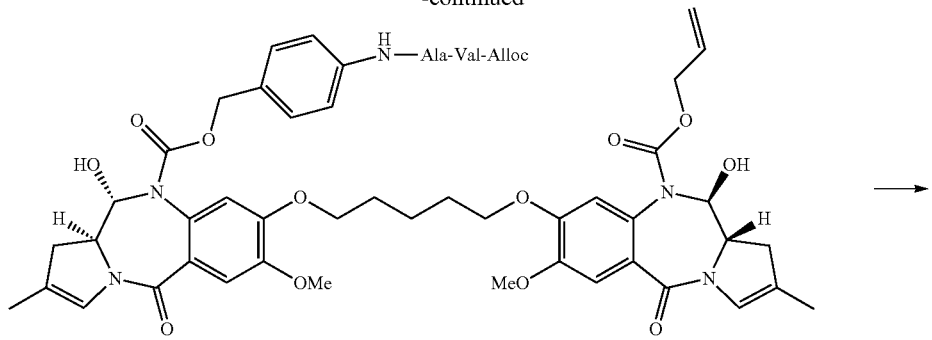

72

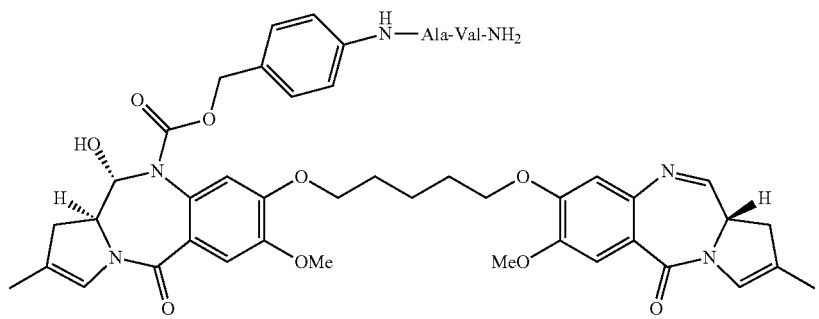

73

(a) (11S)-allyl 8-((5-(((11S)-10-(((4-(2-(1-((1-(allyloxy)-4-methyl-1,2-dioxopentan-3-yl)amino)-1-oxopropan-2-yl)hydrazinyl)benzyl)oxy)carbonyl)-11-((tert-butydimethylsilyl)oxy)-7-methoxy-2-methyl-5-oxo-5,10,11,11a-tetrahydrodro-1H-benzo[e]pyrrolo[1,2-a][1,4]diazepin-8-yl)oxy)pentyl)oxy)-11-((tert-butyldimethysilyl)oxy)-7-methoxy-2-methyl-5-oxo-11,11a -dihydro-1H-benzo[e]pyrrolo[1,2-a][1,4]diazepine-10(5H)-carboxylate (71)

Potassium carbonate (70 mg, 0.504 mmol, 1 eq) was added to a solution of 65 (370 mg, 0.552 mmol, 1.2 eq) and phenol 70 (400 mg, 0.504 mmol) in dry acetone (25 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 71 (385 mg, 57%). LC/MS, 4.07 min (ES+) m/z (relative intensity) 1336.55 ([M+H]$^{+\cdot}$, 50).

(b) (11S)-allyl 8-((5-(((11S)-10-(((4-(2-(1-((1-(allyloxy)-4-methy-1,2-dioxopentan-3-yl)amino)-1-oxopropan-2-yl)hydrazinyl)benzyl)oxy)carbonyl)-11-hydroxy-7-methoxy-2-methy-5-oxo-5,10,11,11a-tetrahydro-1H-benzo[e]pyrrolo[1,2-a][1,4]diazepin-8-yl)oxy)pentyl)oxy)-11-hydroxy-7-methoxy-2-methyl-5-oxo-11,11a-dihydro-1H-benzo[e]pyrrolo[1,2-a][1,4]diazepine-10(5H)-carboxylate (72)

Tetra-n-butylammonium fluoride (1M, 0.34 mL, 0.34 mmol, 2 eq) was added to a solution of 71 (230 mg, 0.172 mmol) in dry tetrahydrofuran (3 mL). The starting material was totally consumed after 10 minutes. The reaction mixture was diluted with ethyl acetate (30 mL) and washed sequentially with water and brine. The organic phase was dried over magnesium sulphate filtered and excess ethyl acetate removed by rotary evaporation under reduced pressure. The resulting residue 72 was used as a crude mixture for the next reaction. LC/MS, 2.87 min (ES+) m/z (relative intensity) 1108.11 ([M+H]$^{+\cdot}$, 100).

(c) (11S)-4-(2-(1-((1-amino-3-methyl-1-oxobutan-2-yl)amino)-1-oxopropan-2-yl)hydrazinyl)benzyl 11-hydroxy-7-methoxy-8-((5-((7-methoxy-2-methyl-5-oxo-5,11a-dihydro-1H-benzo[e]pyrrolo[1,2-a][1,4]diazepin-8-yl)oxy)pentyl) oxy)-2-methyl-5-oxo-11,11a-dihydro-1H-benzo[e]pyrrolo[1,2-a][1,4]diazepine-10 (5H)-carboxylate (73)

Tetrakis(triphenylphosphine)palladium(0) (12 mg, 0.01 mmol, 0.06 eq) was added to a solution of crude 72 (0.172 mmol) and pyrrolidine (36 µL, 0.43 mmol, 2.5 eq) in dry dichloromethane (10 mL). The reaction mixture was stirred 20 minutes and diluted with dichloromethane and washed sequentially with saturated aqueous ammonium chloride and brine. The organic phase was dried over magnesium sulphate filtered and excess dichloromethane removed by rotary evaporation under reduced pressure. The resulting residue 73 was used as a crude mixture for the next reaction. LC/MS, 2.38 min (ES+) m/z (relative intensity) 922.16 ([M+H]$^{+\cdot}$, 40).

(v) Key Intermediates (a) 1-iodo-2-oxo-6,9,12,15-octaoxa-3-azatriacontan-30-oic acid (75)

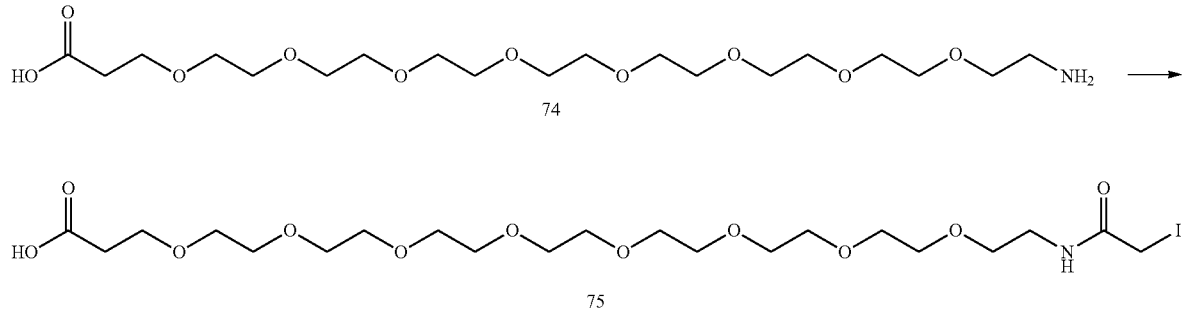

A solution of iodoacetic anhydride (0.088 g, 0.249 mmol, 1.1 eq) in dry DCM (1 mL) was added to amino-PEG$_{(8)}$-acid 74 (0.100 g, 0.226 mmol, 1.0 eq) in DCM (1 mL). The mixture was stirred in the dark at room temperature for 4 hours. The reaction mixture was washed with 5% citric acid, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as a clear oil (0.068 g, 49%). LC/MS (1.13 min (ES$^+$)) (System 1), m/z: 610.15 [M+H]$^+$. $^1$H NMR (400 MHz, CDCl$_3$) δ 7.04 (brs, 1H), 3.78 (t, J=6.0 Hz, 2H,), 3.74 (s, 2H), 3.68-3.64 (m, 28H), 3.60-3.56 (m, 2H), 3.46 (dd, J=10.2 Hz, 5.3 Hz, 2H), 2.61 (t, J=6.0 Hz, 2H).

(b) 1-bromo-2-oxo-6,9,12,15-octaoxa-3-azatriacontan-30-oic acid (76)

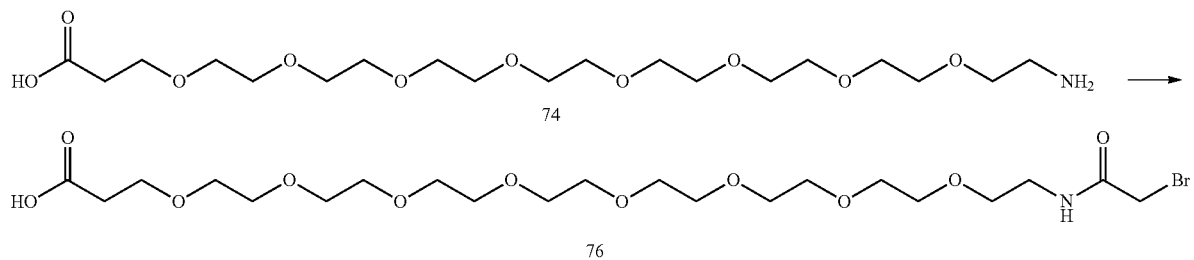

A solution of bromoacetic anhydride (0.065 g, 0.249 mmol, 1.1 eq) in dry DCM (1 mL) was added to amino-PEG$_{(8)}$-acid 74 (0.100 g, 0.226 mmol, 1.0 eq) in DCM (1 mL). The mixture was stirred in the dark at room temperature for 4 hours. The reaction mixture was washed with 5% citric acid, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as a pale orange oil (0.050 g, 39%). LC/MS (1.08 min (ES$^+$)) (System 1), m/z: 562.20 [M]$^+$ 564.15 [M+2]$^+$. $^1$H NMR (400 MHz, CDCl$_3$) δ 7.28 (brs, 1H), 3.87 (s, 2H), 3.76 (t, J=6.1 Hz, 2H), 3.68-3.60 (m, 28H), 3.60-3.56 (m, 2H), 3.47 (dd, J=10.3 Hz, 5.2 Hz, 2H), 2.59 (t, J=6.1 Hz, 2H).

General Experimental Methods for Steps (vi) and (vii)

LC/MS data were obtained using a Shimadzu Nexera series LC/MS with a Shimadzu LC/MS-2020 quadrupole MS, with Electrospray ionisation. Mobile phase A—0.1% formic acid in water. Mobile phase B—0.1% formic acid in acetonitrile. Flow rate of 0.80 ml/min. Gradient from 5% B rising up to 100% B over 2.00 min, remaining at 100% B for 0.50 min and then back down to 5% B over 0.05 min (held for 0.45 min). The total run time is 3 min. Column: Waters, Aquity UPLC BEH Shield RP18 1.7 μm, 2.1×50 mm; (System 1).

Or, gradient from 5% B rising up to 100% B over 10.00 min, remaining at 100% B for 2.00 min and then back down to 5% B over 0.10 minutes (held for 2.90 min). The total run time is 15 minutes. Column: Phenomenex, Gemini-NX 3u C18 110A, 100×2.00 mm; (System 2). Chromatograms based on UV detection at 254 nm. Mass Spectra were achieved using the MS in positive mode.

HPLC analyses were carried out on HPLC system: Shimadzu Prominence series with UV/VIS detector (SPD-20A) and fraction collector (FRC-10A). Mobile phase A—0.1% formic acid in water. Mobile phase B—0.1% formic acid in acetonitrile. Gradient (applicable to analytical and preparative systems) from 0% B rising up to 100% B over 15.00 min, remaining at 100% B for 2.00 min and then down to 13% B over 1.10 min. Analytical analysis, column: Phenomenex, Gemini-NX 5μ C18 110A, 150×4.60 mm and flow rate of 1.00 ml/min (System 3). Preparative analysis, column: Phenomenex, Gemini-NX 5μ C18 110A, 150×21.20 mm and flow rate of 20.00 ml/min. (System 4)

(vi) (11S,11aS)-4-((32S,35S)-1-iodo-32-isopropyl-35-methyl-2,30,33-trioxo-6,9,12,15-octaoxa-3,31,34-triazahexatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (77, D)

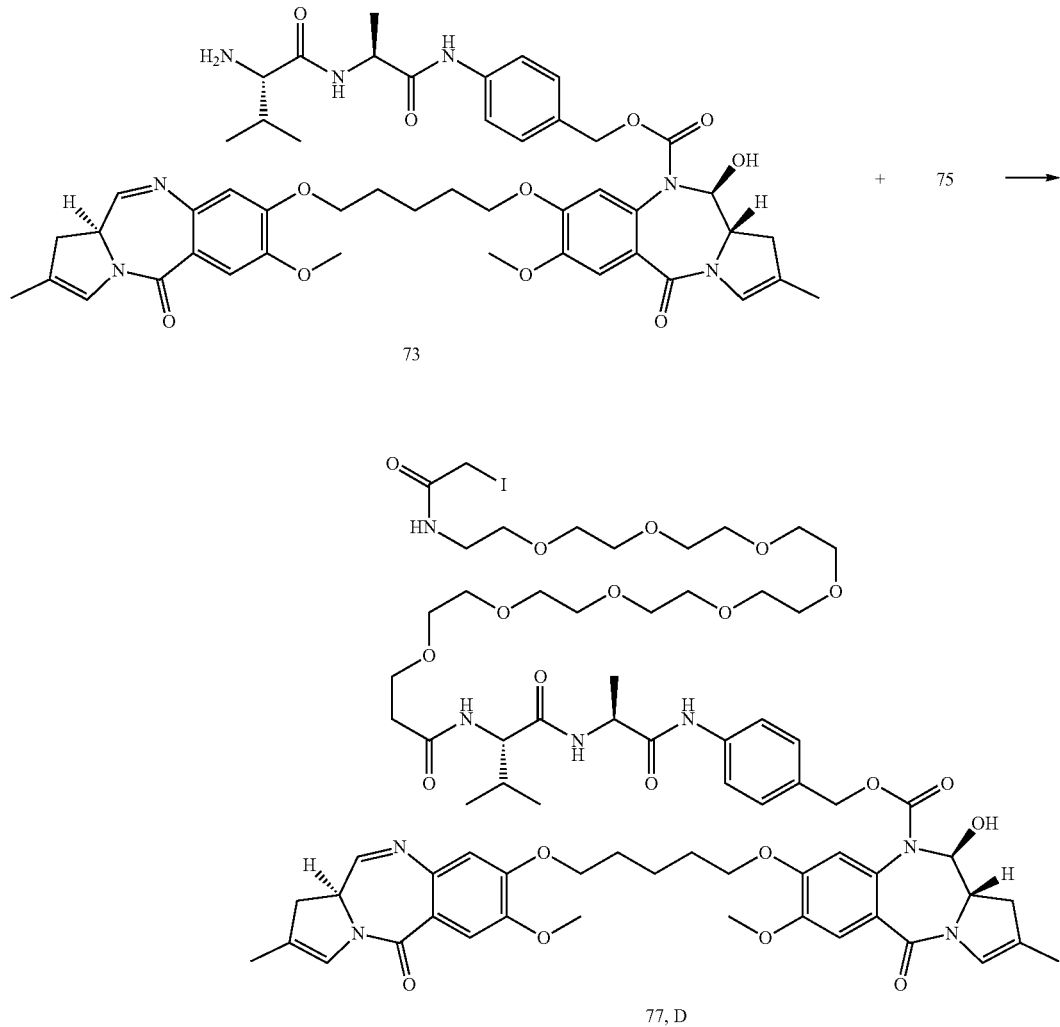

N,N'-diisopropylcarbodiimide (DIC, 9.22 µL, 0.059 mmol, 1.1 eq) was added to a solution of amine 73 (0.054 mmol, 1.1 eq) and iodo-(PEG)$_8$-acid 75 (39.6 mg, 0.065 mmol, 1.2 eq) in dry dichloromethane (5 mL). The reaction was stirred overnight until the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was subjected to flash column chromatography (silica gel; 100% chloroform to 5% methanol in chloroform). Fractions containing the product were collected and combined and excess eluent was removed by rotary evaporation under reduced pressure, this was subjected to further purification using reverse-phase preparative HPLC (System 4). Pure fractions were collected using the fraction collector, combined and the desired product lyophilised to give 77, D (15.8 mg, 19% over 3 steps). LC-MS, System 1, 1.44 min (ES+) m/z 1513.60 [M+H]$^+$. $^1$H NMR (400 MHz, CDCl$_3$) δ 8.82 (s, 1H), 7.92-7.78 (m, 1H), 7.64 (d, J=7.0 Hz, 2H), 7.50 (s, 1H), 7.23-6.98 (m, 6H), 6.81 (s, 1H), 6.75 (s, 1H), 6.69 (s, 1H), 6.46 (s, 1H), 5.76 (d, J=8.3 Hz, 1H), 5.32 (m, 1H), 4.73 (d, J=11.3 Hz, 1H), 4.67-4.54 (m, 1H), 4.42 (br s, 1H), 4.32-4.19 (m, 2H), 4.18-3.99 (m, 4H), 3.91 (s, 3H), 3.87 (s, 3H), 3.84-3.76 (m, 3H), 3.71 (s, 2H), 3.70-3.58 (m, 28H), 3.56 (dd, J=10.1, 5.1 Hz, 2H), 3.43 (dd, J=10.0, 5.1 Hz, 1H), 3.25-3.12 (m, 1H), 3.06-2.87 (m, 2H), 2.73-2.41 (m, 4H), 2.33-1.97 (m, 3H), 1.96-1.71 (m, 4H), 1.84 (s, 3H), 1.78 (s, 3H), 1.71-1.51 (m, 2H), 1.49-1.22 (m, 3H), 1.07-0.85 (m, 6H).

(vii) (11S,11aS)-4-((32S,35S)-1-bromo-32-isopropyl-35-methyl-2,30,33-trioxo-6,9,12,15-octaoxa-3,31,34-triazahexatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (78, E)

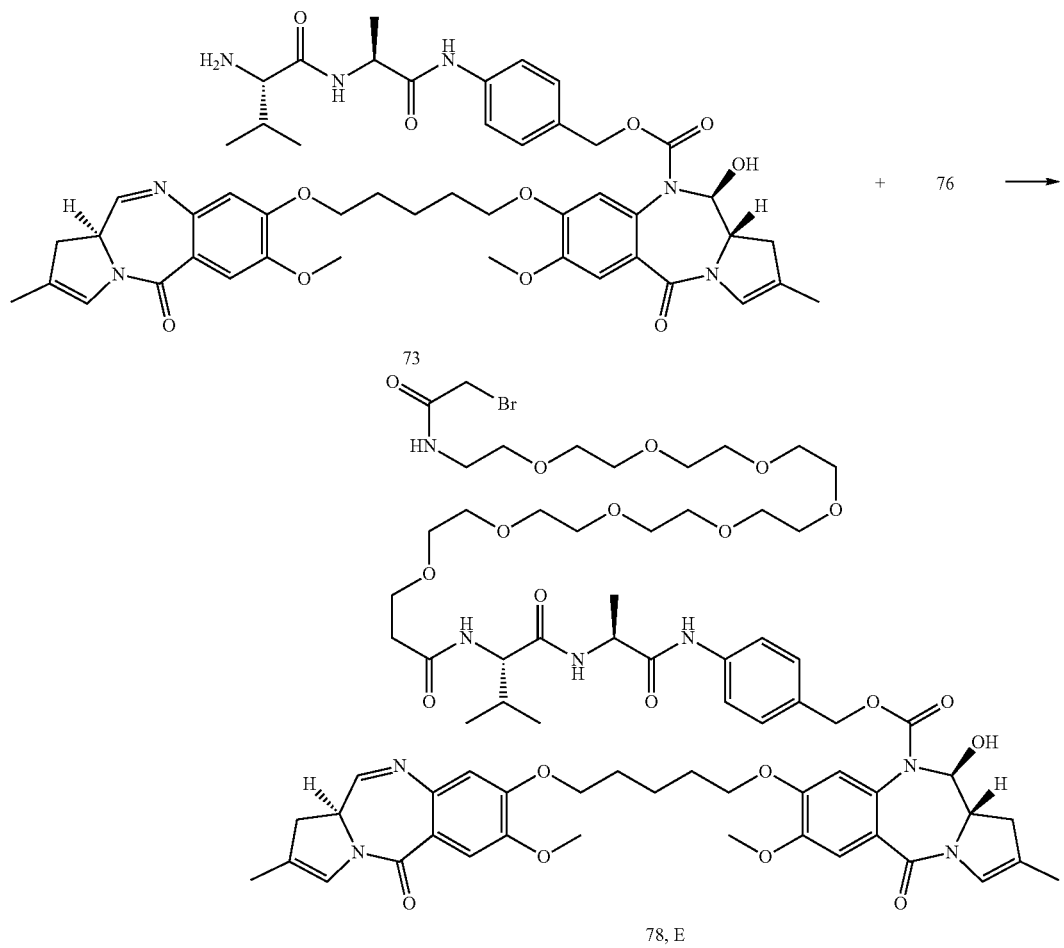

N,N'-diisopropylcarbodiimide (DIC, 9.22 µL, 0.059 mmol, 1.1 eq) was added to a solution of amine 73 (0.054 mmol, 1.1 eq) and bromo-(PEG)$_8$-acid 76 (36.5 mg, 0.065 mmol, 1.2 eq) in dry dichloromethane (5 mL). The reaction was stirred overnight until the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was purified using reversed-phase preparative HPLC (System 4). Pure fractions were collected using the fraction collector, combined and the desired product lyophilised to give 78, E (26.6 mg, 33% over 3 steps). LC-MS, System 1, 1.44 min (ES+) m/z 1466.85 [M]$^+$. $^1$H NMR (400 MHz, CDCl$_3$) δ 8.82 (s, 1H), 7.87 (s, 1H), 7.64 (d, J=7.0 Hz, 2H), 7.50 (s, 1H), 7.23-6.98 (m, 6H), 6.81 (s, 1H), 6.74 (s, 1H), 6.69 (s, 1H), 6.45 (s, 1H), 5.75 (d, J=9.2 Hz, 1H), 5.32 (d, J=11.2 Hz, 1H), 4.72 (d, J=11.7 Hz, 1H), 4.68-4.52 (m, 1H), 4.35 (br s, 1H), 4.32-4.17 (m, 2H), 4.17-3.99 (m, 4H), 3.90 (s, 3H), 3.87 (s, 3H), 3.84-3.74 (m, 3H), 3.72-3.58 (m, 32H), 3.46 (dd, J=10.1, 5.1 Hz, 2H), 3.25-3.09 (m, 1H), 3.05-2.84 (m, 2H), 2.75-2.40 (m, 3H), 2.34-1.98 (m, 3H), 1.96-1.71 (m, 4H), 1.83 (s, 3H), 1.77 (s, 3H), 1.67-1.52 (m, 2H), 1.48-1.20 (m, 3H), 1.09-0.88 (m, 6H).

Example 6

Activity of Released Compounds

K562 Assay

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 µL per well. DMSO (200 µL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Compound RelC has an $IC_{50}$ of 0.425 nM in this assay.

Example 7

Formation of Conjugates

General Antibody Conjugation Procedure

Antibodies are diluted to 1-5 mg/mL in a reduction buffer (examples: phosphate buffered saline PBS, histidine buffer, sodium borate buffer,TRIS buffer). A freshly prepared solution of TCEP (tris(2-carboxyethyl)phosphine hydrochloride) is added to selectively reduce cysteine disulfide bridges. The amount of TCEP is proportional to the target level of reduction, within 1 to 4 molar equivalents per antibody, generating 2 to 8 reactive thiols. After reduction for several hours at 37° C., the mixture is cooled down to room temperature and excess drug-linker added as a diluted DMSO solution (final DMSO content of up to 10% volume/volume of reaction mixture). The mixture was gently shaken at either 4° C. or room temperature for the appropriate time, generally 1-3 hours. Excess reactive thiols can be reacted with a 'thiol capping reagent' like N-ethyl maleimide (NEM) at the end of the conjugation. Antibody-drug conjugates are concentrated using centrifugal spin-filters with a molecular weight cut-off of 10 kDa or higher, then purified by tangential flow filtration (TFF) or Fast Protein Liquid Chromatography (FPLC). Corresponding antibody-drug conjugates can be determined by analysis by High-Performance Liquid Chromatography (HPLC) or Ultra-High-Performance Liquid Chromatography (UHPLC) to assess drug-per-antibody ratio (DAR) using reverse-phase chromatography (RP) or Hydrophobic-Interaction Chromatography (HIC), coupled with UV-Visible, Fluorescence or Mass-Spectrometer detection; aggregate level and monomer purity can be analysed by HPLC or UHPLC using size-exclusion chromatography coupled with UV-Visible, Fluorescence or Mass-Spectrometer detection. Final conjugate concentration is determined by a combination of spectroscopic (absorbance at 280, 214 and 330 nm) and biochemical assay (bicinchonic acid assay BCA; Smith, P. K., et al. (1985) *Anal. Biochem.* 150 (1): 76-85; using a known-concentration IgG antibody as reference). Antibody-drug conjugates are generally sterile filtered using 0.2 µm filters under aseptic conditions, and stored at +4° C., −20° C. or −80° C.

DAR Determination

Antibody or ADC (ca. 35 µg in 35 µL) was reduced by addition of 10 µL borate buffer (100 mM, pH 8.4) and 5 µL DTT (0.5 M in water), and heated at 37° C. for 15 minutes. The sample was diluted with 1 volume of acetonitrile: water: formic acid (49%: 49%: 2% v/v), and injected onto a Widepore 3.6µ XB-C18 150×2.1 mm (P/N 00F-4482-AN) column (Phenomenex Aeris) at 80° C., in a UPLC system (Shimadzu Nexera) with a flow rate of 1 ml/min equilibrated in 75% Buffer A (Water, Trifluoroacetic acid (0.1% v/v) (TFA), 25% buffer B (Acetonitrile: water: TFA 90%: 10%: 0.1% v/v). Bound material was eluted using a gradient from 25% to 55% buffer B in 10 min. Peaks of UV absorption at 214 nm were integrated. The following peaks were identified for each ADC or antibody: native antibody light chain (L0), native antibody heavy chain (H0), and each of these chains with added drug-linkers (labelled L1 for light chain with one drug and H1, H2, H3 for heavy chain with 1, 2 or 3 attached drug-linkers). The UV chromatogram at 330 nm was used for identification of fragments containing drug-linkers (i.e., L1, H1, H2, H3).

A PBD/protein molar ratio was calculated for both light chains and heavy chains:

$$\frac{Drug}{Protein}\text{ratio on light chain} = \frac{\%\text{ Area at 214 nm for } L1}{\%\text{ Area at 214 nm for } L0 \text{ and } L1}$$

$$\frac{Drug}{Protein}\text{ratio on heavy chain} = \frac{\sum_{n=0}^{3} n \times (\%\text{ area at 214 for Hn})}{\sum_{n=0}^{3} \%\text{ area at 214 for Hn}}$$

Final DAR is calculated as:

$$DAR = 2 \times \left(\frac{Drug}{Protein}\text{ratio on light chain} + \frac{Drug}{Protein}\text{ratio on heavy chain}\right)$$

DAR measurement is carried out at 214 nm because it minimises interference from drug-linker absorbance.

Generation of ADC (J591-E)

To J591, comprising a variable domain which is SEQ ID NO. 3 paired with SEQ ID NO. 4, (33.3 mg, 222 nanomoles) in 4.83 mL PBS, EDTA was added to a final concentration of 2.0 mM EDTA. The antibody was reduced for 4 hours at room temperature by a solution of TCEP (40 eq, 889 L at 10 mM, 8890 nanomoles), then dialysed overnight against PBS, 2.5 mM EDTA. Ca. 8 mL of antibody at 2.9 mg/mL was recovered (23 mg, 70%) then the antibody was reoxidised by adding 20 eq dhaa (dehydroascorbic acid, fresh 50 mM solution in DMA, 89 µL, 4 micromoles). Reoxidation was carried out at room temperature for 3 hours, the antibody batch was dialysed overnight into 10 mM sodium borate pH 8.4 containing 2.5 mM EDTA. Antibody is sterile filtered, then split in four aliquot. To one aliquot (1 mL at 3.0 mg/mL=3.0 mg, 20.0 nanomoles) was diluted to 3 mL of 10 mM sodium borate, 2 mM EDTA pH 8.4; compound E was added as a DMSO solution (20 molar equivalent/antibody, 400 nanomoles, in 0.3 mL DMSO) in two fractions overnight. The solution was kept at room temperature, then the conjugation was quenched by addition of N-acetyl cysteine (0.8 micromoles, 80 µL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to J591-E monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C 18 150×2.1 mm column eluting with a gradient of water and acetonitrile on a reduced sample of J591-E at 280 nm and 330 nm (Compound E specific) shows a mixture of light and heavy chains attached to several molecules of compound E, consistent with a drug-per-antibody ratio (DAR) of 1.0 molecules of compound E per antibody.

UHPLC analysis on a Shimadzu Prominence system using a Tosoh TSKgel G3000 SWCL 5 um 7.8×300 mm 300×4.60 mm eluting with sterile-filtered SEC buffer containing 200 mM potassium phosphate pH 6.95, 250 mM potassium chloride and 10% isopropanol (v/v) on a sample of J591-E at 280 nm shows a monomer purity of over 91.6%. UV/Vis concentration assay gives a final amount of J591-E of 1.0 mg (33% yield).

Generation of ADC (J591-C)

To J591 (15.3 mg, 102 nanomoles) in PBS, EDTA and DTT solutions were added to a final concentration of 1.5 mM EDTA and 3 mM DTT. The antibody was reduced overnight (ca. 16 h) at room temperature, then diluted with 45 mL 20 mM sodium succinate pH 5.0, loaded on a GE Healthcare HiTrap SP FF Column 1 mL using an Akta system. Antibody was eluted out using 50 mM Tris-HCl pH 7.5, 150 mM NaCl and the elute was buffer exchanged by dialysis with 100 mM NaPO4, 2.5 mM EDTA. The antibody was then reoxidised by adding 20 eq dhaa (dehydroascorbic acid, fresh 20 mM solution in DMA, 100 µL, 2 micromoles). Reoxidation was carried out at room temperature for 3 hours and compound C was added as a DMSO solution (10.0 molar equivalent/antibody, 10000 nanomoles, in 0.9 mL DMSO). The solution was mixed for 1.5 hours at room temperature, then the conjugation was quenched by addition of N-acetyl cysteine (4 micromoles, 400 µL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to J591-C monomer peak were pooled, concentrated using a 15 mL Amicon Ultracell 50 KDa MWCO spin filter, analysed and sterile-filtered. The batch was then mixed with a previously made batch of the same ADC from 5 mg antibody. UHPLC analysis on a Shimadzu Prominence system using a Phenomenex Aeris 3.6u XB-C18 150×2.1 mm column eluting with a gradient of water and acetonitrile on a reduced sample of J591-C at 280 nm and 330 nm (Compound C specific) shows a mixture of light and heavy chains attached to several molecules of compound C, consistent with a drug-per-antibody ratio (DAR) of 1.88 molecules of compound C per antibody.

UHPLC analysis on a Shimadzu Prominence system using a Tosoh TSKgel G3000 SWCL 5 um 7.8×300 mm 300×4.60 mm eluting with sterile-filtered SEC buffer containing 200 mM potassium phosphate pH 6.95, 250 mM potassium chloride and 10% isopropanol (v/v) on a sample of J591-C at 214 nm shows a monomer purity of over 98.1% with 1.8% dimer. HPLC concentration assay gives a concentration of final J591-C at 0.74 mg/mL in 12.0 mL, obtained mass of J591-C is 8.85 mg (44% combined yield from 15 mg and 5 mg antibody).

In Vitro Cytotoxicity

The efficacy of the J591-C and J-591E conjugates was tested against LNCaP cells as described above:

|         | $GI_{50}$ (ng/mL) |
|---------|-------------------|
| J591-C  | 13.7              |
| J591-E  | 25.4              |

Example 8

In Vivo ADC Efficacy Studies

Male severe combined immunodeficient mice (Fox Chase SCID®, C.B-17/Icr-Prkdcscid, Charles River) were nine weeks old with a body weight (BW) range of 18.9 to 26.7 grams on Day 1 of the study.

The 22Rv1 cells used for implantation were harvested during exponential growth and resuspended in 50% Matrigel (BD Biosciences) in phosphate buffered saline. On the day of tumor implant, each test mouse was injected subcutaneously in the right flank with $1 \times 10^7$ cells (0.2 mL cell suspension), and tumor growth was monitored as the average size approached the target range of 100 to 150 mm³. Tumors were measured in two dimensions using calipers, and volume was calculated using the formula:

$$\text{Tumor Volume (mm}^3\text{)} = w^2 \times l/2$$

where w=width and l=length, in mm, of the tumor. Tumor weight may be estimated with the assumption that 1 mg is equivalent to 1 mm³ of tumor volume.

Ten days after tumor implantation, designated as Day 1 of the study, the animals were sorted into groups each consisting of ten mice with individual tumor volumes ranging from 108 to 144 mm³ and group mean tumor volumes of 128 mm³.

All agents were administered intravenously (i.v.) via tail vein injection once per week for three weeks (qwk×3) or once on Day 1 (qd×1) in a dosing volume of 0.2 mL per 20 grams of body weight (10 mL/kg), scaled to the body weight of each individual animal. Tumors were measured using calipers twice per week, and each animal was euthanized when its tumor reached the endpoint volume of 1000 mm³ or at the end of the study (Day 114), whichever came first.

FIG. 1 shows the effect on mean tumour volume in groups of 10 miced dosed with J591-C at 0.3 (◇—lower line) and 1.0 mg/kg (□) or J591-E at 0.3 (Δ) and 1.0 mg/kg (◇—higher line) compared to vehicle (○) control.

ABBREVIATIONS

Ac acetyl
Acm acetamidomethyl
Alloc allyloxycarbonyl
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy) propanoate-Val-Ala-PAB
MC-OSu maleimidocaproyl-O—N-succinimide
Moc methoxycarbonyl
MP maleimidopropanamide Mtr 4-methoxy-2,3,6-trimethtylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichlorethoxycarbonyl chloride
Trt trityl
Xan xanthyl

SEQUENCES

SEQ ID NO. 1 (J591 VH):
EVQLQQSGPELKKPGTSVRISCKTSGYTFTEYTIHWVKQSHGKSLE
WIGNINPNNGGTTYNQKFEDKATLTVDKSSTAYMELRSLTSEDSA
VYYCAAGWNFDYWGQGTTLTVSS

SEQ ID NO. 2 (J591 VL):
DIVMTQSHKFMSTSVGDRVSIICKASQDVGTAVDWYQQKPGQSPKL
LIYWASTRHTGVPDRFTGSGSGTDFTLTITNVQSEDLADYFCQQYN
SYPLTFGAGTMLDLK

SEQ ID NO. 3 (J591 VH Delm):
EVQLVQSGPEVKKPGATVKISCKTSGYTFTEYTIHWVKQAPGKGLE
WIGNINPNNGGTTYNQKFEDKATLTVDKSTDTAYMELSSLRSEDTA
VYYCAAGWNFDYWGQGTLLTVSS SEQ ID NO. 4 (J591 VK Delm):
DIQMTQSPSSLSTSVGDRVTLTCKASQDVGTAVDWYQQKPGPSPKL
LIYWASTRHTGIPSRFSGSGSGTDFTLTISSLQPEDFADYYCQQYN
SYPLTFGPGTKVDIK SEQ ID NO. 5 (J415 VH):
EVKLEESGGGLVQPGGSMKLSCVASGFTFSNYWMNWVRQSPEKGLE
WVAEIRSQSNNFATHYAESVKGRVIISRDDSKSSVYLQMNNLRAED
TGIYYCTRRWNNFWGQGTTLTVSS SEQ ID NO. 6 (J415 VL):
NIVMTQFPKSMSISVGERVTLTCKASENVGTYVSWYQQKPEQSPKM
LIYGASNRFTGVPDRFTGSGSATDFILTISSVQTEDLVDYYCGQSY
TFPYTFGGGTKLEMK SEQ ID NO. 7 (J415-2 VH Delm):
EVKLEESGGGLVQPGGSMKISCVASGFTFSNYWMNWVRQTPEKGLE
WVALIRSQSNNFATHYAESVKGRVIISRDDSKSSVYLQMNSLRAED
TAVYYCTRRWNNFWGQGTTVTVSS SEQ ID NO. 8 (J415-3 VH Delm):
EVKLEESGGGLVQPGGSMKISCVASGFTFSNYWMNWVRQTPEKGLE
WVAEIRSQSNNFATHYAESVKGRVIISRDDSKSSVYLQMNSLRAED
TAVYYCTRRWNNFWGQGTTVTVSS SEQ ID NO. 9 (J415 VH Delm consensus):
EVKLEESGGGLVQPGGSMKISCVASGFTFSNYWMNWVRQTPEKGLE
WVAEIRSQSNNFATHYAESVKGRVIISRDDSKSSVYLQMNSLRAED
TAVYYCTRRWNNFWGQGTTVTVSS SEQ ID NO. 10 (J415 VH-MuVH consensus):
EVKLEESGGGLVQPGGSMKLSCVASGFTFSNYWMNWVRQSPEKGLE
WVAEIRLQSDNFATHYAESVKGRVIISRDDSKSSVYLQMNNLRAED
TGIYYCTTGGYGGRRSWNAFWGQGTLVTVSS SEQ ID NO. 11 (J415-2 VL Delm):
NIVMTQSPKSMSASAGERMTLTCKASENVGTYVSWYQQKPTQSPKM
LIYGASNRFTGVPDRFSGSGSGTDFILTASSVQAEDPVDYYCGQSY
TFPYTFGGGTKLEMK SEQ ID NO. 12 (J415-3 VL Delm):
NIVMTQSPKSMSASAGERMTLTCKASENVGTYVSWYQQKPTQSPKM
LIYGASNRFTGVPDRFSGSGSGTDFILTASSVQAEDLVDYYCGQSY
TFPYTFGGGTKLEMK SEQ ID NO. 13 (J415-4 VL Delm):
NIVMTQSPKSMSASAGERMTLTCKASENVGTYVSWYQQKPTQSPKM
LIYGASNRFTGVPDRFSGSGSGTDFILTISSVQAEDLVDYYCGQSY
TFPYTFGGGTKLEMK SEQ ID NO. 14 (J415-6 VL Delm):
NIVMTQFPKSMSASAGERMTLTCKASENVGTYVSWYQQKPEQSPKM
LIYGASNRFTGVPDRFSGSGSGTDFILTISSVQAEDLVDYYCGQSY
TFPYTFGGGTKLEMK SEQ ID NO. 15 (J415-7 VL Delm):
NIVMTQFPKSMSASAGERVTLTCKASENVGTYVSWYQQKPTQSPKM
LIYGASNRFTGVPDRFSGSGSGTDFILTISSVQAEDLVDYYCGQSY
TFPYTFGGGTKLEMK SEQ ID NO. 16 (J415-8 VL Delm):
NIVMTQFPKSMSASAGERMTLTCKASENSGTYVSWYQQKPEQSPKM
LIYGASNRFTGVPDRFSGSGSGTDFILTISSVQAEDLVDYYCGQSY
TFPYTFGGGTKLEMK SEQ ID NO. 17 (J415 VL consensus):
NIVMTQFPKSMSASAGERMTLTCKASENVGTYVSWYQQKPEQSPKM
LIYGASNRFTGVPDRFSGSGSGTDFILTISSVQAEDLVDYYCGQSY
TFPYTFGGGTKLEMK SEQ ID NO. 18 (J415 VL-MuVL1 consensus):
DIVMTQSPSSLAVSAGEKVTLSCKASESLLNVGNQKTYVAWYQQKP
GQSPKLLIYGASTRESGVPDRFTGSGSGTDFILTISSVQAEDLAVY
YCGNSYSFPLTFGGGTKLELK SEQ ID NO. 19 (J591 Delm heavy chain):
EVQLVQSGPEVKKPGATVKISCKTSGYTFTEYTIHWVKQAPGKGLE
WIGNINPNNGGTTYNQKFEDKATLTVDKSTDTAYMELSSLRSEDTA
VYYCAAGWNFDYWGQGTLLTVSSASTKGPSVFPLAPSSKSTSGGTA
ALGCLVKDYFPEPVTVSWNSGALTSGVHTFPAVLQSSGLYSLSSVV
TVPSSSLGTQTYICNVNHKPSNTKVDKKVEPKSCDKTHTCPPCPAP

| SEQUENCES |
|---|
| ELLGGPSVFLFPPKPKDTLMISRTPEVTCVVVDVSHEDPEVKFNWY |
| VDGVEVHNAKTKPREEQYNSTYRVVSVLTVLHQDWLNGKEYKCKVS |
| NKALPAPIEKTISKAKGQPREPQVYTLPPSRDELTKNQVSLTCLVK |
| GFYPSDIAVEWESNGQPENNYKTTPPVLDSDGSFFLYSKLTVDKSR |
| WQQGNVFSCSVMHEALHNHYTQKSLSLSPGK |

| SEQUENCES |
|---|
| SEQ ID NO. 20 (J591 Delm light chain): |
| DIQMTQSPSSLSTSVGDRVTLTCKASQDVGTAVDWYQQKPGPSPKL |
| LIYWASTRHTGIPSRFSGSGSGTDFTLTISSLQPEDFADYYCQQYN |
| SYPLTFGPGTKVDIKRTVAAPSVFIFPPSDEQLKSGTASVVCLLNN |
| FYPREAKVQWKVDNALQSGNSQESVTEQDSKDSTYSLSSTLTLSKA |
| DYEKHKVYACEVTHQGLSSPVTKSFNRGEC |

The invention claimed is:
1. A conjugate of formula ConjB:

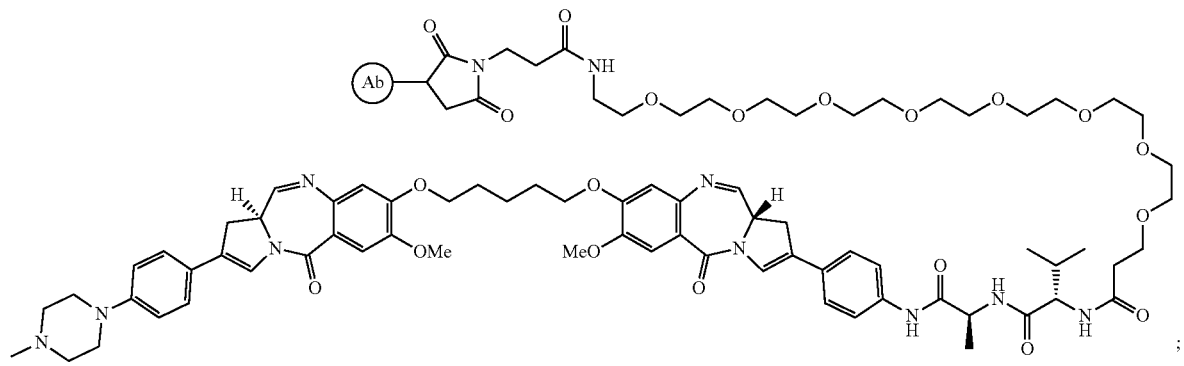

ConjB

;

or ConjC

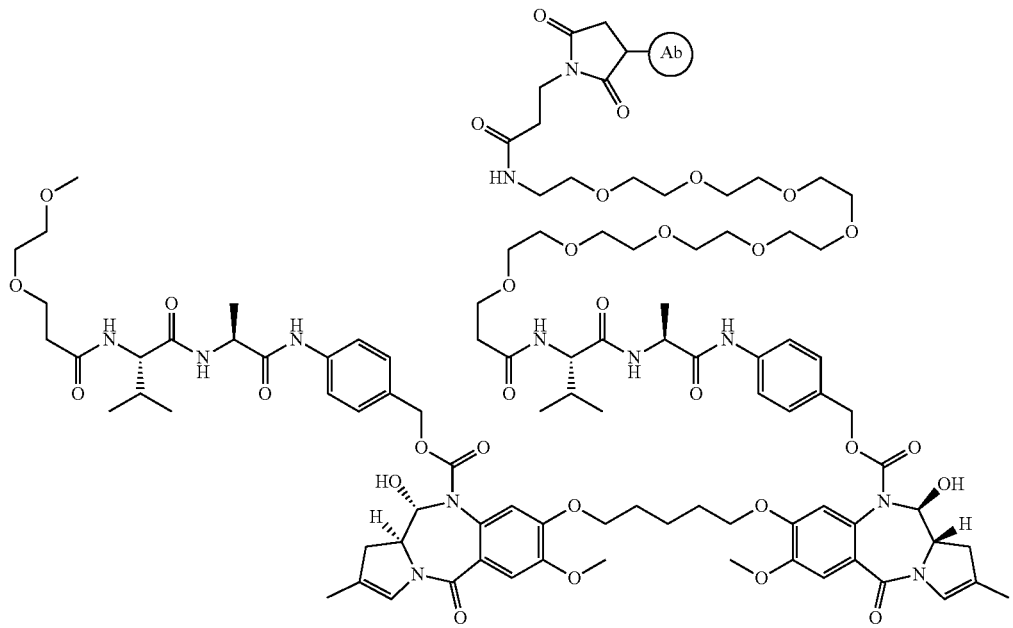

ConjC wherein:
the drug loading is from 1 to 8;
Ab is an antibody that binds to PSMA, the antibody comprising a VH domain having the sequence according to any one of SEQ ID NOs. 1, 3, 5, 7, 8, 9, or 10, optionally further comprising a VL domain having the sequence according to any one of SEQ ID NOs. 2, 4, 6, 11, 12, 13, 14, 15, 16, 17, or 18.

2. The conjugate according to claim 1 wherein the antibody comprises a VH domain paired with a VL domain, the VH and VL domains having sequences selected from the group consisting of:
SEQ ID NO. 1 paired with any one of SEQ ID NOs. 2, 4, 6, 11, 12, 13, 14, 15, 16, 17, or 18;
SEQ ID NO. 3 paired with any one of SEQ ID NOs. 2, 4, 6, 11, 12, 13, 14, 15, 16, 17, or 18;
SEQ ID NO. 5 paired with any one of SEQ ID NOs. 2, 4, 6, 11, 12, 13, 14, 15, 16, 17, or 18;
SEQ ID NO. 7 paired with any one of SEQ ID NOs. 2, 4, 6, 11, 12, 13, 14, 15, 16, 17, or 18;
SEQ ID NO. 8 paired with any one of SEQ ID NOs. 2, 4, 6, 11, 12, 13, 14, 15, 16, 17, or 18;
SEQ ID NO. 9 paired with any one of SEQ ID NOs. 2, 4, 6, 11, 12, 13, 14, 15, 16, 17, or 18; or SEQ ID NO. 10 paired with any one of SEQ ID NOs. 2, 4, 6, 11, 12, 13, 14, 15, 16, 17, or 18.

3. The conjugate according to claim 2 wherein the paired VH and VL domains have the sequences of:
SEQ ID NO. 1 paired with SEQ ID NO. 2, SEQ ID NO. 3 paired with SEQ ID NO. 4, SEQ ID NO. 5 paired with SEQ ID NO. 6, SEQ ID NO. 7 paired with SEQ ID NO. 11, SEQ ID NO. 7 paired with SEQ ID NO. 12, SEQ ID NO. 7 paired with SEQ ID NO. 13, SEQ ID NO. 7 paired with SEQ ID NO. 14, SEQ ID NO. 7 paired with SEQ ID NO. 15, SEQ ID NO. 7 paired with SEQ ID NO. 16, SEQ ID NO. 7 paired with SEQ ID NO. 17, SEQ ID NO. 7 paired with SEQ ID NO. 18, SEQ ID NO. 8 paired with SEQ ID NO. 11, SEQ ID NO. 8 paired with SEQ ID NO. 12, SEQ ID NO. 8 paired with SEQ ID NO. 13, SEQ ID NO. 8 paired with SEQ ID NO. 14, SEQ ID NO. 8 paired with SEQ ID NO. 15, SEQ ID NO. 8 paired with SEQ ID NO. 16, SEQ ID NO. 8 paired with SEQ ID NO. 17, SEQ ID NO. 8 paired with SEQ ID NO. 18, SEQ ID NO. 9 paired with SEQ ID NO. 11, SEQ ID NO. 9 paired with SEQ ID NO. 12, SEQ ID NO. 9 paired with SEQ ID NO. 13, SEQ ID NO. 9 paired with SEQ ID NO. 14, SEQ ID NO. 9 paired with SEQ ID NO. 15, SEQ ID NO. 9 paired with SEQ ID NO. 16, SEQ ID NO. 9 paired with SEQ ID NO. 17, SEQ ID NO. 9 paired with SEQ ID NO. 18, SEQ ID NO. 10 paired with SEQ ID NO. 11, SEQ ID NO. 10 paired with SEQ ID NO. 12, SEQ ID NO. 10 paired with SEQ ID NO. 13, SEQ ID NO. 10 paired with SEQ ID NO. 14, SEQ ID NO. 10 paired with SEQ ID NO. 15, SEQ ID NO. 10 paired with SEQ ID NO. 16, SEQ ID NO. 10 paired with SEQ ID NO. 17, or SEQ ID NO. 10 paired with SEQ ID NO. 18.

4. The conjugate according to claim 1 wherein the antibody in an intact antibody.

5. The conjugate according to claim 1 wherein the antibody is humanised, deimmunised or resurfaced.

6. The conjugate according to claim 1, wherein the drug loading is 1, 2, 3, or 4.

7. A mixture of conjugates according to claim 1, wherein the average value of the drug loading is about 2 to about 5.

8. A pharmaceutical composition comprising a therapeutically effective amount of the conjugate of claim 1 and a pharmaceutically acceptable diluent, carrier or excipient.

9. The pharmaceutical composition of claim 8 further comprising a therapeutically effective amount of a chemotherapeutic agent.

10. A method of treating prostate cancer comprising administering to a patient the pharmaceutical composition of claim 8.

11. The method of claim 10 wherein the patient is administered a therapeutically effective amount of a chemotherapeutic agent, in combination with the conjugate.

* * * * *

SEQUENCE LISTING

<160> NUMBER OF SEQ ID NOS: 23

<210> SEQ ID NO 1
<211> LENGTH: 115
<212> TYPE: PRT
<213> ORGANISM: Artificial sequence
<220> FEATURE:
<223> OTHER INFORMATION: Synthetic sequence: Antibody sequence J591 VH
      of PCT/GB2014/053051

<400> SEQUENCE: 1

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
        115

<210> SEQ ID NO 2
<211> LENGTH: 107
<212> TYPE: PRT
<213> ORGANISM: Artificial sequence
<220> FEATURE:
<223> OTHER INFORMATION: Synthetic sequence: Antibody sequence J591 VL
      of PCT/GB2014/053051

<400> SEQUENCE: 2

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser

```
                65                  70                  75                  80
Glu Asp Leu Ala Asp Tyr Phe Cys Gln Gln Tyr Asn Ser Tyr Pro Leu
                    85                  90                  95

Thr Phe Gly Ala Gly Thr Met Leu Asp Leu Lys
                    100                 105

<210> SEQ ID NO 3
<211> LENGTH: 115
<212> TYPE: PRT
<213> ORGANISM: Artificial sequence
<220> FEATURE:
<223> OTHER INFORMATION: Synthetic sequence: Antibody sequence J591 VH
      DeIm of PCT/GB2014/053051

<400> SEQUENCE: 3

Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
                20                  25                  30

Thr Ile His Trp Val Lys Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
                100                 105                 110

Val Ser Ser
        115

<210> SEQ ID NO 4
<211> LENGTH: 107
<212> TYPE: PRT
<213> ORGANISM: Artificial sequence
<220> FEATURE:
<223> OTHER INFORMATION: Synthetic sequence: Antibody sequence J591 VK
      DeIm of PCT/GB2014/053051

<400> SEQUENCE: 4

Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
                20                  25                  30

Val Asp Trp Tyr Gln Gln Lys Pro Gly Pro Ser Pro Lys Leu Leu Ile
            35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
                100                 105

<210> SEQ ID NO 5
<211> LENGTH: 116
<212> TYPE: PRT
```

<213> ORGANISM: Artificial sequence
<220> FEATURE:
<223> OTHER INFORMATION: Synthetic sequence: Antibody sequence J415 VH of PCT/GB2014/053051

<400> SEQUENCE: 5

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Arg Trp Asn Asn Phe Trp Gly Gln Gly Thr Thr Leu
            100                 105                 110

Thr Val Ser Ser
        115
```

<210> SEQ ID NO 6
<211> LENGTH: 107
<212> TYPE: PRT
<213> ORGANISM: Artificial sequence
<220> FEATURE:
<223> OTHER INFORMATION: Synthetic sequence: Antibody sequence J415 VL of PCT/GB2014/053051

<400> SEQUENCE: 6

```
Asn Ile Val Met Thr Gln Phe Pro Lys Ser Met Ser Ile Ser Val Gly
1               5                   10                  15

Glu Arg Val Thr Leu Thr Cys Lys Ala Ser Glu Asn Val Gly Thr Tyr
            20                  25                  30

Val Ser Trp Tyr Gln Gln Lys Pro Glu Gln Ser Pro Lys Met Leu Ile
        35                  40                  45

Tyr Gly Ala Ser Asn Arg Phe Thr Gly Val Pro Asp Arg Phe Thr Gly
    50                  55                  60

Ser Gly Ser Ala Thr Asp Phe Ile Leu Thr Ile Ser Ser Val Gln Thr
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105
```

<210> SEQ ID NO 7
<211> LENGTH: 116
<212> TYPE: PRT
<213> ORGANISM: Artificial sequence
<220> FEATURE:
<223> OTHER INFORMATION: Synthetic sequence: Antibody sequence J415-2 VH DeIm of PCT/GB2014/053051

<400> SEQUENCE: 7

```
Glu Val Lys Leu Glu Glu Ser Gly Gly Gly Leu Val Gln Pro Gly Gly
1               5                   10                  15

Ser Met Lys Ile Ser Cys Val Ala Ser Gly Phe Thr Phe Ser Asn Tyr
            20                  25                  30
```

```
Trp Met Asn Trp Val Arg Gln Thr Pro Glu Lys Gly Leu Glu Trp Val
        35                  40                  45

Ala Leu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 8
<211> LENGTH: 116
<212> TYPE: PRT
<213> ORGANISM: Artificial sequence
<220> FEATURE:
<223> OTHER INFORMATION: Synthetic sequence: Antibody sequence J415-3 VH
      DeIm of PCT/GB2014/053051

<400> SEQUENCE: 8

Glu Val Lys Leu Glu Glu Ser Gly Gly Gly Leu Val Gln Pro Gly Gly
1               5                   10                  15

Ser Met Lys Ile Ser Cys Val Ala Ser Gly Phe Thr Phe Ser Asn Tyr
            20                  25                  30

Trp Met Asn Trp Val Arg Gln Thr Pro Glu Lys Gly Leu Glu Trp Val
        35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 9
<211> LENGTH: 116
<212> TYPE: PRT
<213> ORGANISM: Artificial sequence
<220> FEATURE:
<223> OTHER INFORMATION: Synthetic sequence: Antibody sequence J415 VH
      DeIm consensus of PCT/GB2014/053051

<400> SEQUENCE: 9

Glu Val Lys Leu Glu Glu Ser Gly Gly Gly Leu Val Gln Pro Gly Gly
1               5                   10                  15

Ser Met Lys Ile Ser Cys Val Ala Ser Gly Phe Thr Phe Ser Asn Tyr
            20                  25                  30

Trp Met Asn Trp Val Arg Gln Thr Pro Glu Lys Gly Leu Glu Trp Val
        35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80
```

```
Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 10
<211> LENGTH: 123
<212> TYPE: PRT
<213> ORGANISM: Artificial sequence
<220> FEATURE:
<223> OTHER INFORMATION: Synthetic sequence: Antibody sequence J415
      VH-MuVH consensus of PCT/GB2014/053051

<400> SEQUENCE: 10

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Gln Ser Asp Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Thr Gly Gly Tyr Gly Gly Arg Arg Ser Trp Asn Ala Phe
            100                 105                 110

Trp Gly Gln Gly Thr Leu Val Thr Val Ser Ser
        115                 120

<210> SEQ ID NO 11
<211> LENGTH: 107
<212> TYPE: PRT
<213> ORGANISM: Artificial sequence
<220> FEATURE:
<223> OTHER INFORMATION: Synthetic sequence: Antibody sequence J415-2 VL
      DeIm of PCT/GB2014/053051

<400> SEQUENCE: 11

Asn Ile Val Met Thr Gln Ser Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ala Ser Ser Val Gln Ala
65                  70                  75                  80

Glu Asp Pro Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 12
```

```
<211> LENGTH: 107
<212> TYPE: PRT
<213> ORGANISM: Artificial sequence
<220> FEATURE:
<223> OTHER INFORMATION: Synthetic sequence: Antibody sequence J415-3 VL
      DeIm of PCT/GB2014/053051

<400> SEQUENCE: 12
```

Asn Ile Val Met Thr Gln Ser Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ala Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

```
<210> SEQ ID NO 13
<211> LENGTH: 107
<212> TYPE: PRT
<213> ORGANISM: Artificial sequence
<220> FEATURE:
<223> OTHER INFORMATION: Synthetic sequence: Antibody sequence J415-4 VL
      DeIm of PCT/GB2014/053051

<400> SEQUENCE: 13
```

Asn Ile Val Met Thr Gln Ser Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

```
<210> SEQ ID NO 14
<211> LENGTH: 107
<212> TYPE: PRT
<213> ORGANISM: Artificial sequence
<220> FEATURE:
<223> OTHER INFORMATION: Synthetic sequence: Antibody sequence J415-6 VL
      DeIm of PCT/GB2014/053051

<400> SEQUENCE: 14
```

Asn Ile Val Met Thr Gln Phe Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

```
Val Ser Trp Tyr Gln Gln Lys Pro Glu Gln Ser Pro Lys Met Leu Ile
        35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 15
<211> LENGTH: 107
<212> TYPE: PRT
<213> ORGANISM: Artificial sequence
<220> FEATURE:
<223> OTHER INFORMATION: Synthetic sequence: Antibody sequence J415-7 VL
      DeIm of PCT/GB2014/053051

<400> SEQUENCE: 15

Asn Ile Val Met Thr Gln Phe Pro Lys Ser Met Ser Ala Ser Ala Gly
 1               5                  10                  15

Glu Arg Val Thr Leu Thr Cys Lys Ala Ser Glu Asn Val Gly Thr Tyr
                 20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 16
<211> LENGTH: 107
<212> TYPE: PRT
<213> ORGANISM: Artificial sequence
<220> FEATURE:
<223> OTHER INFORMATION: Synthetic sequence: Antibody sequence J415-8 VL
      DeIm of PCT/GB2014/053051

<400> SEQUENCE: 16

Asn Ile Val Met Thr Gln Phe Pro Lys Ser Met Ser Ala Ser Ala Gly
 1               5                  10                  15

Glu Arg Met Thr Leu Thr Cys Lys Ala Ser Glu Asn Ser Gly Thr Tyr
                 20                  25                  30

Val Ser Trp Tyr Gln Gln Lys Pro Glu Gln Ser Pro Lys Met Leu Ile
        35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105
```

```
<210> SEQ ID NO 17
<211> LENGTH: 107
<212> TYPE: PRT
<213> ORGANISM: Artificial sequence
<220> FEATURE:
<223> OTHER INFORMATION: Synthetic sequence: Antibody sequence J415 VL
      consensus of PCT/GB2014/053051

<400> SEQUENCE: 17

Asn Ile Val Met Thr Gln Phe Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 18
<211> LENGTH: 113
<212> TYPE: PRT
<213> ORGANISM: Artificial sequence
<220> FEATURE:
<223> OTHER INFORMATION: Synthetic sequence: Antibody sequence J415
      VL-MuVL1 consensus of PCT/GB2014/053051

<400> SEQUENCE: 18

Asp Ile Val Met Thr Gln Ser Pro Ser Ser Leu Ala Val Ser Ala Gly
1               5                   10                  15

Glu Lys Val Thr Leu Ser Cys Lys Ala Ser Glu Ser Leu Leu Asn Val
            20                  25                  30

Gly Asn Gln Lys Thr Tyr Val Ala Trp Tyr Gln Gln Lys Pro Gly Gln
        35                  40                  45

Ser Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Ile Leu Thr
65                  70                  75                  80

Ile Ser Ser Val Gln Ala Glu Asp Leu Ala Val Tyr Tyr Cys Gly Asn
                85                  90                  95

Ser Tyr Ser Phe Pro Leu Thr Phe Gly Gly Gly Thr Lys Leu Glu Leu
            100                 105                 110

Lys

<210> SEQ ID NO 19
<211> LENGTH: 445
<212> TYPE: PRT
<213> ORGANISM: Artificial sequence
<220> FEATURE:
<223> OTHER INFORMATION: Synthetic sequence: Antibody sequence J591 DeIm
      heavy chain of PCT/GB2014/053051

<400> SEQUENCE: 19

Glu Val Gln Leu Val Gln Ser Gly Pro Glu Val Lys Lys Pro Gly Ala
1               5                   10                  15
```

```
Thr Val Lys Ile Ser Cys Lys Thr Ser Gly Tyr Thr Phe Thr Glu Tyr
             20                  25                  30

Thr Ile His Trp Val Lys Gln Ala Pro Gly Lys Gly Leu Glu Trp Ile
         35                  40                  45

Gly Asn Ile Asn Pro Asn Asn Gly Gly Thr Thr Tyr Asn Gln Lys Phe
 50                  55                  60

Glu Asp Lys Ala Thr Leu Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Leu Leu Thr
             100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
 130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
             195                 200                 205

Val Asp Lys Lys Val Glu Pro Lys Ser Cys Asp Lys Thr His Thr Cys
 210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
             275                 280                 285

Pro Arg Glu Glu Gln Tyr Asn Ser Thr Tyr Arg Val Val Ser Val Leu
 290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Asp Glu Leu Thr Lys Asn Gln Val Ser Leu Thr Cys Leu Val Lys
             355                 360                 365

Gly Phe Tyr Pro Ser Asp Ile Ala Val Glu Trp Glu Ser Asn Gly Gln
 370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430
```

His Tyr Thr Gln Lys Ser Leu Ser Leu Ser Pro Gly Lys
            435                 440                 445

<210> SEQ ID NO 20
<211> LENGTH: 214
<212> TYPE: PRT
<213> ORGANISM: Artificial sequence
<220> FEATURE:
<223> OTHER INFORMATION: Synthetic sequence: Antibody sequence J591 DeIm
      light chain of PCT/GB2014/053051

<400> SEQUENCE: 20

Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
        35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 607
<212> TYPE: PRT
<213> ORGANISM: Bos taurus

<400> SEQUENCE: 21

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

```
Glu Ser His Ala Gly Cys Glu Lys Ser Leu His Thr Leu Phe Gly Asp
                85                  90                  95
Glu Leu Cys Lys Val Ala Ser Leu Arg Glu Thr Tyr Gly Asp Met Ala
           100                 105                 110
Asp Cys Cys Glu Lys Gln Glu Pro Glu Arg Asn Glu Cys Phe Leu Ser
       115                 120                 125
His Lys Asp Asp Ser Pro Asp Leu Pro Lys Leu Lys Pro Asp Pro Asn
130                 135                 140
Thr Leu Cys Asp Glu Phe Lys Ala Asp Glu Lys Lys Phe Trp Gly Lys
145                 150                 155                 160
Tyr Leu Tyr Glu Ile Ala Arg Arg His Pro Tyr Phe Tyr Ala Pro Glu
                165                 170                 175
Leu Leu Tyr Tyr Ala Asn Lys Tyr Asn Gly Val Phe Gln Glu Cys Cys
                180                 185                 190
Gln Ala Glu Asp Lys Gly Ala Cys Leu Leu Pro Lys Ile Glu Thr Met
            195                 200                 205
Arg Glu Lys Val Leu Thr Ser Ser Ala Arg Gln Arg Leu Arg Cys Ala
    210                 215                 220
Ser Ile Gln Lys Phe Gly Glu Arg Ala Leu Lys Ala Trp Ser Val Ala
225                 230                 235                 240
Arg Leu Ser Gln Lys Phe Pro Lys Ala Glu Phe Val Glu Val Thr Lys
                245                 250                 255
Leu Val Thr Asp Leu Thr Lys Val His Lys Glu Cys Cys His Gly Asp
                260                 265                 270
Leu Leu Glu Cys Ala Asp Asp Arg Ala Asp Leu Ala Lys Tyr Ile Cys
            275                 280                 285
Asp Asn Gln Asp Thr Ile Ser Ser Lys Leu Lys Glu Cys Cys Asp Lys
        290                 295                 300
Pro Leu Leu Glu Lys Ser His Cys Ile Ala Glu Val Glu Lys Asp Ala
305                 310                 315                 320
Ile Pro Glu Asn Leu Pro Pro Leu Thr Ala Asp Phe Ala Glu Asp Lys
                325                 330                 335
Asp Val Cys Lys Asn Tyr Gln Glu Ala Lys Asp Ala Phe Leu Gly Ser
                340                 345                 350
Phe Leu Tyr Glu Tyr Ser Arg Arg His Pro Glu Tyr Ala Val Ser Val
            355                 360                 365
Leu Leu Arg Leu Ala Lys Glu Tyr Glu Ala Thr Leu Glu Glu Cys Cys
        370                 375                 380
Ala Lys Asp Asp Pro His Ala Cys Tyr Ser Thr Val Phe Asp Lys Leu
385                 390                 395                 400
Lys His Leu Val Asp Glu Pro Gln Asn Leu Ile Lys Gln Asn Cys Asp
                405                 410                 415
Gln Phe Glu Lys Leu Gly Glu Tyr Gly Phe Gln Asn Ala Leu Ile Val
            420                 425                 430
Arg Tyr Thr Arg Lys Val Pro Gln Val Ser Thr Pro Thr Leu Val Glu
        435                 440                 445
Val Ser Arg Ser Leu Gly Lys Val Gly Thr Arg Cys Cys Thr Lys Pro
    450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
```

```
                    500             505             510
Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
            530                 535                 540

Gln Ile Lys Lys Gln Thr Ala Leu Val Glu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
                580                 585                 590

Val Glu Gly Pro Lys Leu Val Val Ser Thr Gln Thr Ala Leu Ala
                595                 600                 605

<210> SEQ ID NO 22
<211> LENGTH: 750
<212> TYPE: PRT
<213> ORGANISM: Homo sapiens

<400> SEQUENCE: 22

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175
```

```
Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
        210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
                275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
```

|  |  |  | 595 |  |  |  | 600 |  |  |  | 605 |  |  |
|---|---|---|---|---|---|---|---|---|---|---|---|---|---|
| Asp | Lys | Ile | Tyr | Ser | Ile | Ser | Met | Lys | His | Pro | Gln | Glu | Met | Lys | Thr |
|  |  |  | 610 |  |  |  | 615 |  |  |  | 620 |  |  |  |  |

Tyr Ser Val Ser Phe Asp Ser Leu Phe Ser Ala Val Lys Asn Phe Thr
625                630                635                640

Glu Ile Ala Ser Lys Phe Ser Glu Arg Leu Gln Asp Phe Asp Lys Ser
              645                650                655

Asn Pro Ile Val Leu Arg Met Met Asn Asp Gln Leu Met Phe Leu Glu
              660                665                670

Arg Ala Phe Ile Asp Pro Leu Gly Leu Pro Asp Arg Pro Phe Tyr Arg
              675                680                685

His Val Ile Tyr Ala Pro Ser Ser His Asn Lys Tyr Ala Gly Glu Ser
              690                695                700

Phe Pro Gly Ile Tyr Asp Ala Leu Phe Asp Ile Glu Ser Lys Val Asp
705                710                715                720

Pro Ser Lys Ala Trp Gly Glu Val Lys Arg Gln Ile Tyr Val Ala Ala
              725                730                735

Phe Thr Val Gln Ala Ala Ala Glu Thr Leu Ser Glu Val Ala
              740                745                750

<210> SEQ ID NO 23
<211> LENGTH: 2653
<212> TYPE: DNA
<213> ORGANISM: Homo sapiens

<400> SEQUENCE: 23

```
ctcaaaaggg gccggatttc cttctcctgg aggcagatgt tgcctctctc tctcgctcgg      60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gcccgcgctg gctgtgcgct ggggcgctgg tgctggcggg tggcttcttt    360
ctcctcggct tcctcttcgg gtggtttata aaatcctcca tgaagctac taacattact    420
ccaaagcata atatgaaagc attttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga agttttcag gaaaataag    900
gttaaaatg cccagctggc aggggccaaa ggagtcattc tctactccga ccctgctgac    960
tactttgctc ctgggggtga agtcctatcca gatggttgga tcttcctgg aggtggtgtc   1020
cagcgtggaa atatcctaa tctgaatggt gcaggagacc ctctcacacc aggttaccca   1080
gcaaatgaat atgcttatag gcgtggaatt gcagaggctg ttggtcttcc aagtattcct   1140
gttcatccaa ttgatacta tgatgcacag aagctcctag aaaaaatggg tggctcagca   1200
ccaccagata gcagctggag aggaagtctc aaagtgccct acaatgttgg acctggcttt   1260
```

-continued

```
actggaaact tttctacaca aaaagtcaag atgcacatcc actctaccaa tgaagtgaca    1320
agaatttaca atgtgatagg tactctcaga ggagcagtgg aaccagacag atatgtcatt    1380
ctgggaggtc accgggactc atgggtgttt ggtggtattg accctcagag tggagcagct    1440
gttgttcatg aaattgtgag gagctttgga acactgaaaa aggaagggtg gagacctaga    1500
agaacaattt tgtttgcaag ctgggatgca gaagaatttg gtcttcttgg ttctactgag    1560
tgggcagagg agaattcaag actccttcaa gagcgtggcg tggcttatat taatgctgac    1620
tcatctatag aaggaaacta cactctgaga gttgattgta caccgctgat gtacagcttg    1680
gtacacaacc taacaaaaga gctgaaaagc cctgatgaag ctttgaagg caaatctctt    1740 tatgaaagtt ggactaaaaa aagtccttcc ccagagttca gtggcatgcc caggataagc    1800
aaattgggat ctggaaatga ttttgaggtg ttcttccaac gacttggaat tgcttcaggc    1860
agagcacggt atactaaaaa ttgggaaaca aacaaattca gcggctatcc actgtatcac    1920
agtgtctatg aaacatatga gttggtggaa aagttttatg atccaatgtt taaatatcac    1980
ctcactgtgg cccaggttcg aggagggatg gtgtttgagc tagccaattc catagtgctc    2040
ccttttgatt gtcgagatta tgctgtagtt ttaagaaagt atgctgacaa aatctacagt    2100
atttctatga aacatccaca ggaaatgaag acatacagtg tatcatttga ttcacttttt    2160
tctgcagtaa agaattttac agaaattgct tccaagttca gtgagagact ccaggacttt    2220
gacaaaagca acccaatagt attaagaatg atgaatgatc aactcatgtt tctggaaaga    2280
gcatttattg atccattagg gttaccagac aggcctttt ataggcatgt catctatgct    2340
ccaagcagcc acaacaagta tgcaggggag tcattcccag gaatttatga tgctctgttt    2400
gatattgaaa gcaaagtgga cccttccaag gcctggggag aagtgaagag acagatttat    2460
gttgcagcct tcacagtgca ggcagctgca gagactttga gtgaagtagc ctaagaggat    2520
tctttagaga atccgtattg aatttgtgtg gtatgtcact cagaaagaat cgtaatgggt    2580
atattgataa attttaaaat tggtatattt gaaataaagt tgaatattat atataaaaaa    2640
aaaaaaaaaa aaa                                                       2653
```